United States Patent
Gerwien et al.

(10) Patent No.: US 11,747,334 B2
(45) Date of Patent: Sep. 5, 2023

(54) METHODS FOR DIFFERENTIAL DIAGNOSIS OF AUTOIMMUNE DISEASES

(71) Applicant: Cowper Sciences Inc., Chandler, AZ (US)

(72) Inventors: Robert William Gerwien, San Ramon, CA (US); Theodore Michael Tarasow, San Ramon, CA (US); Jonathan Scott Melnick, San Ramon, CA (US)

(73) Assignee: COWPER SCIENCES INC., Chandler, AZ (US)

( * ) Notice: Subject to any disclaimer, the term of this patent is extended or adjusted under 35 U.S.C. 154(b) by 642 days.

(21) Appl. No.: 16/312,131

(22) PCT Filed: Jun. 20, 2017

(86) PCT No.: PCT/US2017/038391
§ 371 (c)(1),
(2) Date: Dec. 20, 2018

(87) PCT Pub. No.: WO2017/223116
PCT Pub. Date: Dec. 28, 2017

(65) Prior Publication Data
US 2020/0309774 A1    Oct. 1, 2020

Related U.S. Application Data

(60) Provisional application No. 62/421,180, filed on Nov. 11, 2016, provisional application No. 62/352,525, filed on Jun. 20, 2016.

(51) Int. Cl.
*G01N 33/564* (2006.01)
*G01N 33/68* (2006.01)

(52) U.S. Cl.
CPC ....... *G01N 33/564* (2013.01); *G01N 33/6842* (2013.01); *G01N 2570/00* (2013.01); *G01N 2800/24* (2013.01); *G01N 2800/56* (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,424,186 A | 6/1995 | Fodor et al. |
| 5,449,754 A | 9/1995 | Nishioka |
| 5,571,639 A | 11/1996 | Hubbell et al. |
| 5,593,839 A | 1/1997 | Hubbell et al. |
| 5,595,915 A | 1/1997 | Geysen |
| 5,677,195 A | 10/1997 | Winkler et al. |
| 5,759,774 A | 6/1998 | Hackett et al. |
| 5,919,523 A | 7/1999 | Sundberg et al. |
| 6,083,763 A | 7/2000 | Balch |
| 6,309,831 B1 | 10/2001 | Goldberg et al. |
| 6,329,209 B1 | 12/2001 | Wagner et al. |
| 6,346,413 B1 | 2/2002 | Fodor et al. |
| 6,346,423 B1 | 2/2002 | Schembri |
| 6,359,125 B1 | 3/2002 | Kim et al. |
| 6,365,418 B1 | 4/2002 | Wagner et al. |
| 6,387,631 B1 | 5/2002 | Arnold et al. |
| 6,399,365 B2 | 6/2002 | Besemer et al. |
| 6,465,183 B2 | 10/2002 | Wolber |
| 6,475,808 B1 | 11/2002 | Wagner et al. |
| 6,475,809 B1 | 11/2002 | Wagner et al. |
| 6,489,159 B1 | 12/2002 | Chenchik et al. |
| 6,496,309 B1 | 12/2002 | Bliton et al. |
| 6,511,277 B1 | 1/2003 | Norris et al. |
| 6,545,748 B1 | 4/2003 | Trozera |
| 6,567,163 B1 | 5/2003 | Sandstrom |
| 6,569,671 B1 | 5/2003 | Okamoto et al. |
| 6,573,369 B2 | 6/2003 | Henderson et al. |
| 6,604,902 B2 | 8/2003 | Norris et al. |
| 6,620,584 B1 | 9/2003 | Chee et al. |
| 6,630,358 B1 | 10/2003 | Wagner et al. |
| 6,660,479 B2 | 12/2003 | Kim et al. |
| 6,706,875 B1 | 3/2004 | Goldberg et al. |
| 6,723,517 B1 | 4/2004 | Bamdad |
| 6,733,977 B2 | 5/2004 | Besemer et al. |
| 6,780,582 B1 | 8/2004 | Wagner et al. |
| 6,806,954 B2 | 10/2004 | Sandstrom |

(Continued)

FOREIGN PATENT DOCUMENTS

| | | |
|---|---|---|
| CN | 1438324 A | 8/2003 |
| CN | 102099372 A | 6/2011 |

(Continued)

OTHER PUBLICATIONS

Hecker et al., Autoimmunity Reviews 11:180-190, 2012 (Year: 2012).*
Jeong et al. Molecular & Cellular Proteomics, 11:1-10. 2012 (Year: 2012).*
Fiorentino et al., Ann Rheum Dis, 75:1145-1151, Published online Aug. 7, 2015 (Year: 2015).*
Ohyama et al., Clinical Biochemistry, 48:181-185, 2015 (Year: 2015).*
Fielden et al, Bioinformatics, vol. 18, No. 5: 771-773, 2002 (Year: 2002).*
Altschul et al. Local alignment statistics. Meth. Enzymol. 266:460-480 (1996).
Assayag et al. High Resolution Computed Tomography Scoring Systems for Evaluating Interstitial Lung Disease in Systemic Sclerosis Patients. Rheumatology S1:003 (2012).

(Continued)

*Primary Examiner* — Kimberly Ballard
*Assistant Examiner* — Stacey N MacFarlane
(74) *Attorney, Agent, or Firm* — Wilson Sonsini Goodrich & Rosati

(57) ABSTRACT

Provided herein are methods, assays and devices for the differential diagnosis and detection of disease progression of autoimmune diseases. The methods, assays and devices provided herein produce and analyze binding patterns of peripheral-blood antibodies on mimetic peptide arrays that differentiate autoimmune diseases, and identify patients progressing to internal organ complications such as interstitial lung disease (ILD), and gastric antral vascular ectasia (GAVE), or renal involvement.

23 Claims, 35 Drawing Sheets

Specification includes a Sequence Listing.

(56) References Cited

U.S. PATENT DOCUMENTS

| | | |
|---|---|---|
| 6,824,669 B1 | 11/2004 | Li et al. |
| 6,877,665 B2 | 4/2005 | Challa et al. |
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |
| 7,081,954 B2 | 7/2006 | Sandstrom |
| 7,108,472 B2 | 9/2006 | Norris et al. |
| 7,130,458 B2 | 10/2006 | Bartell |
| 7,148,058 B2 | 12/2006 | Charych et al. |
| 7,247,469 B2 | 7/2007 | Wagner et al. |
| 7,354,721 B2 | 4/2008 | Tchaga |
| 7,466,851 B2 | 12/2008 | Gulati |
| 7,507,480 B2 | 3/2009 | Sugama |
| 7,522,271 B2 | 4/2009 | Sandstrom |
| 7,534,563 B2 | 5/2009 | Hargreaves |
| 7,569,343 B2 | 8/2009 | Marton et al. |
| 7,588,906 B2 | 9/2009 | Brueggemeier et al. |
| 7,622,295 B2 | 11/2009 | Cabezas |
| 7,682,797 B2 | 3/2010 | Thompson et al. |
| 7,682,798 B2 | 3/2010 | Thompson et al. |
| 7,695,919 B2 | 4/2010 | Apel et al. |
| 7,723,125 B2 | 5/2010 | Tchaga |
| 7,884,183 B2 | 2/2011 | Von et al. |
| 7,909,889 B2 | 3/2011 | Charrier et al. |
| 7,993,583 B2 | 8/2011 | Dugan et al. |
| 8,073,626 B2 | 12/2011 | Troup et al. |
| 8,148,141 B2 | 4/2012 | Nokihara et al. |
| 8,242,058 B2 | 8/2012 | Raines et al. |
| RE44,031 E | 2/2013 | Apel et al. |
| 8,969,255 B2 | 3/2015 | Johnston et al. |
| 9,709,558 B2 | 7/2017 | Johnston et al. |
| 9,970,932 B2 | 5/2018 | Woodbury et al. |
| 2003/0003516 A1 | 1/2003 | Robinson et al. |
| 2003/0082579 A1 | 5/2003 | Felgner et al. |
| 2003/0207467 A1 | 11/2003 | Snyder et al. |
| 2004/0038307 A1 | 2/2004 | Lee et al. |
| 2004/0038556 A1 | 2/2004 | French et al. |
| 2004/0048311 A1 | 3/2004 | Ault-Riche et al. |
| 2004/0063902 A1 | 4/2004 | Miranda |
| 2004/0071705 A1 | 4/2004 | Sato et al. |
| 2004/0253636 A1 | 12/2004 | Soloviev et al. |
| 2005/0009204 A1 | 1/2005 | Fang et al. |
| 2005/0048566 A1 | 3/2005 | Delisi et al. |
| 2005/0064395 A1 | 3/2005 | Israel et al. |
| 2005/0255491 A1 | 11/2005 | Lee et al. |
| 2006/0013971 A1 | 1/2006 | Chen et al. |
| 2006/0024677 A1 | 2/2006 | Morris et al. |
| 2006/0052948 A1 | 3/2006 | Gorlach |
| 2006/0121490 A1 | 6/2006 | He |
| 2007/0003954 A1 | 1/2007 | Kodadek et al. |
| 2007/0015172 A1 | 1/2007 | Zhang et al. |
| 2007/0020678 A1 | 1/2007 | Ault-Riche et al. |
| 2007/0099256 A1 | 5/2007 | Sundararajan et al. |
| 2007/0122841 A1 | 5/2007 | Rajasekaran et al. |
| 2008/0026485 A1 | 1/2008 | Hueber et al. |
| 2008/0124719 A1 | 5/2008 | Chung et al. |
| 2008/0188618 A1 | 8/2008 | Greving et al. |
| 2008/0193965 A1 | 8/2008 | Zeng et al. |
| 2008/0207507 A1 | 8/2008 | Lau et al. |
| 2009/0054251 A1 | 2/2009 | O'Connor et al. |
| 2009/0131278 A1 | 5/2009 | Wagner et al. |
| 2009/0142792 A1 | 6/2009 | Robinson et al. |
| 2009/0176664 A1 | 7/2009 | Chu |
| 2010/0035765 A1 | 2/2010 | Kodadek |
| 2010/0064393 A1 | 3/2010 | Berka et al. |
| 2010/0105086 A1 | 4/2010 | Landolfo et al. |
| 2010/0210478 A1 | 8/2010 | Gao et al. |
| 2010/0261205 A1 | 10/2010 | Kakuta et al. |
| 2011/0046015 A1 | 2/2011 | Honda et al. |
| 2011/0065594 A1 | 3/2011 | Thompson et al. |
| 2011/0105366 A1 | 5/2011 | Lebl et al. |
| 2011/0190149 A1 | 8/2011 | Tainsky et al. |
| 2011/0275537 A1 | 11/2011 | Rychlewski et al. |
| 2011/0301057 A1 | 12/2011 | Propheter et al. |
| 2011/0301058 A1 | 12/2011 | Cheng et al. |
| 2011/0319291 A1 | 12/2011 | Vrijbloed et al. |
| 2012/0004130 A1 | 1/2012 | Mattoon et al. |
| 2012/0134920 A1 | 5/2012 | D'Souza et al. |
| 2012/0189702 A1 | 7/2012 | Gupta |
| 2012/0190574 A1 | 7/2012 | Johnston et al. |
| 2012/0238477 A1 | 9/2012 | Albert et al. |
| 2013/0071860 A1 | 3/2013 | Hale et al. |
| 2013/0079250 A1 | 3/2013 | Johnston et al. |
| 2013/0143756 A1 | 6/2013 | Johnston et al. |
| 2013/0310265 A1 | 11/2013 | Menegatti et al. |
| 2014/0087963 A1* | 3/2014 | Johnston ............ G01N 33/6854 506/9 |
| 2014/0135225 A1 | 5/2014 | Crow et al. |
| 2014/0342939 A1 | 11/2014 | Cohen et al. |
| 2015/0108344 A1 | 4/2015 | Anderson et al. |
| 2015/0119289 A1 | 4/2015 | Chen et al. |
| 2015/0217258 A1 | 8/2015 | Woodbury et al. |
| 2015/0241420 A1 | 8/2015 | Johnston et al. |
| 2016/0041153 A1 | 2/2016 | Brown et al. |
| 2016/0041158 A1 | 2/2016 | Woodbury et al. |
| 2016/0067667 A1 | 3/2016 | Rajasekaran et al. |
| 2016/0131662 A1 | 5/2016 | Kodadek |
| 2017/0030906 A1 | 2/2017 | Mesa et al. |
| 2017/0106344 A1 | 4/2017 | Woodbury et al. |
| 2017/0212101 A1 | 7/2017 | Zhu et al. |
| 2019/0234945 A1 | 8/2019 | Rowe et al. |
| 2020/0064345 A1 | 2/2020 | Sykes et al. |
| 2020/0116715 A1 | 4/2020 | Gerwien et al. |
| 2020/0209236 A1 | 7/2020 | Gerwien et al. |

FOREIGN PATENT DOCUMENTS

| | | |
|---|---|---|
| CN | 102361646 A | 2/2012 |
| CN | 103025890 A | 4/2013 |
| CN | 103776891 A | 5/2014 |
| CN | 104271746 A | 1/2015 |
| EP | 0476014 B1 | 8/1994 |
| EP | 0728520 A1 | 8/1996 |
| EP | 1785726 A1 | 5/2007 |
| JP | 2002540382 A | 11/2002 |
| JP | 2012508011 A | 4/2012 |
| JP | 2012530906 A | 12/2012 |
| JP | 2013188212 A | 9/2013 |
| JP | 2015528912 A | 10/2015 |
| JP | 2016502095 A | 1/2016 |
| WO | WO-9015070 A1 | 12/1990 |
| WO | WO-9118980 A1 | 12/1991 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-9609668 A1 | 3/1996 |
| WO | WO-9727329 A1 | 7/1997 |
| WO | WO-0004382 A1 | 1/2000 |
| WO | WO-0156691 A2 | 8/2001 |
| WO | WO-02097051 A2 | 12/2002 |
| WO | WO-03019192 A1 | 3/2003 |
| WO | WO-2004053068 A2 | 6/2004 |
| WO | WO-2005050224 A2 | 6/2005 |
| WO | WO-2007068240 A2 | 6/2007 |
| WO | WO-2007147141 A2 | 12/2007 |
| WO | WO-2008048970 A2 | 4/2008 |
| WO | WO-2008085185 A2 | 7/2008 |
| WO | WO-2008151146 A2 | 12/2008 |
| WO | WO-2009140039 A2 | 11/2009 |
| WO | WO-2010043668 A1 | 4/2010 |
| WO | WO-2010053587 A2 | 5/2010 |
| WO | WO-2010148365 A2 | 12/2010 |
| WO | WO-2011026200 A2 | 3/2011 |
| WO | WO-2011045745 A1 | 4/2011 |
| WO | WO-2011109440 A1 | 9/2011 |
| WO | WO-2011150168 A1 | 12/2011 |
| WO | WO-2012007622 A1 | 1/2012 |
| WO | WO-2012055069 A1 | 5/2012 |
| WO | WO-2014062981 A1 | 4/2014 |

(56) References Cited

FOREIGN PATENT DOCUMENTS

| WO | WO-2014036312 A3 | 5/2015 |
|---|---|---|
| WO | WO-2015095136 A1 | 6/2015 |
| WO | WO-2016005295 A1 | 1/2016 |
| WO | WO-2016040703 A1 | 3/2016 |
| WO | WO-2017223116 A2 | 12/2017 |
| WO | WO-2017223117 A1 | 12/2017 |
| WO | WO-2017223116 A3 | 2/2018 |
| WO | WO-2018089554 A1 | 5/2018 |
| WO | WO-2018089556 A1 | 5/2018 |
| WO | WO-2018156808 A2 | 8/2018 |
| WO | WO-2018236838 A2 | 12/2018 |

OTHER PUBLICATIONS

Favoino et al. Autoantibodies recognizing the amino terminal 1-17 segment of CENP-A display unique specificities in systemic sclerosis. PLoS One 8(4):e61453 (2013).

Hecker et al. Computational analysis of high-density peptide microarray data with application from systemic sclerosis to multiple sclerosis. Autoimmunity Reviews 11:180-190 (2012).

Henikoff et al. Amino acid substitution matrices from protein blocks. PNAS USA 89(22):10915-10919 (1992).

Kukreja et al. Comparative study of classification algorithms for immunosignaturing data. BMC Bioinformatics 13:139 (2012).

Lisnevskaia et al. Systemic lupus erythematosus. Lancet 384(9957):1878-88 (2014).

Medsger et al. Assessment of disease severity and prognosis. Clin Exper Rheumatol 21:S42-S46 (2003).

Oglesby et al. Impact of Early Versus Late Systemic Lupus Erythematosus Diagnosis on Clinical and Economic Outcomes. Applied Health Economics & Health Policy 12(2):179-90 (2014).

PCT/US2017/038391 International Search Report and Written Opinion dated Dec. 11, 2017.

PCT/US2017/038391 Invitation to Pay Additional Fees dated Oct. 5, 2017.

States et al. Improved sensitivity of nucleic acid database searches using application-specific scoring matrices. Methods 3:66-70 (1991).

Tan et al. Autoantibodies to fibrillin 1 in systemic sclerosis: ethnic differences in antigen recognition and lack of correlation with specific clinical features or HLA alleles. Arthritis Rheum 43(11):2464-71 (2000).

Zou et al. Regularization and Variable Selection via the Elastic Net. J R Statist Soc B 67(Part 2):301-320 (2005).

Agarwal, et al. Disregulated expression of the Th2 cytokine gene in patients with intraoral squamous cell carcinoma. Immunol Invest. Feb. 2003;32(1-2):17-30.

Alpert et al., A clinically meaningful metric of immune age derived from high-dimensional longitudinal monitoring. Nature Medicine. 25(3):487-495 (2019). doi: 10.1038/S41591-019-0381-y. Epub Mar. 6, 2019.

Anderson, et al. The human plasma proteome: history, character, and diagnostic prospects. Mol Cell Proteomics. Nov. 2002;1(11):845-67.

Andresen et al., Deciphering the Antibodyome Peptide Arrays for Serum Antibody Biomarker Diagnostics, Current Proteomics, 6;1-12 (2009).

Anic et al., New classification criteria for systemic lupus erthematosus correlate with disease activity. Croat Med J. 55: 514-519 (2014).

Bailey. MEME: discovering and analyzing DNA and protein sequence motifs. (2006) Nucleic Acids Res. 34(suppl 2): W369-W373.

Bauer et al., Identification and Quantification of a New Family of Peptide Endocannabinoids (Pepcans) Showing Negative Allosteric Modulation at CB1 Receptors, Journal of Biological Chemistry (2012) 287(44); 36944-36967.

Benjamini e al. Controlling the false discovery rate: a practical and powerful approach to multiple testing. Journal of the Royal Statistical Society. Series B (Methodological). pp. 289-300 (1995).

Berglund, et al. A Genecentric Human Protein Atlas for Express Profiles Based on antibodies. Oct. 1, 2008, Molecular and Cellular Proteomics, 7, pp. 2019-2027.

Bern, C.: Chagas' Disease. N Engl J Med. 373(19): 1881-1882 (2015).

Bern et al.: An estimate of the burden of Chagas disease in the United States. Clin Infect Dis. 49(5): e52-e54 (2009).

Boltz, et al. Peptide microarrays for carbohydrate recognition. Analyst. Apr. 2009;134(4):650-2. doi: 10.1039/b823156g. Epub Feb. 11, 2009.

Bombardier et al., Derivation of the SLEDAI. Arthritis and Rheumatism 35(6) (1992).

Borrebaeck. Antibodies in diagnostics—from immunoassays to protein chips. Immunol Today. Aug. 2000;21(8):379-82.

Breitling F. et al. High-density peptide arrays. Mol. BioSyst., vol. 5, pp. 224-234, 2009.

Brown, et al. Statistical methods for analyzing immunosignatures. BMC Bioinformatics. Aug. 19, 2011;12:349. doi: 10.1186/1471-2105-12-349.

Brown, et al. The preclinical natural history of serous ovarian cancer: defining the target for early detection. PLoS Med. Jul. 2009;6(7):e1000114. doi: 10.1371/journal.pmed.1000114. Epub Jul. 28, 2009.

Brusic, et al. Information technologies for vaccine research. Expert Rev Vaccines. Jun. 2005;4(3):407-17.

Buscaglia et al.: The surface coat of the mammal-dwelling infective trypomastigote stage of Trypanosoma cruzi is formed by highly diverse immunogenic mucins. J Biol Chem. 279(16):15860-15869 (2004).

Busch et al.: Virus and antibody dynamics in acute west nile virus infection. J Infect Dis. 198(7): 984-993 (2008).

Butler, et al. The immunochemistry of sandwich ELISAs-VI. Greater than 90% of monoclonal and 75% of polyclonal anti-fluorescyl capture antibodies (CAbs) are denatured by passive adsorption. Mol Immunol. Sep. 1993;30(13):1165-75.

Butler. Solid supports in enzyme-linked immunosorbent assay and other solid-phase immunoassays. Methods. Sep. 2000;22(1):4-23.

Carmona et al., Towards High-throughput Immunomics for Infectious Diseases: Use of Next-generation Peptide Microarrays for Rapid Discovery and Mapping of Antigenic Determinants. Mol Cell Proteomics 14(7):1871-1884 (2015).

Casey, et al. Phage display of peptides in ligand selection for use in affinity chromatography. Methods Mol Biol. 2008;421:111-24.

Cenci, et al. Managing and exploiting stress in the antibody factory. FEBS Lett. Jul. 31, 2007;581(19):3652-7. Epub Apr. 24, 2007.

Cerecedo, et al. Mapping of the IgE and IgG4 sequential epitopes of milk allergens with a peptide microarray-based immunoassay. J Allergy Clin Immunol. Sep. 2008;122(3):589-94. doi: 10.1016/j.jaci.2008.06.040.

Chase et al.,. Evaluation of biological sample preparation for immunosignature-based diagnostics. Clinical Vaccine and Immunology. 19(3):352-358 (2012).

Chatelain, E.: Chagas disease research and development: Is there light at the end of the tunnel? Comput Struct Biotechnol J. 15: 98-103 (2016; eCollection 2017).

Chen, et al. Identification of multiple cancer/testis antigens by allogeneic antibody screening of a melanoma cell line library. Proc Natl Acad Sci U S A. Jun. 9, 1998;95(12):6919-23.

Chene, P., Challenges in Design of Biochemical Assays for the Identification of Small Molecules to Target Multiple Conformations of Protein Kinases. Drug Discovery Today, 13(11/12); 522-529 (2008).

Cheng et al.: Immunoblot assay using recombinant antigens as a supplemental test to confirm the presence of antibodies to Trypanosoma cruzi. Clin Vaccine Immunol. 14(4): 355-361 (2007).

Choung et al., Determination of B-Cell Epitopes in Patients with Celiac Disease: Peptide Microarrays. Plos One 11(1): e014777 (2016).

Christian, R.B., et al. (1992) Simplified methods for construction, assessment and rapid screening of peptide libraries in bacteriophage. Journal of Molecular Biology 227, 711-718.

(56) References Cited

OTHER PUBLICATIONS

Clayton, J.: Chagas disease 101. Nature. 465(7301): S4-S5 (2010).
Cooley et al., High throughput selection of effective serodiagnostics for Trypanosoma cruzi infection. PLoS Negl Trop Dis 2(10):e316 (2008).
Cooperman, et al. Cell division rates of primary human precursor B cells in culture reflect in vivo rates. Stem Cells. 2004;22(6):1111-20.
Cortes et al., Support-vector networks. Machine Learning. 1995; 20:273-297.
Cretich, et al. Epitope mapping of human chromogranin A by peptide microarrays. Methods Mol Biol. 2009;570:221-32. doi: 10.1007/978-1-60327-394-7_10.
Cretich. Protein and peptide arrays: Recent trends and new directions. (2006) Biomol. Eng. 23: 77-88 (2006).
Crooks, et al. WebLogo: a sequence logo generator. Genome Res. Jun. 2004;14(6):1188-90.
Daver, et al. The usefulness of prostate-specific antigen and prostatic acid phosphatase in clinical practice. Am J Clin Oncol. 1988;11 Suppl 2:S53-60.
De Pablos et al.: Multigene families in Trypanosoma cruzi and their role in infectivity. Infect Immun. 80(7): 2258-2264 (2012).
De Paz, J.L. et la. Exploration of the use of an acylsulfonamide safety-catch linker for the polymer-supported synthesis of hyaluronic acid oligosaccharides. Carbohydr Res. Mar. 30, 2010;345(5):565-71. Epub Jan. 4, 2010.
De Rycker et al.: Identification of Trypanocidal Activity for Known Clinical Compounds Using a New Trypanosoma cruzi Hit-Discovery Screening Cascade. PLoS Negl Trop Dis.10(4): e0004584 (2016).
DeLong et al. Comparing the areas under two or more correlated receiver operating characteristic curves: a nonparametric approach. Biometrics (1988); 44(3): 837-845.
Derda, et al. Diversity of phage-displayed libraries of peptides during panning and amplification. Molecules. Feb. 21, 2011;16(2):1776-803. doi: 10.3390/molecules16021776.
Diehnelt, et al. Discovery of high-affinity protein binding ligands—backwards. PLoS One. May 19, 2010;5(5):e10728. doi: 10.1371/journal.pone.0010728.
Draghici. Statistics and Data Analysis for Microarrays Using R and Bioconductor. Chapman & Hall/CRC. 2012.
Engvall, et al. Enzyme-linked immunosorbent assay (ELISA). Quantitative assay of immunoglobulin G. Immunochemistry. Sep. 1971;8(9):871-4.
EP 10790305.6 Extended European Search Report dated Aug. 20, 2013.
European Application No. 17816082.6 Extended European Search Report dated Apr. 9, 2020.
European U.S. Appl. No. 18821115 Search Report dated Apr. 9, 2021.
European Patent Application No. 13 833992.4 European Search Report dated Apr. 25, 2016.
European U.S. Appl. No. 18757099 Search Report dated Jan. 18, 2021.
Falsey, J.R., et al. Peptide and small molecule microarray for high throughput cell adhesion and functional assays. Bioconjugate Chem. (2001) 12, 346-353.
Fodor. Multiplexed biochemical assays with biological chips. Nature 364:555-556 (1993).
Folgori, A., et al. A general strategy to identify mimotopes of pathological antigens using only random peptide libraries and human sera. (1994) EMBO Journal, vol. 13, No. 9, pp. 2236-2243.
Foong, et al. Current advances in peptide and small molecule microarray technologies. Curr Opin Chem Biol. Apr. 2012;16(1-2):234-42. doi: 10.1016/j.cbpa.2011.12.007. Epub Jan. 3, 2012.
Forster, et al. The bulk of the peripheral B-cell pool in mice is stable and not rapidly renewed from the bone marrow. Proc Natl Acad Sci U S A. Jun. 1990;87(12):4781-4.
Frith. Discovering Sequence Motifs with Arbitrary Insertions and Deletions. (2008) PLOS Comput. Biol. 4: e1000071.

Fu et al., Exploring peptide space for enzyme modulators, J. Am. Chem. Soc., Apr. 2010, 6419-6424, vol. 132, No. 18.
Fu, et al. Peptide-modified surfaces for enzyme immobilization. PLoS One. Apr. 8, 2011;6(4):e18692. doi: 10.1371/journal.pone. 0018692.
Gallina, et al. Prediction of pathological stage is inaccurate in men with PSA values above 20 ng/mL. Eur Urol. Nov. 2007;52(5):1374-80. Epub Dec. 11, 2006.
Geysen, et al. Use of peptide synthesis to probe viral antigens for epitopes to a resolution of a single amino acid. Proc Natl Acad Sci U S A. Jul. 1984;81(13):3998-4002.
Gomes et al.: Diagnosis of Chagas disease: what has been achieved? What remains to be done with regard to diagnosis and follow up studies? Mem Inst Oswaldo Cruz. 104 Suppl 1: 115-121 (2009).
Granjon et al.: Development of a Novel Multiplex Immunoassay Multi-cruzi for the Serological Confirmation of Chagas Disease. PLoS Negl Trop Dis. 10(4): e0004596 (2016).
Greving, et al. High-throughput screening in two dimensions: binding intensity and off-rate on a peptide microarray. Anal Biochem. Jul. 1, 2010;402(1):93-5. doi: 10.1016/j.ab.2010.03.002. Epub Mar. 6, 2010.
Greving, et al. Thermodynamic additivity of sequence variations: an algorithm for creating high affinity peptides without large libraries or structural information. PLoS One. Nov. 11, 2010;5(11):e15432. doi: 10.1371/journal.pone.0015432.
Gupta, N., et al. Engineering a synthetic ligand for tumor necrosis factor-alpha.(2011) Bioconjugate Chemistry, vol. 22, pp. 1473-1478.
Haft et al.: Human orthologs of yeast vacuolar protein sorting proteins Vps26, 29, and 35: assembly into multimeric complexes. Mol Biol Cell. 11(12): 4105-4116 (2000).
Halperin et al. Exploring Antidbody Recognition of Sequence Space Through Random-Sequence Peptide Microarrays. Molecular & Cellular Proteomics 10.3:1-10 (2011).
Hanash, S. Disease proteomics. (Mar. 2003) Nature vol. 422, pp. 226-232.
Hao, et al. Homeostasis of peripheral B cells in the absence of B cell influx from the bone marrow. J Exp Med. Oct. 15, 2001;194(8):1151-64.
Hori, et al. Mathematical model identifies blood biomarker-based early cancer detection strategies and limitations. Sci Transl Med. Nov. 16, 2011;3(109):109ra116. doi: 10.1126/scitranslmed. 3003110.
Huang, et al. MIMOX: a web tool for phage display based epitope mapping. BMC Bioinformatics. Oct. 12, 2006;7:451.
Hughes, et al. Immunosignaturing can detect products from molecular markers in brain cancer. PLoS One. 2012;7(7):e40201. doi: 10.1371/journal.pone.0040201. Epub Jul. 16, 2012.
International Application No. PCT/US2018/019287 International Search Report and Written Opinion dated Aug. 10, 2018.
International search report and written opinion dated Oct. 22, 2012 for PCT/US2012/036631.
International search report and written opinion dated Feb. 3, 2014 for PCT/US2013/057373.
International search report dated Dec. 20, 2013 for PCT/US2013/065541.
Issa et al.: Antitrypanosomal agents: treatment or threat? Lancet. 376(9743): 768 (2010).
Janeway, et al. Immunobiology: The Immune System in Health and Disease. Current Biology Limited. 1997.
Jollymore, M. "Virus research aims to prevent or reverse immune-system aging," Nova Scotia Health Authority Research Annual Report 2017, Feb. 21, 2018, pp. 1-2. Retrieved from the Internet:http://www.nshealth.ca/news/virus-research-aims-prevent-or-reverse-immune-system-aging Oct. 15, 2019.
Jonassen. Efficient discovery of conserved patterns using a pattern graph. (1997) Comput. Appl. Biosci. 13: 509-22.
Keating et al.: Inflammatory and cardiac biomarkers are differentially expressed in clinical stages of Chagas disease. Int J Cardiol. 199: 451-459 (2015).
Kroening, et al. Autoreactive antibodies raised by self derived de novo peptides can identify unrelated antigens on protein microar-

(56) References Cited

OTHER PUBLICATIONS rays. Are autoantibodies really autoantibodies? Exp Mol Pathol. Jun. 2012;92(3):304-11. doi: 10.1016/j.yexmp.2012.03.002. Epub Mar. 8, 2012.

Kukreja, M., et al. Immunosignaturing Microarrays Distinguish Antibody Profiles of Related Pancreatic Diseases. (2012) Journal of Proteomics & Bioinformatics, vol. S6, pp. 001.

Lander et al.: Localization and developmental regulation of a dispersed gene family 1 protein in Trypanosoma cruzi. Infect Immun. 78(1): 231-240 (2010).

Legutki et al., A general method for characterization of humoral immunity induced by a vaccine or infection. Vaccine. 28(28):4529-4537 (2010).

Legutki, J.B., et al. Scalable high-density peptide arrays for comprehensive health monitoring. Nature Communications, vol. 5, p. 4785; (Sep. 3, 2014).

Lewczuk, et al. Amyloid beta peptides in plasma in early diagnosis of Alzheimer's disease: A multicenter study with multiplexing. Exp Neurol. Jun. 2010;223(2):366-70. doi: 10.1016/j.expneurol.2009.07.024. Epub Aug. 5, 2009.

Lin, et al. Development of a novel peptide microarray for large-scale epitope mapping of food allergens. J Allergy Clin Immunol. Aug. 2009;124(2):315-22, 322.e1-3. doi: 10.1016/j.jaci.2009.05.024. Epub Jul. 3, 2009.

Liu et al. Towards proteome-wide production of monoclonal antibody by phage display. J Mol Biol. 315(5):1063-1073 (2002).

Liu, R., et al. Combinatorial peptide library methods for immunobiology research. (2003) Experimental Hematology vol. 31, pp. 11-30.

Lorenz, P., et al. Probing the epitope signatures ofIgG antibodies in human serum from patients with autoimmune disease. (2009) Methods in Molecular Biology, Epitope Mapping Protocls, vol. 524, pp. 247-258.

Mackey, et al. Getting more from less: algorithms for rapid protein identification with multiple short peptide sequences. Mol Cell Proteomics. Feb. 2002;1(2):139-47.

Manson et al., Systemic Lupus Erythematosus. Orphanet J Rare Dis 1:6 (2006).

McCullough et al.: The nation's changing blood supply system. JAMA. 269(17): 2239-2245 (1993).

McDade, et al. What a Drop Can Do: Dried Blood Spots as a Minimally Invasive Method for Integrating Biomarkers Into Population-Based Research, Demography 44(4):899-925 (2007).

Merbl, et al. A Systems Immunology Approach to the Host-Tumor Interaction: Large-Scale Patterns of Natural Autoantibodies Distinguish Healthy and Tumor-Bearing Mice. PLoS One vol. 4, Issue 6, p. e6053. Jun. 2009.

Mestas, et al., Of Mice and Not Men: Differences Between Mouse and Human Immunology, The Journal of Immunology, 172;2731-2738 (2004).

Min et al. Peptide arrays: towards routine implementation. Current Opinion in Chemical Biology vol. 8, pp. 554-558, 2004.

Miseta, Attila et al. Relationship Between the Occurrence of Cysteine in Proteins and the Complexity of Organisms. (2000) Mol. Biol. Evol., vol. 17, pp. 1232-1239.

Mitra et al., Self-assembly of cyclic metal-DNA nanostructures using ruthenium tris(bipyridine)-branchedoligonucleotides. Agnewandte Chemie. 43(43):5804-5808 (2004).

Mohan, S., et al. Association energetics of cross-reactive and specific antibodies. (Feb. 17, 2009) Biochemistry vol. 48, No. 6, pp. 1390-1398.

Moller, et al. DNA probes on chip surfaces studied by scanning force microscopy using specific binding of colloidal gold. Nucleic Acids Res. Oct. 15, 2000;28(20):E91.

Morales Betanzos, et al. Bacterial glycoprofiling by using random sequence peptide microarrays. Chembiochem. Mar. 23, 2009;10(5):877-88. doi: 10.1002/cbic.200800716.

Moreau, et al. Discontinuous epitope prediction based on mimotope analysis. Bioinformatics. May 1, 2006;22(9):1088-95. Epub Jan. 24, 2006.

Morillo et al.: Randomized Trial of Benznidazole for Chronic Chagas' Cardiomyopathy. N Engl J Med. 373(14): 1295-1306 (2015).

Moudgil et al. Cytokines in autoimmunity: Role in induction, regulation, and treatment, J. Interferon & Cytokine Res, 31(10):695-703 (2011).

Navalkar, K.A. et al. Peptide based diagnostics: Are random-sequence peptides more useful than tiling proteome sequences? Journal of Immunological Methods, vol. 417, pp. 10-21 (2015).

Neufing et al., Exposure and Binding of Selected Immunodominant La/SSB Epitopes on Human Apoptotic Cells. Arthritis Rheum 52(12): 3934-3942 (2005).

Neuman De Vegvar, et al. Microarray profiling of antiviral antibodies for the development of diagnostics, vaccines, and therapeutics. (2004) Clinical Immunology, vol. 111 pp. 196-201.

No Author. Affymetrix, GeneChip Human Genome Arrays Data Sheet, pp. 1-4 (2003).

No Author. NSB9 Amine Slide, NSB Postech, 2007, http://www.nsbpostech.com/2007/products/slide.html.

No Author. Pubchem CID 110154. Created: Aug. 8, 2005. Date accessed: Feb. 26, 2018, pp. 1-15.

Nobrega, A., et al. Functional diversity and clonal frequencies of reactivity in the available antibody repertoire. (1998) European Journal of Immunology vol. 28, pp. 1204-1215.

Office action dated Apr. 8, 2013 for U.S. Appl. No. 13/379,080.
Office action dated Sep. 12, 2014 for U.S. Appl. No. 13/379,080.
Office action dated Sep. 20, 2013 for U.S. Appl. No. 13/624,332.
Office action dated Sep. 20, 2013 for U.S. Appl. No. 13/624,386.
Office action dated Oct. 3, 2013 for U.S. Appl. No. 13/379,080.

Oliveira et al.: Perspectives in Chagas disease treatment. Glob Heart. 10(3): 189-192 (2015).

Panicker, R.C., et al. Recent advances in peptide-based microarray technologies. (2004) Combinatorial Chemistry & High Throughput Screening vol. 7, pp. 547-556.

PCT/US2017/038392 International Search Report and Written Opinion dated Sep. 8, 2017.
PCT/US2017/060721 International Search Report and Written Opinion dated Feb. 26, 2018.
PCT/US2017/060724 International Search Report and Written Opinion dated Mar. 13, 2018.
PCT/US2018/019287 International Preliminary Report on Patentability dated Sep. 6, 2019.
PCT/US2018/038240 International Preliminary Report on Patentability dated Dec. 24, 2019.
PCT/US2018/038240 International Search Report and Written Opinion dated Dec. 27, 2018.
PCT/US2019/017326 International Search Report and Written Opinion dated Jun. 3, 2019.
PCT/US2019/017326 Invitation to Pay Additional Fees dated Apr. 12, 2019.
PCT/US2019/028791 International Search Report and Written Opinion dated Oct. 15, 2019.

Pecoul et al.: The Benefit Trial: Where Do We Go from Here? PLoS Negl Trop Dis. 10(2): e0004343 (2016).

Perez et al.: Chagas disease: the challenge of polyparasitism? Trends Parasitol. 30(4): 176-182 (2014).

Perez-Gordo, et al. Epitope mapping of Atlantic salmon major allergen by peptide microarray immunoassay. Int Arch Allergy Immunol. 2012;157(1):31-40. doi: 10.1159/000324677. Epub Sep. 5, 2011.

Pinazo et al.: Biological markers for evaluating therapeutic efficacy in Chagas disease, a systematic review. Expert Rev Anti Infect Ther. 12(4): 479-496 (2014).

Pinazo et al.: Immunosuppression and Chagas disease: a management challenge. PLoS Negl Trop Dis. 7(1): e1965 (2013).

Praast et al.: Evaluation of the Abbott Architect Chagas prototype assay. Diagn Microbiol Infect Dis. 69(1): 74-81 (2011).

Price et al., On silico peptide microarrays for high-resolution mapping of antibody epitopes and diverse protein-protein interactions, Nat Med, Sep. 2012, 1434-40, vol. 18, No. 9.

Quackenbush, et al. Computational Analysis of Microarray Data, Nature Reviews, 2;418-427 (2001).

(56) References Cited

OTHER PUBLICATIONS

Quintana, et al., Antigen-chip technology for accessing global information about the state of the body. 2006 Lupus vol. 15, pp. 428-430.
Quintana, et al. The Natural autoantibody repertoire and autoimmune disease. Biomedicine & Pharmacotherapy vol. 58 (2004) pp. 276-281.
Rassi et al.: Chagas disease. Lancet. 375(9723): 1388-1402 (2010).
Reddy, et al. Identification of candidate IgG biomarkers for Alzheimer's disease via combinatorial library screening. Cell. Jan. 7, 2011;144(1):132-42. doi: 10.1016/j.cell.2010.11.054.
Reddy, et al., Protein fingerprinting in complex mixtures with peptoid microarrays. Proc. of The Nat'l Academy of Sciences, Nat'l Academy of Sciences, US, 102(36):12672-12677 Sep. 2005.
Reineke, et al., Epitope Mapping Protocols, Method in Molecular Biology 524, 2nd Edition, Huma Press. 1-447 (2009).
Reineke, et al. Identification of Distinct Antibody Epitopes and mimotopes from a peptide array of 5520 randomly generated sequences. Journal of Immunological Methods vol. 267 (2002) pp. 37-51.
Remesar et al.: Bimodal distribution of Trypanosoma cruzi antibody levels in blood donors from a highly endemic area of Argentina: what is the significance of low-reactive samples? Transfusion. 55(10): 2499-2504 (2015).
Restrepo, et al. Application of immunosignatures to the assessment of Alzheimer's disease. Ann Neurol. Aug. 2011;70(2):286-95. doi: 10.1002/ana.22405.
Rigoutsos. In Silico Pattern-Based Analysis of the Human Cytomegalovirus Genome. (1998) Bioinformatics 14: 55-67.
Roobol. Contemporary role of prostate cancer gene 3 in the management of prostate cancer. Curr Opin Urol. May 2011;21(3):225-9. doi: 10.1097/MOU.0b013e328344939c.
Shreffler, W.G., et al. IgE and IgG4 epitope mapping by microarray immunoassay reveals the diversity of immune response to the peanut allergen, Ara h 2. (2005) J Allergy Clin Immunol vol. 116, No. 4, pp. 893-899.
Sodre et al.: Proteomic map of Trypanosoma cruzi CL Brener: the reference strain of the genome project. Arch Microbiol. 191(2): 177-184. Epub Nov. 11, 2008. (2009).
Sokolove et al., Development and deployment of antigen arrays for investigation of B-cell specificity in autoimmune disease. Frontiers in Bioscience E4: 320-330 (2012).
Stafford et al., Immunosignature system for diagnosing cancer. PNAS: E3072-E3080 (2014).
Stafford, et al. Physical characterization of the "immunosignaturing effect". Mol Cell Proteomics. Apr. 2012;11(4):M111.011593. doi: 10.1074/mcp.M111.011593. Epub Jan. 18, 2012.
Stafford P. and Johnston,Microarray technology displays the complexities of the humoral immune response. Expert Rev. Mol. Diagn. vol. 11, No. 1, pp. 5-8, Jan. 2011.
Stafford, P., et al Immunosignature system for diagnosis of cancer. PNAS, vol. 111, No. 30; pp. E3072-E3080 (Jul. 14, 2014).
Steverding, D.: The history of Chagas disease. Parasit Vectors. 7: 317 (2014).
Sulzer, et al. Memory in idiotypic networks due to competition between proliferation and differentiation. Bull Math Biol. Nov. 1993;55(6):1133-82.
Szardenings, M. Phage display of random peptide libraries: applications, limits, and potential. (2003) Journal of Receptors and Signal Transduction, vol. 23, No. 4, pp. 307-349.
Tang et al., Current Developments in SELDI Affinity Technology, Mass Spectrometry Reviews 23;34-44 (2004).
Tarawow et al., Immunosignature Autoantibody Profiles Provide Mechanistic Insight into Systemic Lupus Erythematosus and Differentiation from Symptomatically Overlapping Diseases. Retrieved from http://www.healthtell.com/wp-content/uploads/2018/06/5-HealthTell_ACR2017_poster_SLE (2017).
Tedesco, et al. A new strategy for the early diagnosis of rheumatoid arthritis: a combined approach. Autoimmun Rev. Jan. 2009;8(3):233-7. doi: 10.1016/j.autrev.2008.07.031. Epub Aug. 15, 2008.
Thompson, et al. Prostate-specific antigen in the early detection of prostate cancer. CMAJ. Jun. 19, 2007;176(13):1853-8.
Thorpe, I.F., and Brooks, C.L., Molecular evolution of affinity and flexibility in the immune system. (May 22, 2007) PNAS vol. 104, No. 21, pp. 8821-8826.
Tobler et al.: Evaluation of a new enzyme-linked immunosorbent assay for detection of Chagas antibody in US blood donors. Transfusion. 47(1): 90-96 (2007).
Torzewski et al., Animal Models of C-Reactive Protein. Hindawl Publishing Corporation, Mediators of Inflammation, pp. 1-7 (2014).
Uhlen, M., et al. Generation and validation of affinity reagents on a proteome-wide level. (2009) Journal of Molecular Recognition, vol. 22, pp. 57-64.
United States Patent and Trademark Office, Subject Matter Eligibility Examples: Life Sciences, Subject Matter Eligibility Update, 2016, 1-31.
U.S. Appl. No. 13/379,080 Final Office Action dated Jul. 21, 2015.
U.S. Appl. No. 13/379,080 Final Office action dated Apr. 8, 2013.
U.S. Appl. No. 13/379,080 Final Office action dated Oct. 3, 2013.
U.S. Appl. No. 13/379,080 Final Office action dated Sep. 12, 2014.
U.S. Appl. No. 13/379,080 Office Action dated Aug. 4, 2016.
U.S. Appl. No. 13/379,080 Office action dated Oct. 11, 2012.
U.S. Appl. No. 13/624,332 Final Office Action dated Feb. 28, 2018.
U.S. Appl. No. 13/624,332 Non-Final Office Action dated Oct. 3, 2017.
U.S. Appl. No. 13/624,332 Office Action dated Feb. 8, 2016.
U.S. Appl. No. 13/624,332 Office action dated Jan. 22, 2013.
U.S. Appl. No. 13/624,332 Office Action dated Jul. 18, 2016.
U.S. Appl. No. 13/624,386 Final action dated Sep. 20, 2013.
U.S. Appl. No. 13/624,386 Notice of Allowance dated Mar. 13, 2017.
U.S. Appl. No. 13/624,386 Office action dated Jan. 23, 2013.
U.S. Appl. No. 13/624,386 Office Action dated Jan. 7, 2016.
U.S. Appl. No. 13/624,386 Office Action dated Jul. 25, 2016.
U.S. Appl. No. 13/683,778 Notice of Allowance dated Nov. 24, 2014.
U.S. Appl. No. 13/683,778 Office Action dated Oct. 1, 2013.
U.S. Appl. No. 14/014,168 Final Office Action dated Sep. 18, 2017.
U.S. Appl. No. 14/014,168 Office Action dated Feb. 21, 2017.
U.S. Appl. No. 14/014,168 Office Action dated Jan. 6, 2016.
U.S. Appl. No. 14/424,022 Final Office Action dated Sep. 7, 2018.
U.S. Appl. No. 15/621,877 Non-Final Office Action dated Sep. 13, 2018.
U.S. Appl. No. 16/312,168 Non-Final Office Action dated Feb. 18, 2021.
U.S. Appl. No. 13/624,386 Office Action dated Nov. 28, 2016.
U.S. Appl. No. 14/014,168 Final Office Action dated Sep. 1, 2016.
Usami, et al. The effect of pH, hydrogen peroxide and temperature on the stability of human monoclonal antibody. J Pharm Biomed Anal. Jun. 1996;14(8-10):1133-40.
Van Der Vekiens et al., Human and equine cardiovascular endocrinology: beware to compare. Cardiovascular Endocrinology 2(4): 67-76 (2013).
Viotti et al.: Long-term cardiac outcomes of treating chronic Chagas disease with benznidazole versus no treatment: a nonrandomized trial. Ann Intern Med. 144(10): 724-734 (2006).
Viotti et al.: Side effects of benznidazole as treatment in chronic Chagas disease: fears and realities. Expert Rev Anti Infect Ther. 7(2): 157-163 (2009).
Volk, et al. The accuracy of primary care patients' self-reports of prostate-specific antigen testing. Am J Prev Med. Jan. 2002;22(1):56-8.
Wang et al., Plasma Autoantibodies Associated With Basal-like Breast Cancers. Cancer Epidemiol Biomarkers Prev24(9): 1332-1340 (2015).
Wang, Y., et al. Detection of Mammary Tumor Virus ENV Gene-like Sequences in Human Breast Cancer. (Nov. 15, 1995) Cancer Research vol. 55, pp. 5173-5179.
Waterboer et al., Dried Blood Spot Samples for Seroepidemiology of Infections With Human Papillomaviruses, Helicobacter pylori, Hepatitis C Virus, and JC Virus, Cancer, Epidemiology, Biomarkers and Prevention, 2011, 21 (2), 288-293.

(56) References Cited

OTHER PUBLICATIONS

Williams et al..Diagnosis and early detection of CNS-SLE in MRL/lpr micr using peptide microarrays. BMC Immunology 15(23): 1-19 (2014).
Yang, et al. Segmentation and intensity estimation for microarray images with saturated pixels. BMC Bioinformatics. Nov. 30, 2011;12:462. doi: 10.1186/1471-2105-12-462.
Zhou, Z.H., et al. Properties and function of polyreactive antibodies and polyreactive antigen-binding B cells. (Dec. 2007) J. Autoimmun. vol. 29, No. 4, pp. 219-228.
Zundel, et al. Development and evaluation of an enzyme-linked immunoassay for the prostate: specific antigen utilizing two monoclonal antibodies. Urol Res. 1990;18(5):327-30.
Van Bon et al.: Proteome-wide analysis and CXCL4 as a biomarker in systemic sclerosis. N Engl J Med. 370(5):433-443 (2014).
Xiang et al.: Comprehensive investigation of disease-specific short peptides in sera from patients with systemic sclerosis: complement C3f-des-arginine, detected predominantly in systemic sclerosis sera, enhances proliferation of vascular endothelial cells. Arthritis Rheum. 56(6):2018-2030 (2007).
U.S. Appl. No. 16/312,168 Final Office Action dated Mar. 30, 2022.
U.S. Appl. No. 16/312,168 Non-Final Office Action dated Sep. 15, 2021.
Zingaretti et al.: Identification of new autoantigens by protein array indicates a role for IL4 neutralization in autoimmune hepatitis. Mol Cell Proteomics. 11(12):1885-1897 doi:10.1074/mcp.M112.018713 (2012).
U.S. Appl. No. 16/312,168 Non-Final Office Action dated Nov. 18, 2022.

\* cited by examiner

FIG. 1A

Box 3: Major Clinical Manifestations of Systemic Sclerosis

Cutaneous

- Diffuse edema of hands and feet (early stages)
- Progressive skin tightening
- Sclerodactyly
- Calcinosis
- Telangiectasias
- Digital ulcers and pits
- Contractures
- Hyperpigmentation, hypopigmentation, salt and pepper skin
- Characteristic facies Vascular

- Raynaud's phenomenon
- Nailfold capillary changes
- Digital ischemia and ulcers
- Vasculitic leg ulcers (rare)

Pulmonary

- Interstitial lung disease, including alveolitis and interstitial fibrosis
- Pulmonary hypertension
- Recurrent aspiration pneumonitis caused by esophageal reflux and dysmotility
- Chest wall restriction (decreased thoracic compliance)
- Respiratory muscle weakness Cardiac

- Cardiomyopathy (systolic and diastolic dysfunction); Congestive heart failure
- Conduction defects
  - Septal infarction pattern
  - Ventricular conduction abnormalities
  - Arrhythmias
  - Heart blocks
- Pericarditis or pericardial effusion (impending renal crisis)

Renal

- Scleroderma renal crisis (hypertension, renal failure MAHA)

FIG. 1B

Musculoskeletal and Rheumatologic

- Arthralgia
- Tendon friction rubs (relatively specific for diffuse scleroderma)
- Inflammatory arthritis, erosive arthropathy (rare)
- Myopathy, myositis Gastrointestinal

- Gastroesophageal reflux
- Esophageal dysmotility, aperistaltic esophagus
- Esophageal stricture
- Adenocarcinoma arising in Barrett's esophagus (occasionally)
- Watermelon stomach (gastric antral vascular ectasias [GAVE]): Iron-deficiency anemia
- Decreased peristalsis throughout the GI tract, leading to bloating, early satiety, stasis, and pseudo-obstruction
- Bacterial overgrowth and malabsorptive diarrhea, alternating diarrhea and constipation
- Megacolon (rare)
- Colonic wide-mouth diverticuli (usually asymptomatic)
- Pneumatosis cystoides intestinales
- Primary biliary cirrhosis
- Anal incontinence Endocrine

- Hypothyroidism

Neurologic

- Carpal tunnel syndrome
- Trigeminal neuralgia

FIG. 2

Box 4: American College of Rheumatology Diagnostic Criteria for Systemic Sclerosis
Major Criterion

- Proximal sclerodermatous skin changes (proximal to the metacarpophalangeal joints)

Minor Criteria:

- Sclerodactyly
- Digital pitting scars of fingertips or loss of substance of the distal finger pads
- Bibasilar pulmonary fibrosis

| motif | n | n.lib | enrich | p | fdr | padj.holm | Pr_seqs.m | PLR |
|---|---|---|---|---|---|---|---|---|
| FAGE | 3 | 4 | 12.42717 | 2.12E-06 | 0.000155 | 0.000918 | 0.75 | 375.027 |
| KRR | 15 | 174 | 8.068678 | 2.01E-11 | 7.45E-09 | 2.23E-08 | 0.086207 | 11.7933 |
| WWY | 7 | 89 | 7.361536 | 8.66E-06 | 0.000453 | 0.009443 | 0.078652 | 10.6715 |
| KKRW | 3 | 7 | 7.101243 | 1.82E-05 | 0.000798 | 0.007816 | 0.428571 | 93.75675 |
| LKK | 8 | 107 | 6.997882 | 2.90E-06 | 0.000161 | 0.003165 | 0.074766 | 10.10174 |
| KRFF | 5 | 13 | 6.37291 | 4.26E-08 | 9.34E-06 | 1.86E-05 | 0.384615 | 78.13063 |
| ASDD | 3 | 8 | 6.213587 | 2.89E-05 | 0.000976 | 0.012372 | 0.375 | 75.0054 |
| LKSF | 3 | 8 | 6.213587 | 2.89E-05 | 0.000976 | 0.012372 | 0.375 | 75.0054 |
| WYW | 14 | 213 | 6.151894 | 3.27E-09 | 4.53E-07 | 3.60E-06 | 0.065728 | 8.794603 |
| GES | 7 | 108 | 6.066451 | 3.07E-05 | 0.001362 | 0.033318 | 0.064815 | 8.66399 |
| KKR | 18 | 283 | 5.953145 | 3.38E-11 | 9.39E-09 | 3.74E-08 | 0.063604 | 8.491177 |
| KRW | 11 | 185 | 5.565207 | 4.22E-07 | 3.35E-05 | 0.000463 | 0.059459 | 7.902868 |
| VKR | 16 | 277 | 5.406306 | 1.65E-09 | 2.90E-07 | 1.82E-06 | 0.057762 | 7.663387 |
| YWY | 10 | 174 | 5.379119 | 1.91E-06 | 0.000118 | 0.002087 | 0.057471 | 7.6225 |
| LKR | 16 | 279 | 5.367551 | 1.83E-09 | 2.90E-07 | 2.02E-06 | 0.057348 | 7.60511 |
| KRY | 12 | 215 | 5.224 | 2.52E-07 | 2.33E-05 | 0.000277 | 0.055814 | 7.389695 |
| KSF | 8 | 144 | 5.199815 | 2.57E-05 | 0.00119 | 0.027962 | 0.055556 | 7.353471 |
| YWW | 9 | 164 | 5.136402 | 8.98E-06 | 0.000453 | 0.009781 | 0.054878 | 7.258587 |
| PKAR | 3 | 10 | 4.97087 | 6.12E-05 | 0.001679 | 0.026008 | 0.3 | 53.57529 |
| WWYW | 3 | 10 | 4.97087 | 6.12E-05 | 0.001679 | 0.026008 | 0.3 | 53.57529 |
| YFY | 8 | 155 | 4.830796 | 4.35E-05 | 0.001788 | 0.047138 | 0.051613 | 6.803211 |
| AKR | 21 | 412 | 4.770704 | 5.16E-11 | 1.15E-08 | 5.71E-08 | 0.050971 | 6.714038 |
| VKKR | 4 | 14 | 4.734162 | 4.04E-06 | 0.000222 | 0.001747 | 0.285714 | 50.0036 |
| KRF | 28 | 554 | 4.730517 | 4.31E-14 | 4.79E-11 | 4.79E-11 | 0.050542 | 6.654471 |
| HKR | 13 | 264 | 4.608927 | 3.40E-07 | 2.90E-05 | 0.000374 | 0.049242 | 6.47457 |

(B)

| motif | n | n.lib | enrich | p | fdr | padj.holm | Pr_seqs.motif | PLR |
|---|---|---|---|---|---|---|---|---|
| Y | 789 | 56760 | 1.72706 | 6.29E-56 | 5.03E-55 | 5.03E-55 | 0.013901 | 1.7622 |
| K | 637 | 62082 | 1.274813 | 1.92E-13 | 7.68E-13 | 1.34E-12 | 0.010261 | 1.295968 |
| R | 630 | 63785 | 1.227142 | 1.18E-10 | 3.14E-10 | 7.06E-10 | 0.009877 | 1.247022 |
| F | 699 | 75858 | 1.14485 | 1.08E-07 | 2.17E-07 | 5.42E-07 | 0.009215 | 1.162619 |
| S | 722 | 81297 | 1.103407 | 5.54E-06 | 8.86E-06 | 2.22E-05 | 0.008881 | 1.120155 |
| W | 530 | 58364 | 1.128246 | 7.95E-05 | 0.000106 | 0.000239 | 0.009081 | 1.145602 |
| G | 922 | 111145 | 1.030656 | 0.000118 | 0.000135 | 0.000239 | 0.008295 | 1.045683 |
| A | 518 | 57451 | 1.120224 | 0.000193 | 0.000193 | 0.000239 | 0.009016 | 1.137384 |

| motif | n | n.lib | enrich | p | fdr | padj.holm | Pr_seqs | PLR |
|---|---|---|---|---|---|---|---|---|
| YDEK | 2 | 2 | 17.8669 | 5.49E-05 | 0.0018 | 0.01575 | 1 | Inf |
| PVRR | 2 | 3 | 11.9112 | 0.00016 | 0.00284 | 0.04571 | 0.66667 | 250.018 |
| SNPV | 3 | 5 | 10.7201 | 4.02E-06 | 0.00047 | 0.00118 | 0.6 | 187.514 |
| DKYE | 3 | 6 | 8.93343 | 8.00E-06 | 0.00047 | 0.00234 | 0.5 | 125.009 |
| DVHY | 3 | 6 | 8.93343 | 8.00E-06 | 0.00047 | 0.00234 | 0.5 | 125.009 |
| NPDQ | 3 | 6 | 8.93343 | 8.00E-06 | 0.00047 | 0.00234 | 0.5 | 125.009 |
| QEEF | 3 | 7 | 7.65723 | 1.39E-05 | 0.00068 | 0.00404 | 0.42857 | 93.7568 |
| NPE | 10 | 134 | 7.47587 | 8.59E-08 | 9.65E-05 | 9.65E-05 | 0.07463 | 10.0814 |
| DEV | 7 | 103 | 6.80812 | 1.39E-05 | 0.00312 | 0.01552 | 0.06796 | 9.11524 |
| EDWP | 4 | 11 | 6.49704 | 9.53E-07 | 0.00028 | 0.00028 | 0.36364 | 71.4337 |
| EDFP | 3 | 10 | 5.36006 | 4.69E-05 | 0.00173 | 0.01351 | 0.3 | 53.5753 |
| PLVD | 3 | 11 | 4.87278 | 6.42E-05 | 0.00189 | 0.01835 | 0.27273 | 46.8784 |
| SPD | 9 | 186 | 4.84726 | 1.35E-05 | 0.00312 | 0.01508 | 0.04839 | 6.35639 |
| LVD | 10 | 216 | 4.63781 | 6.68E-06 | 0.0025 | 0.00748 | 0.0463 | 6.0684 |
| LRDP | 3 | 12 | 4.46672 | 8.51E-05 | 0.00193 | 0.02424 | 0.25 | 41.6697 |
| PARR | 3 | 12 | 4.46672 | 8.51E-05 | 0.00193 | 0.02424 | 0.25 | 41.6697 |
| PELE | 3 | 12 | 4.46672 | 8.51E-05 | 0.00193 | 0.02424 | 0.25 | 41.6697 |
| PEYK | 3 | 13 | 4.12312 | 0.00011 | 0.00232 | 0.03101 | 0.23077 | 37.5027 |
| VVVS | 3 | 14 | 3.82861 | 0.00014 | 0.00257 | 0.03911 | 0.21429 | 34.0934 |
| YDPV | 3 | 14 | 3.82861 | 0.00014 | 0.00257 | 0.03911 | 0.21429 | 34.0934 |
| DPA | 11 | 303 | 3.63678 | 2.29E-05 | 0.0043 | 0.02566 | 0.0363 | 4.70924 |
| E.P | 51 | 2430 | 2.80423 | 1.49E-10 | 1.77E-08 | 1.77E-08 | 0.02099 | 2.67989 |
| D..P | 39 | 2129 | 2.46511 | 6.03E-07 | 1.76E-05 | 6.88E-05 | 0.01832 | 2.3327 |
| PE | 58 | 3143 | 2.44722 | 1.40E-09 | 1.69E-07 | 1.69E-07 | 0.01845 | 2.35025 |
| D...P | 25 | 1399 | 2.44005 | 9.29E-05 | 0.00391 | 0.01032 | 0.01787 | 2.27455 |

(B)

| motif | n | n.lib | enrich | p | fdr | padj.holm | Pr_seqs | PLR |
|---|---|---|---|---|---|---|---|---|
| D | 969 | 98037 | 1.30318 | 6.37E-27 | 5.10E-26 | 5.10E-26 | 0.00988 | 1.24793 |
| E | 867 | 88289 | 1.29474 | 2.48E-22 | 9.92E-22 | 1.74E-21 | 0.00982 | 1.23977 |
| P | 538 | 56321 | 1.25945 | 1.77E-10 | 4.71E-10 | 1.06E-09 | 0.00955 | 1.20565 |
| V | 564 | 68411 | 1.08699 | 0.00065 | 0.00104 | 0.00259 | 0.00824 | 1.03918 |
| G | 903 | 1E+05 | 1.07119 | 6.01E-07 | 1.20E-06 | 3.00E-06 | 0.00812 | 1.02396 |
| S | 633 | 81297 | 1.0266 | 0.0144 | 0.01921 | 0.04321 | 0.00779 | 0.98099 |

| motif | n | n.lib | enrich | p | fdr | padj.holm | Pr_seqs.m | PLR |
|---|---|---|---|---|---|---|---|---|
| DGLH | 2 | 4 | 9.317495 | 0.000105 | 0.000984 | 0.009979 | 0.5 | 251.018 |
| NPGS | 2 | 4 | 9.317495 | 0.000105 | 0.000984 | 0.009979 | 0.5 | 251.018 |
| NPHP | 2 | 4 | 9.317495 | 0.000105 | 0.000984 | 0.009979 | 0.5 | 251.018 |
| PLN | 7 | 123 | 7.922963 | 1.00E-06 | 0.000385 | 0.000655 | 0.056911 | 15.14764 |
| PEV | 7 | 126 | 7.734321 | 1.18E-06 | 0.000385 | 0.000769 | 0.055556 | 14.76576 |
| PESQ | 2 | 5 | 7.453996 | 0.000175 | 0.001199 | 0.016061 | 0.4 | 167.3453 |
| PFHP | 2 | 5 | 7.453996 | 0.000175 | 0.001199 | 0.016061 | 0.4 | 167.3453 |
| PFLP | 2 | 5 | 7.453996 | 0.000175 | 0.001199 | 0.016061 | 0.4 | 167.3453 |
| VESV | 2 | 5 | 7.453996 | 0.000175 | 0.001199 | 0.016061 | 0.4 | 167.3453 |
| P.....P | 26 | 782 | 7.169625 | 5.44E-15 | 2.64E-13 | 5.22E-13 | 0.033248 | 8.632894 |
| PVES | 3 | 9 | 6.211664 | 6.09E-06 | 0.000408 | 0.000627 | 0.333333 | 125.509 |
| PEVA | 2 | 6 | 6.211664 | 0.000261 | 0.001281 | 0.022718 | 0.333333 | 125.509 |
| PQDK | 2 | 6 | 6.211664 | 0.000261 | 0.001281 | 0.022718 | 0.333333 | 125.509 |
| PWDQ | 2 | 6 | 6.211664 | 0.000261 | 0.001281 | 0.022718 | 0.333333 | 125.509 |
| PYEV | 2 | 6 | 6.211664 | 0.000261 | 0.001281 | 0.022718 | 0.333333 | 125.509 |
| WELP | 2 | 6 | 6.211664 | 0.000261 | 0.001281 | 0.022718 | 0.333333 | 125.509 |
| P....P | 29 | 1155 | 5.717851 | 9.99E-14 | 1.90E-12 | 9.09E-12 | 0.025108 | 6.46494 |
| YHDS | 3 | 10 | 5.590497 | 8.67E-06 | 0.000408 | 0.000884 | 0.3 | 107.5791 |
| P.....A | 20 | 798 | 5.404518 | 9.77E-10 | 1.35E-08 | 8.89E-08 | 0.025063 | 6.452905 |
| ANYP | 2 | 7 | 5.324283 | 0.000365 | 0.001391 | 0.029894 | 0.285714 | 100.4072 |
| EVYH | 2 | 7 | 5.324283 | 0.000365 | 0.001391 | 0.029894 | 0.285714 | 100.4072 |
| PDAE | 2 | 7 | 5.324283 | 0.000365 | 0.001391 | 0.029894 | 0.285714 | 100.4072 |
| PDRD | 2 | 7 | 5.324283 | 0.000365 | 0.001391 | 0.029894 | 0.285714 | 100.4072 |
| PLNE | 2 | 7 | 5.324283 | 0.000365 | 0.001391 | 0.029894 | 0.285714 | 100.4072 |
| YRND | 2 | 7 | 5.324283 | 0.000365 | 0.001391 | 0.029894 | 0.285714 | 100.4072 |

(B)

| motif | n | n.lib | enrich | p | fdr | padj.holm | Pr_seqs.motif | PLR |
|---|---|---|---|---|---|---|---|---|
| P | 600 | 56321 | 2.585501 | 1.36275467947878E-105 | 9.53928275635149E-105 | 9.53928275635149E-105 | 0.010653 | 2.702945 |
| D | 532 | 98037 | 1.316999 | 2.40E-16 | 8.40E-16 | 1.44E-15 | 0.005427 | 1.369587 |
| E | 444 | 88289 | 1.220507 | 7.36E-09 | 1.72E-08 | 3.68E-08 | 0.005029 | 1.268735 |

| motif | n | n.lib | enrich | p | fdr | padj.holm | Pr_seqs.m | PLR |
|---|---|---|---|---|---|---|---|---|
| HHAP | 2 | 2 | 18.02843 | 1.63E-05 | 0.000512 | 0.002497 | 1 | Inf |
| RYY | 9 | 90 | 13.07211 | 1.46E-10 | 2.92E-08 | 8.74E-08 | 0.1 | 27.89089 |
| RVWW | 2 | 3 | 12.01895 | 4.88E-05 | 0.000958 | 0.007325 | 0.666667 | 502.036 |
| RRY | 9 | 99 | 11.88373 | 3.47E-10 | 5.03E-08 | 2.07E-07 | 0.090909 | 25.1018 |
| RYR | 13 | 183 | 9.286196 | 1.03E-12 | 6.16E-10 | 6.16E-10 | 0.071038 | 19.19549 |
| LGNW | 2 | 4 | 9.014216 | 9.74E-05 | 0.001495 | 0.014513 | 0.5 | 251.018 |
| PYYY | 2 | 4 | 9.014216 | 9.74E-05 | 0.001495 | 0.014513 | 0.5 | 251.018 |
| RY | 99 | 2725 | 8.902886 | 1.35E-59 | 1.28E-57 | 1.28E-57 | 0.03633 | 9.463359 |
| RYK | 11 | 190 | 7.568062 | 5.03E-10 | 5.03E-08 | 3E-07 | 0.057895 | 15.42569 |
| GHRY | 2 | 5 | 7.211373 | 0.000162 | 0.001495 | 0.023637 | 0.4 | 167.3453 |
| RRLV | 2 | 5 | 7.211373 | 0.000162 | 0.001495 | 0.023637 | 0.4 | 167.3453 |
| RYRW | 2 | 5 | 7.211373 | 0.000162 | 0.001495 | 0.023637 | 0.4 | 167.3453 |
| RYSW | 2 | 5 | 7.211373 | 0.000162 | 0.001495 | 0.023637 | 0.4 | 167.3453 |
| VRYR | 2 | 5 | 7.211373 | 0.000162 | 0.001495 | 0.023637 | 0.4 | 167.3453 |
| YRRN | 2 | 5 | 7.211373 | 0.000162 | 0.001495 | 0.023637 | 0.4 | 167.3453 |
| RYH | 9 | 164 | 7.173717 | 3E-08 | 2.57E-06 | 1.78E-05 | 0.054878 | 14.57524 |
| HRY | 6 | 110 | 7.13024 | 6.39E-06 | 0.000239 | 0.003742 | 0.054545 | 14.48181 |
| SRY | 6 | 110 | 7.13024 | 6.39E-06 | 0.000239 | 0.003742 | 0.054545 | 14.48181 |
| R....Y | 31 | 1090 | 6.85769 | 1.16E-16 | 1.17E-14 | 1.17E-14 | 0.02844 | 7.348025 |
| RYHY | 3 | 8 | 6.760662 | 3.64E-06 | 0.00019 | 0.000563 | 0.375 | 150.6108 |
| VRY | 6 | 121 | 6.482036 | 1.1E-05 | 0.000331 | 0.006411 | 0.049587 | 13.09659 |
| R..Y | 52 | 1963 | 6.439458 | 1.22E-25 | 1.27E-23 | 1.27E-23 | 0.02649 | 6.830422 |
| YVR | 6 | 125 | 6.274611 | 1.33E-05 | 0.00038 | 0.007704 | 0.048 | 12.65637 |
| RYG | 7 | 146 | 6.267448 | 2.55E-06 | 0.000128 | 0.001503 | 0.047945 | 12.64119 |
| YKY | 7 | 152 | 6.020049 | 3.33E-06 | 0.000154 | 0.00196 | 0.046053 | 12.11811 |

(B)

| motif | n | n.lib | enrich | p | fdr | padj.holm | Pr_seqs.motif | PLR |
|---|---|---|---|---|---|---|---|---|
| R | 598 | 63785 | 2.33422 | 3.84E-89 | 2.31E-88 | 2.31E-88 | 0.009375 | 2.375627 |
| Y | 457 | 56760 | 2.004624 | 9.22E-49 | 2.77E-48 | 4.61E-48 | 0.008051 | 2.037462 |
| S | 436 | 81297 | 1.335276 | 1.84E-13 | 3.68E-13 | 7.36E-13 | 0.005363 | 1.353481 |
| H | 348 | 65939 | 1.314002 | 1.55E-09 | 2.32E-09 | 4.64E-09 | 0.005278 | 1.331803 |
| K | 304 | 62082 | 1.219178 | 1.33E-05 | 1.60E-05 | 2.66E-05 | 0.004897 | 1.235221 |
| F | 329 | 75858 | 1.079826 | 0.009229 | 0.009229 | 0.009229 | 0.004337 | 1.09342 |

| motif | n | n.lib | enrich | p | fdr | padj.holm | Pr_seqs.m | PLR |
|---|---|---|---|---|---|---|---|---|
| GFVQ | 2 | 2 | 17.46913 | 5.63E-05 | 0.001593 | 0.017016 | 1 | Inf |
| PPFR | 2 | 2 | 17.46913 | 5.63E-05 | 0.001593 | 0.017016 | 1 | Inf |
| LRYG | 3 | 4 | 13.10185 | 1.68E-06 | 0.000262 | 0.000521 | 0.75 | 375.027 |
| PPRN | 2 | 3 | 11.64609 | 0.000168 | 0.003077 | 0.04995 | 0.666667 | 250.018 |
| PVRR | 2 | 3 | 11.64609 | 0.000168 | 0.003077 | 0.04995 | 0.666667 | 250.018 |
| YYYD | 2 | 3 | 11.64609 | 0.000168 | 0.003077 | 0.04995 | 0.666667 | 250.018 |
| PPR | 14 | 130 | 10.80912 | 1.92E-12 | 2.17E-09 | 2.17E-09 | 0.107692 | 15.08729 |
| VRR | 9 | 95 | 9.508773 | 5.30E-08 | 1.50E-05 | 5.98E-05 | 0.094737 | 13.08234 |
| YDEY | 3 | 6 | 8.734565 | 8.31E-06 | 0.000862 | 0.002569 | 0.5 | 125.009 |
| YYD | 10 | 124 | 8.094386 | 4.56E-08 | 1.50E-05 | 5.15E-05 | 0.080645 | 10.9657 |
| SYEE | 3 | 7 | 7.48677 | 1.45E-05 | 0.001066 | 0.004456 | 0.428571 | 93.75675 |
| RRS | 12 | 193 | 6.240645 | 3.89E-08 | 1.50E-05 | 4.39E-05 | 0.062176 | 8.28789 |
| LRY | 7 | 115 | 6.109501 | 3.04E-05 | 0.00357 | 0.034206 | 0.06087 | 8.102435 |
| PARR | 4 | 12 | 5.823043 | 1.50E-06 | 0.000262 | 0.000465 | 0.333333 | 62.5045 |
| EKKD | 3 | 9 | 5.823043 | 3.43E-05 | 0.001222 | 0.010472 | 0.333333 | 62.5045 |
| RNYA | 3 | 9 | 5.823043 | 3.43E-05 | 0.001222 | 0.010472 | 0.333333 | 62.5045 |
| RYG | 8 | 146 | 5.499747 | 1.79E-05 | 0.002707 | 0.02014 | 0.054795 | 7.246899 |
| DDY | 8 | 158 | 5.082045 | 3.15E-05 | 0.00357 | 0.035413 | 0.050633 | 6.667147 |
| ARSQ | 3 | 11 | 4.764308 | 6.67E-05 | 0.001728 | 0.020006 | 0.272727 | 46.87838 |
| NEVD | 3 | 12 | 4.367282 | 8.84E-05 | 0.002115 | 0.026436 | 0.25 | 41.66967 |
| SYA | 11 | 290 | 3.807152 | 1.70E-05 | 0.002707 | 0.019134 | 0.037931 | 4.92867 |
| YSG | 17 | 457 | 3.73369 | 1.28E-07 | 2.90E-05 | 0.000144 | 0.037199 | 4.829893 |
| SGLF | 4 | 21 | 3.327453 | 1.71E-05 | 0.001066 | 0.005262 | 0.190476 | 29.41388 |
| R....G | 98 | 4448 | 3.021096 | 2.99E-21 | 3.08E-19 | 3.08E-19 | 0.022032 | 2.816295 |
| QRS | 14 | 469 | 2.996131 | 1.91E-05 | 0.002707 | 0.021521 | 0.029851 | 3.846431 |

(B)

| motif | n | n.lib | enrich | p | fdr | padj.holm | Pr_seqs.motif | PLR |
|---|---|---|---|---|---|---|---|---|
| S | 882 | 81297 | 1.418235 | 6.13E-34 | 4.29E-33 | 4.29E-33 | 0.010849 | 1.371112 |
| G | 1027 | 111145 | 1.20791 | 7.53E-20 | 2.63E-19 | 4.52E-19 | 0.00924 | 1.165879 |
| Y | 568 | 56760 | 1.308158 | 1.15E-13 | 2.68E-13 | 5.75E-13 | 0.010007 | 1.263616 |
| R | 620 | 63785 | 1.270654 | 4.72E-13 | 8.27E-13 | 1.89E-12 | 0.00972 | 1.227034 |
| A | 487 | 57451 | 1.108117 | 0.000749 | 0.001048 | 0.002246 | 0.008477 | 1.068734 |
| Q | 491 | 60519 | 1.060581 | 0.013081 | 0.014598 | 0.026162 | 0.008113 | 1.022513 |
| V | 547 | 68411 | 1.045239 | 0.014598 | 0.014598 | 0.026162 | 0.007996 | 1.007602 |

| motif | n | n.lib | enrich | p | fdr | padj.holm | Pr_seqs.m | PLR |
|---|---|---|---|---|---|---|---|---|
| DEHH | 2 | 2 | 18.06433 | 6.44E-05 | 0.002268 | 0.021124 | 1 | Inf |
| PPFR | 2 | 2 | 18.06433 | 6.44E-05 | 0.002268 | 0.021124 | 1 | Inf |
| VDDH | 3 | 4 | 13.54825 | 2.05E-06 | 0.000344 | 0.000686 | 0.75 | 375.027 |
| PVRQ | 3 | 5 | 10.8386 | 5.11E-06 | 0.00057 | 0.0017 | 0.6 | 187.5135 |
| PLRR | 3 | 6 | 9.032165 | 1.01E-05 | 0.00085 | 0.003369 | 0.5 | 125.009 |
| VDE | 14 | 156 | 8.797687 | 4.88E-11 | 5.79E-08 | 5.79E-08 | 0.089744 | 12.32483 |
| PRR | 11 | 132 | 8.16928 | 1.23E-08 | 4.89E-06 | 1.46E-05 | 0.083333 | 11.36445 |
| DDH | 9 | 108 | 8.16928 | 2.60E-07 | 6.17E-05 | 0.000307 | 0.083333 | 11.36445 |
| PVR | 10 | 124 | 7.905755 | 7.71E-08 | 2.29E-05 | 9.14E-05 | 0.080645 | 10.9657 |
| DYYG | 4 | 10 | 7.225732 | 8.37E-07 | 0.000281 | 0.000281 | 0.4 | 83.33933 |
| DEH | 9 | 125 | 7.058258 | 8.98E-07 | 0.000152 | 0.001062 | 0.072 | 9.698974 |
| PRN | 9 | 125 | 7.058258 | 8.98E-07 | 0.000152 | 0.001062 | 0.072 | 9.698974 |
| PPR | 9 | 130 | 6.786787 | 1.25E-06 | 0.000165 | 0.001472 | 0.069231 | 9.29819 |
| PRK | 8 | 121 | 6.481413 | 6.82E-06 | 0.000737 | 0.008034 | 0.066116 | 8.850195 |
| EEH | 7 | 112 | 6.12696 | 3.68E-05 | 0.002912 | 0.043159 | 0.0625 | 8.333933 |
| HPDE | 3 | 9 | 6.021443 | 4.19E-05 | 0.002268 | 0.013856 | 0.333333 | 62.5045 |
| PPRK | 3 | 9 | 6.021443 | 4.19E-05 | 0.002268 | 0.013856 | 0.333333 | 62.5045 |
| NPE | 8 | 134 | 5.852619 | 1.44E-05 | 0.001426 | 0.016958 | 0.059701 | 7.937079 |
| HFP | 14 | 236 | 5.81542 | 1.09E-08 | 4.89E-06 | 1.29E-05 | 0.059322 | 7.88345 |
| VDD | 8 | 137 | 5.724459 | 1.69E-05 | 0.001546 | 0.019897 | 0.058394 | 7.752496 |
| KHVR | 3 | 10 | 5.419299 | 5.94E-05 | 0.002268 | 0.019557 | 0.3 | 53.57529 |
| RNH | 11 | 208 | 5.184351 | 1.24E-06 | 0.000165 | 0.001459 | 0.052885 | 6.980198 |
| EEHS | 3 | 11 | 4.926636 | 8.12E-05 | 0.002268 | 0.026485 | 0.272727 | 46.87838 |
| PRNR | 3 | 11 | 4.926636 | 8.12E-05 | 0.002268 | 0.026485 | 0.272727 | 46.87838 |
| RAYK | 3 | 11 | 4.926636 | 8.12E-05 | 0.002268 | 0.026485 | 0.272727 | 46.87838 |

(B)

| motif | n | n.lib | enrich | p | fdr | padj.holm | Pr_seqs.motif | PLR |
|---|---|---|---|---|---|---|---|---|
| P | 697 | 56321 | 1.547734 | 1.55E-34 | 7.74E-34 | 7.74E-34 | 0.012375 | 1.566433 |
| R | 722 | 63785 | 1.415639 | 1.03E-25 | 2.57E-25 | 4.11E-25 | 0.011319 | 1.431212 |
| K | 633 | 62082 | 1.275181 | 1.94E-13 | 3.23E-13 | 5.82E-13 | 0.010196 | 1.287746 |
| H | 649 | 65939 | 1.230938 | 2.56E-11 | 3.21E-11 | 5.13E-11 | 0.009842 | 1.242623 |
| D | 805 | 98037 | 1.026927 | 0.001503 | 0.001503 | 0.001503 | 0.008211 | 1.03497 |

| motif | n | n.lib | enrich | p | fdr | padj.holm | Pr_seqs.m | PLR |
|---|---|---|---|---|---|---|---|---|
| RWYY | 2 | 2 | 16.77991 | 6.39E-05 | 0.001788 | 0.025988 | 1 | Inf |
| VWWW | 2 | 2 | 16.77991 | 6.39E-05 | 0.001788 | 0.025988 | 1 | Inf |
| GES | 10 | 108 | 8.576619 | 1.99E-08 | 4.59E-06 | 2.17E-05 | 0.092593 | 12.75602 |
| YGE | 11 | 122 | 8.351658 | 5.19E-09 | 1.89E-06 | 5.66E-06 | 0.090164 | 12.38828 |
| KKRW | 3 | 7 | 7.191389 | 1.74E-05 | 0.001046 | 0.007216 | 0.428571 | 93.75675 |
| ASDD | 3 | 8 | 6.292465 | 2.77E-05 | 0.001294 | 0.011449 | 0.375 | 75.0054 |
| YWGN | 3 | 8 | 6.292465 | 2.77E-05 | 0.001294 | 0.011449 | 0.375 | 75.0054 |
| KDE | 9 | 135 | 6.175165 | 1.66E-06 | 0.000199 | 0.0018 | 0.066667 | 8.929214 |
| WYW | 12 | 213 | 5.21845 | 2.01E-07 | 3.14E-05 | 0.000218 | 0.056338 | 7.463224 |
| NFW | 8 | 143 | 5.181957 | 2.25E-05 | 0.001637 | 0.024241 | 0.055944 | 7.407941 |
| KRFF | 4 | 13 | 5.163048 | 2.75E-06 | 0.000231 | 0.001144 | 0.307692 | 55.55956 |
| YWW | 9 | 164 | 5.083215 | 8.16E-06 | 0.000743 | 0.008832 | 0.054878 | 7.258587 |
| ASEE | 3 | 11 | 4.576338 | 8.02E-05 | 0.001982 | 0.03249 | 0.272727 | 46.87838 |
| SDSY | 3 | 11 | 4.576338 | 8.02E-05 | 0.001982 | 0.03249 | 0.272727 | 46.87838 |
| QRSQ | 3 | 12 | 4.194977 | 0.000106 | 0.00235 | 0.042848 | 0.25 | 41.66967 |
| WFPH | 3 | 12 | 4.194977 | 0.000106 | 0.00235 | 0.042848 | 0.25 | 41.66967 |
| GYG | 10 | 222 | 4.172409 | 1.47E-05 | 0.001148 | 0.015887 | 0.045045 | 5.896651 |
| ESD | 17 | 382 | 4.122165 | 2.10E-08 | 4.59E-06 | 2.29E-05 | 0.044503 | 5.822337 |
| SED | 55 | 1344 | 3.790559 | 4.03E-22 | 4.41E-19 | 4.41E-19 | 0.040923 | 5.333976 |
| DED | 23 | 570 | 3.7376 | 4.96E-10 | 2.71E-07 | 5.42E-07 | 0.040351 | 5.25632 |
| GSE | 17 | 436 | 3.611622 | 1.39E-07 | 2.53E-05 | 0.000151 | 0.038991 | 5.071964 |
| W..W | 63 | 2236 | 3.525676 | 4.34E-17 | 4.47E-15 | 4.47E-15 | 0.028175 | 3.624283 |
| SSE | 17 | 455 | 3.460807 | 2.52E-07 | 3.44E-05 | 0.000274 | 0.037363 | 4.851947 |
| WY | 66 | 2413 | 3.42858 | 3.30E-17 | 1.82E-15 | 3.60E-15 | 0.027352 | 3.515379 |
| EED | 16 | 469 | 3.159999 | 1.82E-06 | 0.000199 | 0.001972 | 0.034115 | 4.415329 |

(B)

| motif | n | n.lib | enrich | p | fdr | padj.holm | Pr_seqs.motif | PLR |
|---|---|---|---|---|---|---|---|---|
| Y | 745 | 56760 | 1.646241 | 1.74E-45 | 1.22E-44 | 1.22E-44 | 0.013125 | 1.662621 |
| W | 637 | 58364 | 1.368907 | 3.44E-19 | 1.20E-18 | 2.06E-18 | 0.010914 | 1.379437 |
| S | 790 | 81297 | 1.218799 | 7.02E-14 | 1.64E-13 | 3.51E-13 | 0.009717 | 1.22669 |
| G | 954 | 111145 | 1.076559 | 1.32E-07 | 2.30E-07 | 5.27E-07 | 0.008583 | 1.08229 |
| D | 836 | 98037 | 1.069537 | 9.54E-06 | 1.34E-05 | 2.86E-05 | 0.008527 | 1.075169 |
| F | 630 | 75858 | 1.041642 | 0.006944 | 0.008101 | 0.013888 | 0.008305 | 1.046893 |

| motif | n | n.lib | enrich | p | fdr | padj.holm | Pr_seqs. | PLR |
|---|---|---|---|---|---|---|---|---|
| SAY | 8 | 111 | 7.15427 | 3.25E-06 | 0.00334 | 0.00399 | 0.07207 | 9.70944 |
| RQYQ | 3 | 8 | 6.87164 | 2.68E-05 | 0.00425 | 0.00776 | 0.375 | 75.0054 |
| SAYE | 3 | 10 | 5.49731 | 5.67E-05 | 0.00425 | 0.01638 | 0.3 | 53.5753 |
| HEH | 8 | 146 | 5.4392 | 2.43E-05 | 0.00994 | 0.02978 | 0.05479 | 7.2469 |
| HVEV | 3 | 11 | 4.99755 | 7.75E-05 | 0.00425 | 0.02216 | 0.27273 | 46.8784 |
| DKS | 10 | 200 | 4.96327 | 5.43E-06 | 0.00334 | 0.00667 | 0.05 | 6.57942 |
| NHNV | 3 | 12 | 4.58109 | 0.0001 | 0.00425 | 0.02916 | 0.25 | 41.6697 |
| R....W | 18 | 737 | 3.06844 | 3.19E-05 | 0.00094 | 0.00366 | 0.02442 | 3.12957 |
| H....V | 30 | 1351 | 2.78984 | 6.49E-07 | 7.47E-05 | 7.66E-05 | 0.02221 | 2.83896 |
| DYWK | 4 | 27 | 2.71472 | 5.90E-05 | 0.00425 | 0.01699 | 0.14815 | 21.7407 |
| H....V | 32 | 1548 | 2.59712 | 1.27E-06 | 7.47E-05 | 0.00015 | 0.02067 | 2.63871 |
| H....V | 35 | 1787 | 2.47512 | 2.23E-06 | 0.00028 | 0.00028 | 0.01959 | 2.49733 |
| DKSG | 4 | 30 | 2.44325 | 9.04E-05 | 0.00425 | 0.02576 | 0.13333 | 19.2322 |
| HH | 47 | 2453 | 2.42312 | 6.52E-08 | 8.02E-06 | 8.02E-06 | 0.01916 | 2.44199 |
| H...V | 42 | 2221 | 2.39673 | 3.99E-07 | 3.31E-05 | 5.39E-05 | 0.01891 | 2.40954 |
| H....V | 34 | 1803 | 2.36917 | 4.95E-06 | 0.00019 | 0.00057 | 0.01886 | 2.40266 |
| H....V | 22 | 1189 | 2.33826 | 0.00035 | 0.01102 | 0.04304 | 0.0185 | 2.35664 |
| S.Y | 47 | 2555 | 2.32759 | 2.24E-07 | 3.04E-05 | 3.04E-05 | 0.0184 | 2.34267 |
| K....V | 23 | 1271 | 2.28684 | 0.00031 | 0.01102 | 0.03855 | 0.0181 | 2.30385 |
| EK | 50 | 2803 | 2.25591 | 2.61E-07 | 1.61E-05 | 3.19E-05 | 0.01784 | 2.27041 |
| H...F | 48 | 2708 | 2.24652 | 4.91E-07 | 3.31E-05 | 6.58E-05 | 0.01773 | 2.2558 |
| DK | 49 | 2835 | 2.18583 | 1.02E-06 | 4.18E-05 | 0.00012 | 0.01728 | 2.19865 |
| SS | 46 | 2662 | 2.18536 | 1.56E-06 | 4.78E-05 | 0.00019 | 0.01728 | 2.19817 |
| S..R | 40 | 2436 | 2.07913 | 2.52E-05 | 0.00165 | 0.00313 | 0.01642 | 2.08696 |
| H...Q | 29 | 1773 | 2.07304 | 0.00035 | 0.01187 | 0.04642 | 0.01636 | 2.0787 |

(B)

| motif | n | n.lib | enrich | p | fdr | padj.holm | Pr_seqs. | PLR |
|---|---|---|---|---|---|---|---|---|
| K | 578 | 62082 | 1.17696 | 2.14E-07 | 1.07E-06 | 1.93E-06 | 0.00931 | 1.1748 |
| H | 606 | 65939 | 1.1618 | 3.92E-07 | 1.31E-06 | 3.14E-06 | 0.00919 | 1.15953 |
| S | 728 | 81297 | 1.13203 | 1.43E-07 | 1.07E-06 | 1.43E-06 | 0.00895 | 1.12955 |
| R | 567 | 63785 | 1.12373 | 4.01E-05 | 0.0001 | 0.00028 | 0.00889 | 1.1212 |
| Q | 522 | 60519 | 1.09038 | 0.00142 | 0.00237 | 0.00711 | 0.00863 | 1.08763 |
| A | 487 | 57451 | 1.0716 | 0.00813 | 0.01161 | 0.03251 | 0.00848 | 1.06873 |
| G | 897 | 1E+05 | 1.02024 | 0.00048 | 0.00095 | 0.00286 | 0.00807 | 1.0171 |

| motif | n | n.lib | enrich | p | fdr | padj.holm | Pr_seqs.motif | PLR |
|---|---|---|---|---|---|---|---|---|
| PDLQ | 2 | 2 | 15.90948 | 6.82E-05 | 0.001545 | 0.026925 | 1 | Inf |
| PDSV | 2 | 2 | 15.90948 | 6.82E-05 | 0.001545 | 0.026925 | 1 | Inf |
| PDVV | 2 | 2 | 15.90948 | 6.82E-05 | 0.001545 | 0.026925 | 1 | Inf |
| PERA | 2 | 2 | 15.90948 | 6.82E-05 | 0.001545 | 0.026925 | 1 | Inf |
| PGSL | 2 | 2 | 15.90948 | 6.82E-05 | 0.001545 | 0.026925 | 1 | Inf |
| PGD | 16 | 111 | 12.94505 | 1.64E-15 | 5.86E-13 | 1.76E-12 | 0.144144 | 21.05415 |
| PDS | 17 | 119 | 12.82947 | 2.54E-16 | 2.72E-13 | 2.72E-13 | 0.142857 | 20.83483 |
| PQES | 4 | 5 | 12.72759 | 2.31E-08 | 9.41E-06 | 9.41E-06 | 0.8 | 500.036 |
| PDD | 15 | 112 | 12.02763 | 3.81E-14 | 8.16E-12 | 4.07E-11 | 0.133929 | 19.33129 |
| PDH | 17 | 127 | 12.02131 | 7.80E-16 | 4.18E-13 | 8.36E-13 | 0.133858 | 19.31957 |
| PPE | 16 | 127 | 11.31418 | 1.45E-14 | 3.89E-12 | 1.55E-11 | 0.125984 | 18.01932 |
| PEE | 15 | 124 | 10.86366 | 1.76E-13 | 2.36E-11 | 1.88E-10 | 0.120968 | 17.20307 |
| P.....A | 75 | 798 | 10.40835 | 4.10E-52 | 2.50E-50 | 2.50E-50 | 0.093985 | 12.96774 |
| PGE | 14 | 122 | 10.30564 | 2.33E-12 | 2.50E-10 | 2.48E-09 | 0.114754 | 16.20487 |
| PEQ | 13 | 115 | 10.15202 | 1.71E-11 | 1.53E-09 | 1.81E-08 | 0.113043 | 15.93252 |
| PPD | 14 | 127 | 9.899906 | 4.07E-12 | 3.96E-10 | 4.32E-09 | 0.110236 | 15.48784 |
| PGS | 13 | 121 | 9.648609 | 3.28E-11 | 2.35E-09 | 3.47E-08 | 0.107438 | 15.04738 |
| PDHQ | 3 | 5 | 9.54569 | 5.56E-06 | 0.000756 | 0.002256 | 0.6 | 187.5135 |
| PDA | 17 | 167 | 9.141957 | 7.94E-14 | 1.42E-11 | 8.47E-11 | 0.101796 | 14.16769 |
| PEH | 13 | 129 | 9.050246 | 7.41E-11 | 4.96E-09 | 7.83E-08 | 0.100775 | 14.00963 |
| PDV | 11 | 111 | 8.899722 | 2.53E-09 | 1.08E-07 | 2.65E-06 | 0.099099 | 13.75099 |
| PDR | 12 | 122 | 8.833405 | 5.24E-10 | 2.96E-08 | 5.53E-07 | 0.098361 | 13.63735 |
| P.....Q | 75 | 954 | 8.706356 | 1.31E-46 | 4.00E-45 | 7.86E-45 | 0.078616 | 10.6663 |
| PDE | 12 | 124 | 8.690931 | 6.34E-10 | 3.23E-08 | 6.67E-07 | 0.096774 | 13.39382 |
| PDL | 12 | 124 | 8.690931 | 6.34E-10 | 3.23E-08 | 6.67E-07 | 0.096774 | 13.39382 |

(B)

| motif | n | n.lib | enrich | p | fdr | padj.holm | Pr_seqs.motif | PLR |
|---|---|---|---|---|---|---|---|---|
| P | 1406 | 56321 | 3.063067 | 2.9149873 | 2.0404911 | 2.0404911 | 0.024964 | 3.200631 |
| E | 901 | 88289 | 1.25216 | 3.57E-19 | 1.25E-18 | 2.14E-18 | 0.010205 | 1.288885 |
| D | 942 | 98037 | 1.178969 | 2.06E-14 | 4.82E-14 | 1.03E-13 | 0.009609 | 1.212817 |
| S | 785 | 81297 | 1.184777 | 2.18E-11 | 3.82E-11 | 8.73E-11 | 0.009656 | 1.21885 |
| G | 953 | 111145 | 1.05207 | 5.13E-06 | 7.19E-06 | 1.54E-05 | 0.008574 | 1.081145 |
| Q | 526 | 60519 | 1.066438 | 0.007134 | 0.008323 | 0.014268 | 0.008691 | 1.09604 |

SSc seropositive vs. SSc seronegative

SSC GAVE+ vs. SSC GAVE- peptides

SEQUENCE LISTING

```
<160> NUMBER OF SEQ ID NOS: 99

<210> SEQ ID NO 1
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 1

Phe Ala Gly Glu
1

<210> SEQ ID NO 2
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 2

Lys Lys Arg Trp
1

<210> SEQ ID NO 3
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 3

Lys Arg Phe Phe
1

<210> SEQ ID NO 4
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 4

Ala Ser Asp Asp
1
```

```
<210> SEQ ID NO 5
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 5

Leu Lys Ser Phe
1

<210> SEQ ID NO 6
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 6

Pro Lys Ala Arg
1

<210> SEQ ID NO 7
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 7

Trp Trp Tyr Trp
1

<210> SEQ ID NO 8
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 8

Val Lys Lys Arg
1

<210> SEQ ID NO 9
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 9

Tyr Asp Glu Lys
1

<210> SEQ ID NO 10
<211> LENGTH: 4
<212> TYPE: PRT
<213> ORGANISM: Unknown
<220> FEATURE:
<223> OTHER INFORMATION: Description of Unknown:
      Sub-motif sequence
```

```
<400> SEQUENCE: 10

Pro Val Arg Arg
1

<210> SEQ ID NO 11
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 11

Ser Asn Pro Val
1

<210> SEQ ID NO 12
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 12

Asp Lys Tyr Glu
1

<210> SEQ ID NO 13
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 13

Asp Val His Tyr
1

<210> SEQ ID NO 14
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 14

Asn Pro Asp Gln
1

<210> SEQ ID NO 15
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 15

Gln Glu Glu Phe
1

<210> SEQ ID NO 16
<211> LENGTH: 4
```

```
<212> TYPE: PRT
<213> ORGANISM: Unknown
<220> FEATURE:
<223> OTHER INFORMATION: Description of Unknown:
      Sub-motif sequence

<400> SEQUENCE: 16

Glu Asp Trp Pro
1

<210> SEQ ID NO 17
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 17

Glu Asp Phe Pro
1

<210> SEQ ID NO 18
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 18

Pro Leu Val Asp
1

<210> SEQ ID NO 19
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 19

Leu Arg Asp Pro
1

<210> SEQ ID NO 20
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 20

Pro Ala Arg Arg
1

<210> SEQ ID NO 21
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 21

Pro Glu Leu Glu
```

-continued

```
<210> SEQ ID NO 22
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 22

Pro Glu Tyr Lys
1

<210> SEQ ID NO 23
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 23

Val Val Val Ser
1

<210> SEQ ID NO 24
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 24

Tyr Asp Pro Val
1

<210> SEQ ID NO 25
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 25

Asp Gly Leu His
1

<210> SEQ ID NO 26
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 26

Asn Pro Gly Ser
1

<210> SEQ ID NO 27
<211> LENGTH: 4
<212> TYPE: PRT
<213> ORGANISM: Unknown
<220> FEATURE:
<223> OTHER INFORMATION: Description of Unknown:
```

```
                Sub-motif sequence

<400> SEQUENCE: 27

Asn Pro His Pro
1

<210> SEQ ID NO 28
<211> LENGTH: 4
<212> TYPE: PRT
<213> ORGANISM: Unknown
<220> FEATURE:
<223> OTHER INFORMATION: Description of Unknown:
        Sub-motif sequence

<400> SEQUENCE: 28

Pro Glu Ser Gln
1

<210> SEQ ID NO 29
<211> LENGTH: 4
<212> TYPE: PRT
<213> ORGANISM: Unknown
<220> FEATURE:
<223> OTHER INFORMATION: Description of Unknown:
        Sub-motif sequence

<400> SEQUENCE: 29

Pro Phe His Pro
1

<210> SEQ ID NO 30
<211> LENGTH: 4
<212> TYPE: PRT
<213> ORGANISM: Unknown
<220> FEATURE:
<223> OTHER INFORMATION: Description of Unknown:
        Sub-motif sequence

<400> SEQUENCE: 30

Pro Phe Leu Pro
1

<210> SEQ ID NO 31
<211> LENGTH: 4
<212> TYPE: PRT
<213> ORGANISM: Unknown
<220> FEATURE:
<223> OTHER INFORMATION: Description of Unknown:
        Sub-motif sequence

<400> SEQUENCE: 31

Val Glu Ser Val
1

<210> SEQ ID NO 32
<211> LENGTH: 4
<212> TYPE: PRT
<213> ORGANISM: Unknown
<220> FEATURE:
<223> OTHER INFORMATION: Description of Unknown:
        Sub-motif sequence

<400> SEQUENCE: 32

Pro Val Glu Ser
1

<210> SEQ ID NO 33
```

```
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 33

Pro Glu Val Ala
1

<210> SEQ ID NO 34
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 34

Pro Gln Asp Lys
1

<210> SEQ ID NO 35
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 35

Pro Trp Asp Gln
1

<210> SEQ ID NO 36
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 36

Pro Tyr Glu Val
1

<210> SEQ ID NO 37
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 37

Trp Glu Leu Pro
1

<210> SEQ ID NO 38
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 38
```

Tyr His Asp Ser
1

<210> SEQ ID NO 39
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 39

Ala Asn Tyr Pro
1

<210> SEQ ID NO 40
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 40

Glu Val Tyr His
1

<210> SEQ ID NO 41
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 41

Pro Asp Ala Glu
1

<210> SEQ ID NO 42
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 42

Pro Asp Arg Asp
1

<210> SEQ ID NO 43
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 43

Pro Leu Asn Glu
1

<210> SEQ ID NO 44
<211> LENGTH: 4
<212> TYPE: PRT
<213> ORGANISM: Unknown
<220> FEATURE:

```
<223> OTHER INFORMATION: Description of Unknown:
      Sub-motif sequence

<400> SEQUENCE: 44

Tyr Arg Asn Asp
1

<210> SEQ ID NO 45
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 45

His His Ala Pro
1

<210> SEQ ID NO 46
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 46

Arg Val Trp Trp
1

<210> SEQ ID NO 47
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 47

Leu Gly Asn Trp
1

<210> SEQ ID NO 48
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 48

Pro Tyr Tyr Tyr
1

<210> SEQ ID NO 49
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 49

Gly His Arg Tyr
1
```

```
<210> SEQ ID NO 50
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 50

Arg Arg Leu Val
1

<210> SEQ ID NO 51
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 51

Arg Tyr Arg Trp
1

<210> SEQ ID NO 52
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 52

Arg Tyr Ser Trp
1

<210> SEQ ID NO 53
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 53

Val Arg Tyr Arg
1

<210> SEQ ID NO 54
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 54

Tyr Arg Arg Asn
1

<210> SEQ ID NO 55
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 55
```

Arg Tyr His Tyr
1

<210> SEQ ID NO 56
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 56

Gly Phe Val Gln
1

<210> SEQ ID NO 57
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 57

Pro Pro Phe Arg
1

<210> SEQ ID NO 58
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 58

Leu Arg Tyr Gly
1

<210> SEQ ID NO 59
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 59

Pro Pro Arg Asn
1

<210> SEQ ID NO 60
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 60

Tyr Tyr Tyr Asp
1

<210> SEQ ID NO 61
<211> LENGTH: 4
<212> TYPE: PRT
<213> ORGANISM: Unknown

-continued

```
<220> FEATURE:
<223> OTHER INFORMATION: Description of Unknown:
      Sub-motif sequence

<400> SEQUENCE: 61

Tyr Asp Glu Tyr
1

<210> SEQ ID NO 62
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 62

Ser Tyr Glu Glu
1

<210> SEQ ID NO 63
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 63

Glu Lys Lys Asp
1

<210> SEQ ID NO 64
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 64

Arg Asn Tyr Ala
1

<210> SEQ ID NO 65
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 65

Ala Arg Ser Gln
1

<210> SEQ ID NO 66
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 66

Asn Glu Val Asp
1
```

```
<210> SEQ ID NO 67
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 67

Asp Glu His His
1

<210> SEQ ID NO 68
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 68

Val Asp Asp His
1

<210> SEQ ID NO 69
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 69

Pro Val Arg Gln
1

<210> SEQ ID NO 70
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 70

Pro Leu Arg Arg
1

<210> SEQ ID NO 71
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 71

Asp Tyr Tyr Gly
1

<210> SEQ ID NO 72
<211> LENGTH: 4
<212> TYPE: PRT
<213> ORGANISM: Unknown
<220> FEATURE:
<223> OTHER INFORMATION: Description of Unknown:
      Sub-motif sequence
```

```
<400> SEQUENCE: 72

His Pro Asp Glu
1

<210> SEQ ID NO 73
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 73

Pro Pro Arg Lys
1

<210> SEQ ID NO 74
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 74

Lys His Val Arg
1

<210> SEQ ID NO 75
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 75

Glu Glu His Ser
1

<210> SEQ ID NO 76
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 76

Pro Arg Asn Arg
1

<210> SEQ ID NO 77
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 77

Arg Ala Tyr Lys
1

<210> SEQ ID NO 78
<211> LENGTH: 4
<212> TYPE: PRT
```

-continued

```
<213> ORGANISM: Unknown
<220> FEATURE:
<223> OTHER INFORMATION: Description of Unknown:
      Sub-motif sequence

<400> SEQUENCE: 78

Arg Trp Tyr Tyr
1

<210> SEQ ID NO 79
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 79

Val Trp Trp Trp
1

<210> SEQ ID NO 80
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 80

Tyr Trp Gly Asn
1

<210> SEQ ID NO 81
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 81

Ala Ser Glu Glu
1

<210> SEQ ID NO 82
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 82

Ser Asp Ser Tyr
1

<210> SEQ ID NO 83
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 83

Gln Arg Ser Gln
1
```

```
<210> SEQ ID NO 84
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 84

Trp Phe Pro His
1

<210> SEQ ID NO 85
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 85

Arg Gln Tyr Gln
1

<210> SEQ ID NO 86
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 86

Ser Ala Tyr Glu
1

<210> SEQ ID NO 87
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 87

His Val Glu Val
1

<210> SEQ ID NO 88
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 88

Asn His Asn Val
1

<210> SEQ ID NO 89
<211> LENGTH: 4
<212> TYPE: PRT
<213> ORGANISM: Unknown
<220> FEATURE:
<223> OTHER INFORMATION: Description of Unknown:
      Sub-motif sequence
```

```
<400> SEQUENCE: 89

Asp Tyr Trp Lys
1

<210> SEQ ID NO 90
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 90

Asp Lys Ser Gly
1

<210> SEQ ID NO 91
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 91

Pro Asp Leu Gln
1

<210> SEQ ID NO 92
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 92

Pro Asp Ser Val
1

<210> SEQ ID NO 93
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 93

Pro Asp Val Val
1

<210> SEQ ID NO 94
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 94

Pro Glu Arg Ala
1

<210> SEQ ID NO 95
<211> LENGTH: 4
```

```
<212> TYPE: PRT
<213> ORGANISM: Unknown
<220> FEATURE:
<223> OTHER INFORMATION: Description of Unknown:
      Sub-motif sequence

<400> SEQUENCE: 95

Pro Gly Ser Leu
1

<210> SEQ ID NO 96
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 96

Pro Gln Glu Ser
1

<210> SEQ ID NO 97
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 97

Pro Asp His Gln
1

<210> SEQ ID NO 98
<211> LENGTH: 93
<212> TYPE: PRT
<213> ORGANISM: Homo sapiens

<400> SEQUENCE: 98

Met Asp Arg Leu Gln Thr Ala Leu Leu Val Val Leu Val Leu Leu Ala
1               5                   10                  15

Val Ala Leu Gln Ala Thr Glu Ala Gly Pro Tyr Gly Ala Asn Met Glu
            20                  25                  30

Asp Ser Val Cys Cys Arg Asp Tyr Val Arg Tyr Arg Leu Pro Leu Arg
        35                  40                  45

Val Val Lys His Phe Tyr Trp Thr Ser Asp Ser Cys Pro Arg Pro Gly
    50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90

<210> SEQ ID NO 99
<211> LENGTH: 4
<212> TYPE: PRT
<213> ORGANISM: Unknown
<220> FEATURE:
<223> OTHER INFORMATION: Description of Unknown:
      Sub-motif sequence

<400> SEQUENCE: 99

Ser Gly Leu Phe
1
```

METHODS FOR DIFFERENTIAL DIAGNOSIS OF AUTOIMMUNE DISEASES

CROSS-REFERENCE

This patent application is a National Stage Entry of International Application No. PCT/US2017/038391, which claims the benefit of U.S. Application Ser. No. 62/352,525, filed Jun. 20, 2016; and U.S. Application Ser. No. 62/421,180, filed Nov. 11, 2016; each of which is incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 10, 2021, is named 59582-705_831_SL.txt and is 17,277 bytes in size.

BACKGROUND OF THE INVENTION

Autoimmune disease patients can experience chronically active disease, fluctuating rounds of remission and flare, or long quiescence. Accurately detecting and determining the status of a patient is central to prescribing appropriate drug regimens, evaluating treatment outcomes, defining patient subgroups, and early detection of flare onsets or progression of disease in order to improve therapeutic outcomes of patients afflicted with an autoimmune disease.

SUMMARY OF THE INVENTION

Provided herein are methods, devices and assays for making a differential diagnosis of an autoimmune disease, said method comprising (a) contacting a sample from a subject to an array of peptides comprising at least 10,000 different peptides synthesized in situ; (b) detecting the binding of antibodies present in said sample to at least 25 peptides on said array to obtain a combination of binding signals; and (c) comparing said combination of binding signals to one or more groups of combinations of reference binding signals, wherein at least one of each of said group of combinations of reference binding signals are obtained from a plurality of reference subjects known to have a disease different from the autoimmune disease of the subject, thereby enabling the differential diagnosis of said subject for the autoimmune disease, wherein the method performance is characterized by an area under the receiver operator characteristic (ROC) curve (AUC) between the autoimmune disease and each of the group of combinations of reference binding signals being greater than 0.6.

In some embodiments, the methods, devices and assays further comprises each of said combination of reference binding signals is obtained by detecting the binding of antibodies present in a sample from each of said plurality of subjects in said reference group to said at least 25 peptides on an array of peptides comprising at least 10,000 different peptides synthesized in situ. In some embodiments, the difference between said combination of binding signals and said combination of said reference binding signals to said at least 25 peptides determines said differential diagnosis. In an embodiment, said different disease is an autoimmune disease. In some embodiments, the methods, devices and assays further comprises (d) comparing said combination of binding signals to a reference binding signal obtained from a plurality of reference subjects known to have the autoimmune disease.

In another embodiment, said autoimmune-disease is dermatomyositis (DM), and said different autoimmune disease is scleroderma (SSc). In still other embodiments, said at least 25 peptides that differentiate said combination of binding signals from said combination of said reference binding signals are enriched by at least 100% in one or more amino acids selected from serine, glycine, tyrosine, arginine, alanine, glutamine and valine when compared to the at least 10,000 peptides in said array. In another embodiment, said at least 25 peptides that differentiate said combination of binding signals from said combination of said reference binding signals are enriched in one or more of the motifs listed in FIG. 13A when compared to the at least 10,000 peptides in said array.

In some embodiments, the method further comprises comparing the binding signal from said subject to a combination of reference binding signals obtained from healthy subjects. In some embodiments wherein the autoimmune disease is SSc, the at least 25 peptides that differentiate said combination of binding signals from said combination of said healthy reference binding signals are enriched by at least 100% in one or more amino acids selected from tyrosine, lys, arginine, phenylalanine, serine, tryptophan, glycine, and alanine. In other embodiments, wherein the autoimmune disease is SSc, the at least 25 peptides that differentiate said combination of binding signals from said combination of said reference binding signals are enriched in one or more of the motifs listed in FIG. 5A when compared to the at least 10,000 peptides in said array.

In some embodiments, wherein the autoimmune disease is DM, the at least 25 peptides that differentiate said combination of binding signals from said combination of said reference binding signals from healthy subjects are enriched by at least 100% in one or more amino acids selected from tyrosine, tryptophan, serine, glycine, aspartic acid, and phenylalanine. In other embodiments, wherein the autoimmune disease is DM, the at least 25 peptides that differentiate said combination of binding signals from said combination of said reference binding signals are enriched in one or more of the motifs listed in FIG. 17A when compared to the at least 10,000 peptides in said array.

In some embodiments, said autoimmune disease is SSc, and said one group of reference binding signals comprises a combination of binding signals obtained from a plurality of subjects having other autoimmune diseases comprising Mixed Connective Tissue Disease (MCTD), Undifferentiated Connective Tissue Disease (UCTD), myositis, polymyositis, systemic lupus erythomatosus, and morphea. In some embodiments, wherein said autoimmune disease is SSc, said at least 25 peptides that differentiate said combination of binding signals from said combination of said reference binding signals are enriched by at least 100% in one or more amino acids selected aspartic acid, glutamic acid, proline, valine, glycine, and serine. In other embodiments, wherein said autoimmune disease is SSc, said at least 25 peptides that differentiate said combination of binding signals from said combination of said reference binding signals are enriched in one or more of the motifs listed in FIG. 7A when compared to the at least 10,000 peptides in said array.

In some embodiments, said autoimmune disease is DM, and wherein said one group of reference binding signals comprises a combination of binding signals obtained from a plurality of subjects having other autoimmune diseases comprising MCTD, UCTD, myositis, polymyositis, systemic lupus erythomatosus, and morphea. In some embodiments, wherein said autoimmune disease is DM, said at least 25 peptides that differentiate said combination of binding signals from said combination of said reference binding signals are enriched by at least 100% in one or more amino acids selected lysine, histidine, serine, arginine, glutamic acid, alanine, and glycine. In other embodiments, wherein said autoimmune disease is DM, the at least 25 peptides that differentiate said combination of binding signals from said combination of said reference binding signals are enriched in one or more of the motifs listed in FIG. 19A when compared to the at least 10,000 peptides in said array.

In still other embodiments, the methods, devices and assays disclosed herein further comprises comparing the binding signal from said subject to a binding signal obtained from at least one healthy subject. In some embodiments, the method performance is characterized by an area under the receiver operator characteristic (ROC) curve (AUC) ranging from 0.60 to 0.70, 0.70 to 0.79, 0.80 to 0.89, or 0.90 to 1.00.

Also provided herein are methods, devices and assays for determining disease progression in a subject known to have an autoimmune disease, said method comprising (a) contacting a sample from a subject to an array of peptides comprising at least 10,000 different peptides synthesized in situ; (b) detecting the binding of antibodies present in said sample to at least 25 peptides on said array to obtain a first combination of binding signals; and (c) comparing said first combination of binding signals to at least a second combination of reference binding signals, wherein said second combination of reference binding signals comprises a combination of binding signals obtained from a reference group comprising a plurality of subjects having a clinical manifestation indicative of progression of said autoimmune disease, thereby making said differential diagnosis, wherein the method performance is characterized by an area under the receiver operator characteristic (ROC) curve (AUC) being greater than 0.6. In some embodiments, the methods, devices and assays further comprises (d) comparing said combination of binding signals to a reference binding signal obtained from a plurality of reference subjects known to have the autoimmune disease.

In some embodiments, each of said combination of reference binding signals is obtained by detecting the binding of antibodies present in a sample from each of said plurality of subjects in said reference group to said at least 25 peptides on a array of peptides comprising at least 10,000 different peptides synthesized in situ. In one embodiment, the difference between said combination of binding signals and said combination of said reference binding signals to said at least 25 peptides determines said disease progression. In another embodiment, said disease progression is determined in scleroderma (SSc). In yet other embodiments, said disease progression is determined in SSc, and said clinical manifestation is selected from renal crisis, interstitial lung disease (ILD), and gastric antral vascular ectasia (GAVE).

In one embodiment, said disease progression is determined in subjects having SSc, and said clinical manifestation is renal crisis. In some embodiments, said at least 25 peptides that differentiate said combination of binding signals from said combination of said reference binding signals are enriched by at least 100% in one or more amino acids selected from proline, aspartic acid and glutamic acid when compared to the at least 10,000 peptides in said array. In other embodiments, said at least 25 peptides that differentiate said combination of binding signals from said combination of said reference binding signals are enriched by at least in one or more motifs listed in FIG. 9A when compared to the at least 10,000 peptides in said array.

In another embodiment, wherein said disease progression is determined in SSc, and said clinical manifestation is ILD. In some embodiments, said at least 25 peptides that differentiate said combination of binding signals from said combination of said reference binding signals are enriched by at least in one or more amino acids selected from proline, arginine, lysine, histidine, and aspartic acid when compared to the at least 10,000 peptides in said array. In other embodiments, said at least 25 peptides that differentiate said combination of binding signals from said combination of said reference binding signals are enriched in one or more of the motifs listed in FIG. 15A when compared to the at least 10,000 peptides in said array.

In another embodiment, said disease progression is determined in SSc, and said clinical manifestation is GAVE. In one embodiment, said at least 25 peptides that differentiate said combination of binding signals from said combination of said reference binding signals are enriched by at least in one or more amino acids selected from arginine, tyrosine, serine, histidine, lysine, and phenylalanine when compared to the at least 10,000 peptides in said array. In another embodiment, said at least 25 peptides that differentiate said combination of binding signals from said combination of said reference binding signals are enriched in one or more of the motifs listed in FIG. 11A when compared to the at least 10,000 peptides in said array.

In another embodiment, said disease progression is determined in subjects with dermatomyositis (DM), and said clinical manifestation is ILD. In one embodiment, said at least 25 peptides that differentiate said combination of binding signals from said combination of said reference binding signals are enriched by at least in one or more amino acids selected from proline, aspartic acid, glutamic acid, serine, glycine, and glutamine when compared to the at least 10,000 peptides in said array. In another embodiment, said at least 25 peptides that differentiate said combination of binding signals from said combination of said reference binding signals are enriched in one or more of the motifs listed in FIG. 21A when compared to the at least 10,000 peptides in said array.

In still other embodiments, the method performance is characterized by an area under the receiver operator characteristic (ROC) curve (AUC) ranging from 0.60 to 0.70, 0.70 to 0.79, 0.80 to 0.89, or 0.90 to 1.00.

In some embodiments, the subject is human. In other embodiments, the sample is a blood sample. In still other embodiments, the blood sample is selected from whole blood, plasma, or serum. In yet other embodiments, the sample is a serum sample. In one embodiment, the sample is a plasma sample. In another embodiment, the sample is a dried blood sample. In still other embodiments, the at least 10,000 different peptides on the peptide array is at least 5 amino acids in length. In yet other embodiments, the at least 10,000 different peptides on the peptide array is between 5 and 15 amino acids in length. In some embodiments, the at least 10,000 different peptides are synthesized from less than 20 amino acids. In another embodiment, the at least 10,000 different peptides on the peptide array are synthesized by excluding one or more of cysteine, methionine, isoleucine and threonine.

In another aspect, a method is provided for identifying a candidate protein biomarker for an autoimmune disease, said method comprising: (a) identifying a set of discriminating peptides that differentiate said autoimmune disease from one or more different health condition; (b) aligning said set of (discriminating) peptides to proteins in a proteome to obtain an alignment score for said set of discriminating peptides to one or more proteins of said proteome; (d) ranking said identified proteins according to a statistical significance; and (e) identifying said protein as a candidate protein biomarker for treating said autoimmune disease. In some embodiments, the method further comprises identifying a set of discriminating peptides that differentiate said autoimmune disease from a healthy condition. In some embodiments, the candidate protein biomarker is selected from targets listed in Table 3.

In some embodiments, the discriminating peptides are identified as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In other embodiments, said candidate protein biomarker is ranked according to a p-value of less than less than $10^{-3}$, less than less than $10^{-4}$, less than less than $10^{-5}$, or less than less than $10^{-6}$.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings in the following.

FIG. 1A is a list of clinical manifestations and physiological symptoms of SSc.

FIG. 1B shows a continuation of clinical manifestations and physiological symptoms of SSc.

FIG. 2 is an example of a list of clinical symptoms used to assess SSc diagnosis and assessment.

FIG. 3 shows a list of clinical manifestations and symptoms for polymyositis and dermatomyositis, and clinical differentiation criteria for both.

FIG. 5 is a table depicting the top differentiating peptides when comparing patients with SSc and healthy subjects.

FIG. 5A depicts the top sub-motifs. FIG. 5A discloses SEQ ID NOS 1-8, respectively, in order of appearance.

FIG. 5B depicts the enriched peptides in the top 1000 differentiating peptides.

FIG. 6 is a graphical representation of the results in FIG. 5.

FIG. 7 is a table depicting the top differentiating peptides in an immunosignature when comparing patients diagnosed with SSc and other autoimmune disorders.

FIG. 7A depicts the top sub-motifs. FIG. 7A discloses SEQ ID NOS 9-24, respectively, in order of appearance.

FIG. 7B depicts the enriched peptides in the top 1000 differentiating peptides.

FIG. 8 is a graphical representation of the results seen in FIG. 7.

FIG. 9 is a table depicting the top differentiating peptides in an immunosignature when comparing patients diagnosed with SSc and patients in a renal crisis.

FIG. 9A depicts the top sub-motifs. FIG. 9A discloses SEQ ID NOS 25-44, respectively, in order of appearance.

FIG. 9B depicts the enriched peptides in the top 1000 differentiating peptides.

the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 10A:
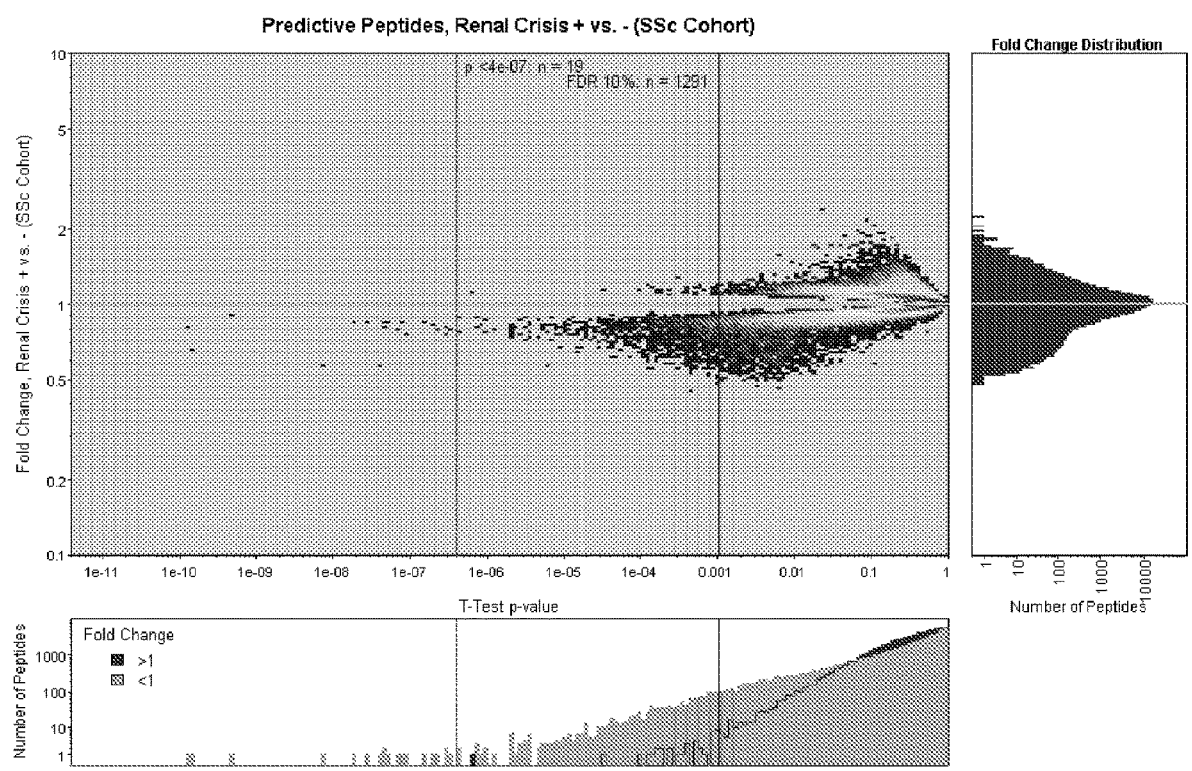
FIG. 10A is a Volcano Plot depicting the differentiation of subjects with Scleroderma (SSc) having renal crisis from subjects with SSc without renal crisis by peptide binding intensities. The ratio of mean intensity among samples from patients with Scleroderma having renal crisis to mean intensity in patients with SSc without renal crisis is plotted vs. the p-value for the difference in means from a t-test.
Figure 10B:
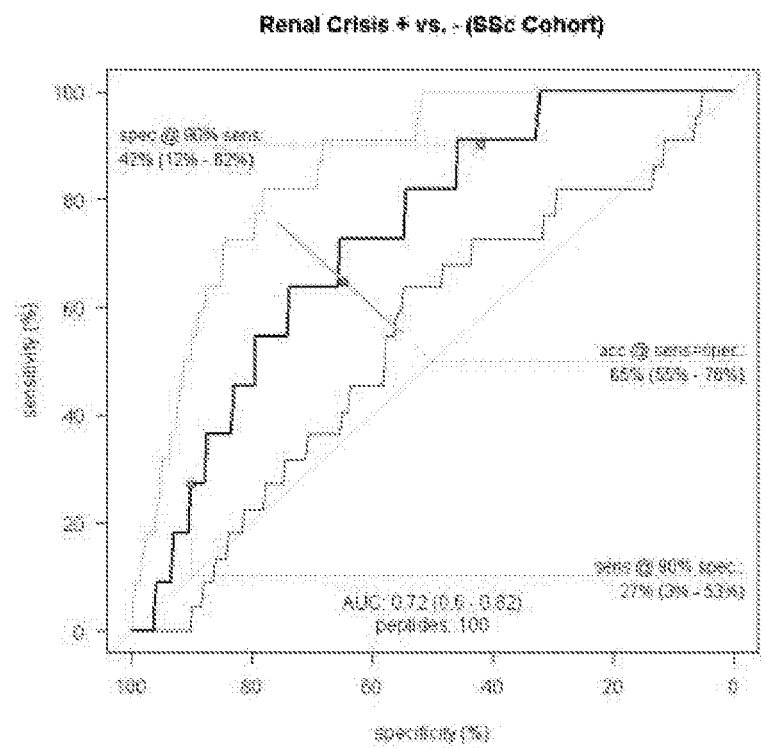
FIG. 10B are ROC curves for an ImmunoSignature model of Scleroderma for identifying patients with Scleroderma with renal crisis from subjects with SSc without renal crisis. The green line (top) indicates the upper 95% confidence interval of the classifier (middle) and the red line (bottom)
Figure 10C:
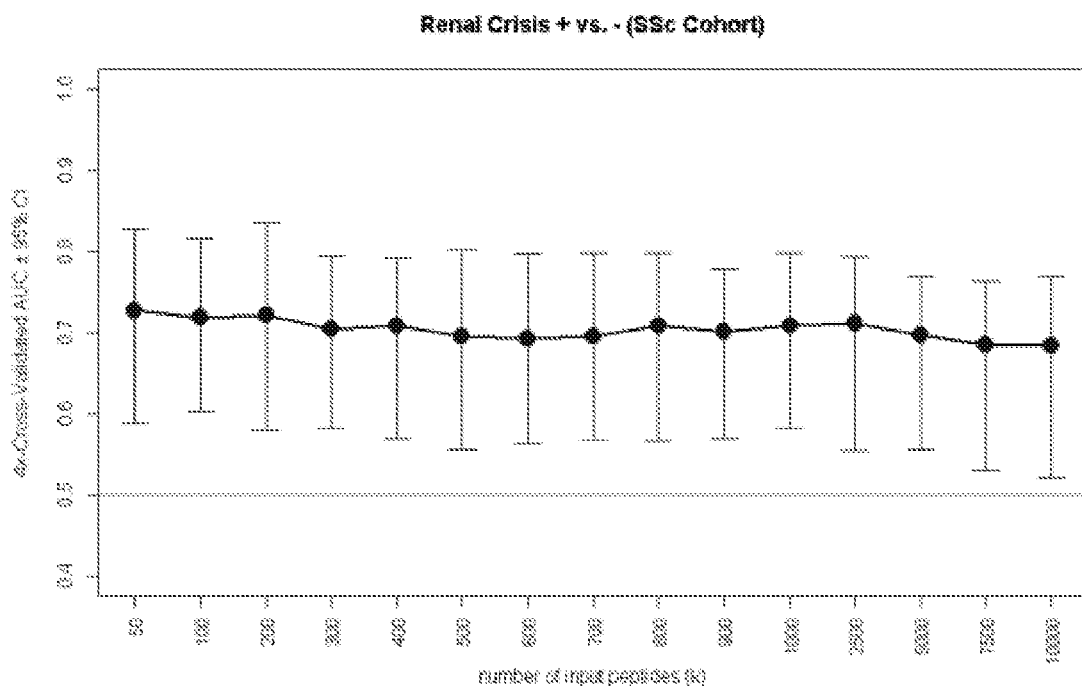
FIG. 10 is a graphical representation of the results seen in FIG. 9.

FIG. 10C are ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma with renal crisis vs. SSc without renal crisis. Feature selection and model construction were performed within the cross-validation loop to prevent bias.

FIG. 11 is a table depicting the top differentiating peptides in an immunosignature when comparing patients diagnosed with SSc and gastric antral vascular ectasia (GAVE).

FIG. 11A depicts the top sub-motifs. FIG. 11A discloses SEQ ID NOS 45-55, respectively, in order of appearance.

FIG. 11B depicts the enriched peptides in the top 1000 differentiating peptides.

FIG. 12 is a graphical representation of the results seen in FIG. 11.

Figure 12A:
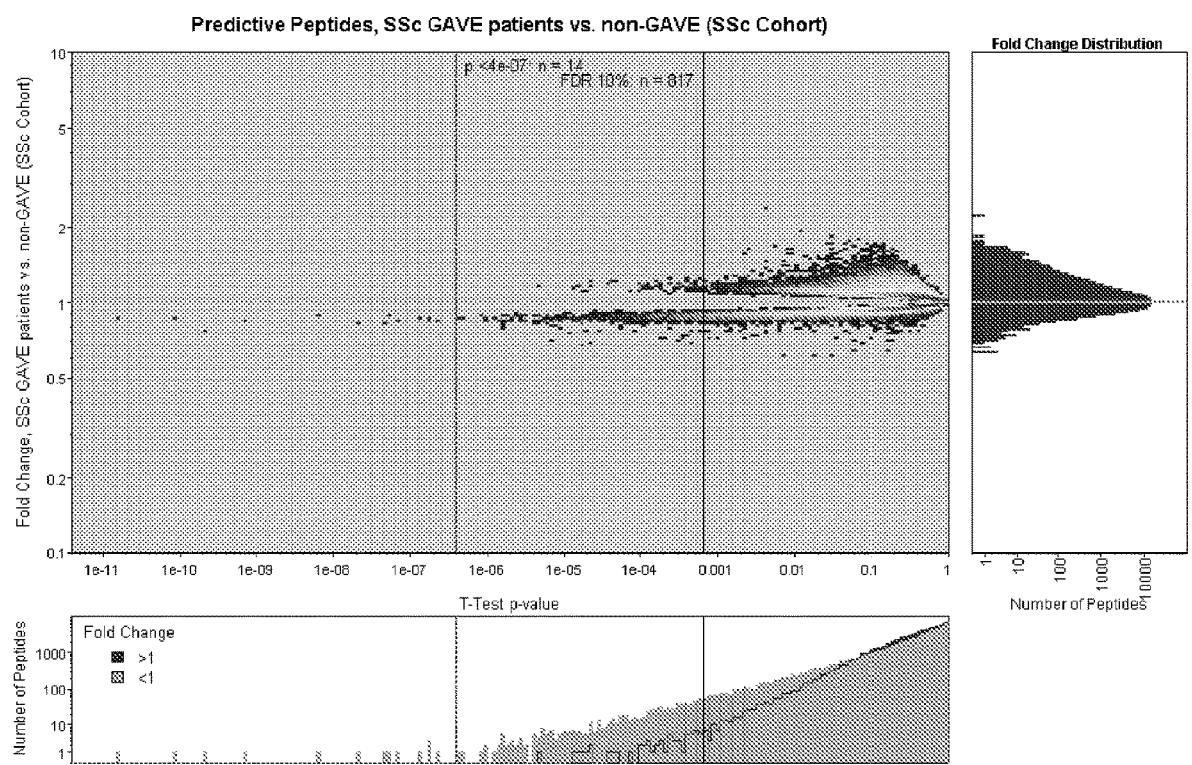

FIG. 12A is a Volcano Plot depicting the differentiation of subjects with Scleroderma (SSc) having Gastric Antral Vascular Ectasia (GAVE) from subjects with SSc without GAVE by peptide binding intensities. The ratio of mean intensity among samples from patients with Scleroderma having GAVE to mean intensity in patients with SSc without GAVE is plotted vs. the p-value for the difference in means from a t-test.

Figure 12B:
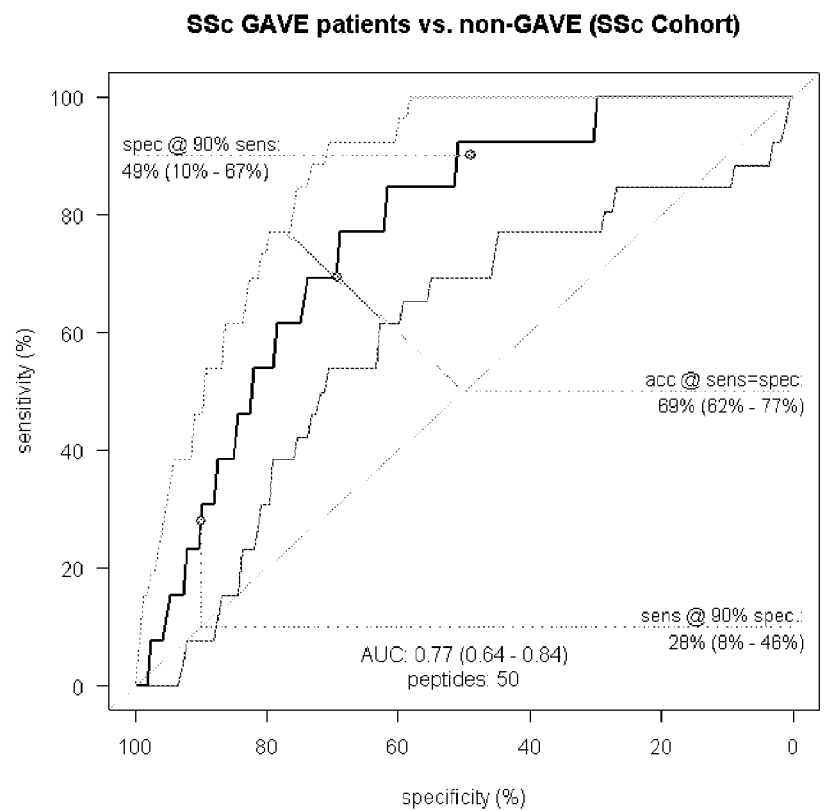

FIG. 12B are ROC curves for an ImmunoSignature model of Scleroderma for identifying patients with Scleroderma with GAVE from subjects with SSc without GAVE. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 12C:
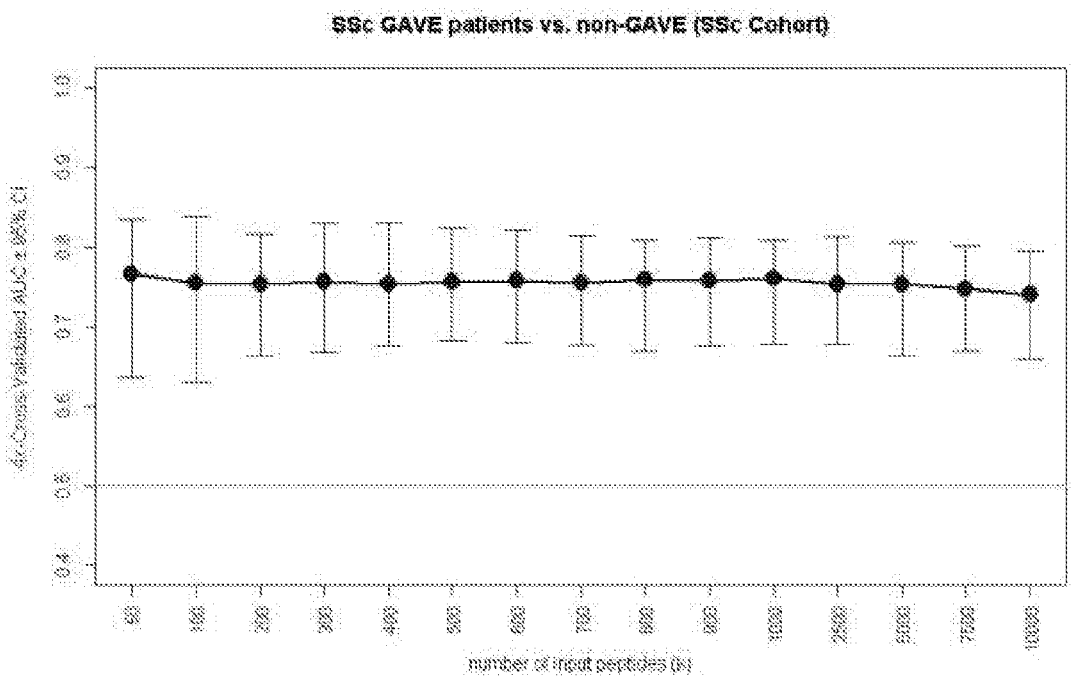

FIG. 12C are ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma with GAVE vs. SSc without GAVE. Feature selection and model construction were performed within the cross-validation loop to prevent bias.

FIG. 13 is a table depicting the top differentiating peptides in an immunosignature when comparing patients diagnosed with SSc and DM.

FIG. 13A depicts the top sub-motifs. FIG. 13A discloses SEQ ID NOS 56-59, 10, 60-62, 20, 63-66, and 99 respectively, in order of appearance.

FIG. 13B depicts the enriched peptides in the top 1000 differentiating peptides.

FIG. 14 is a graphical representation of the results seen in FIG. 13.

Figure 14A:
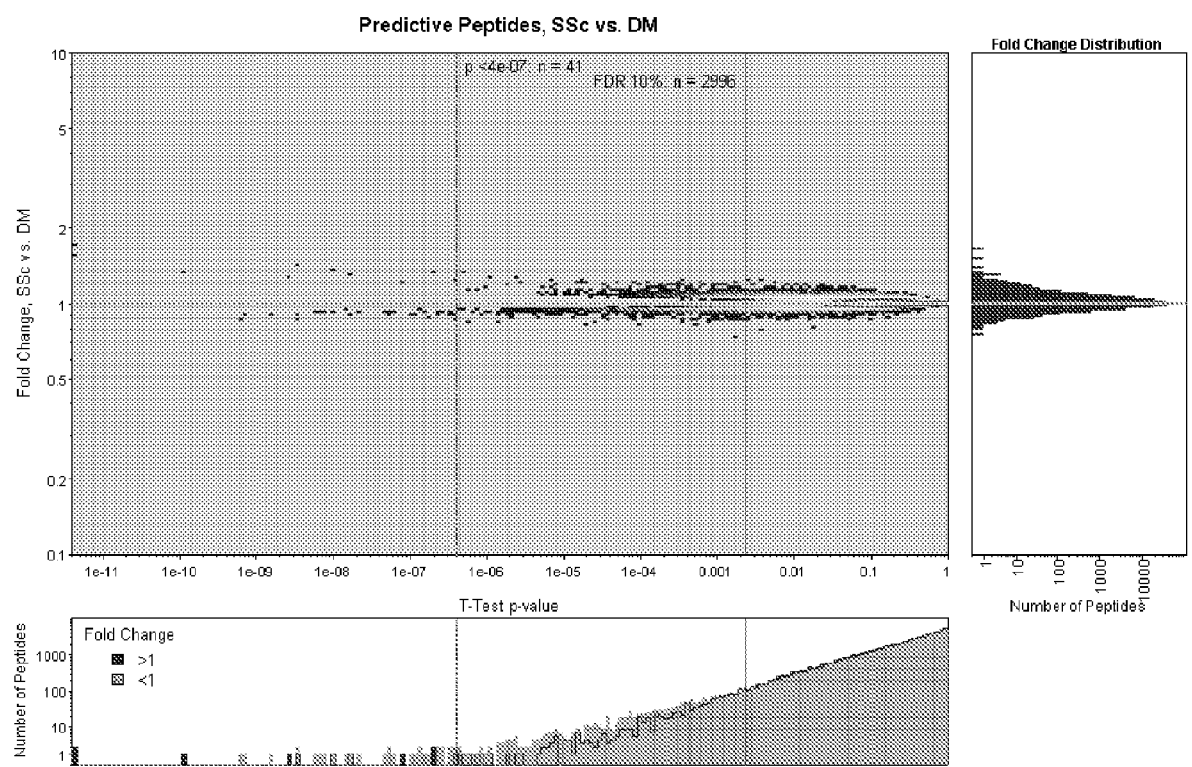

FIG. 14A is a Volcano Plot depicting the differentiation of subjects with Scleroderma (SSc) from subjects with Dermatomyositis (DM) by peptide binding intensities. The ratio of mean intensity among samples from patients with DM to mean intensity in patients with DM is plotted vs. the p-value for the difference in means from a t-test.

Figure 14B:
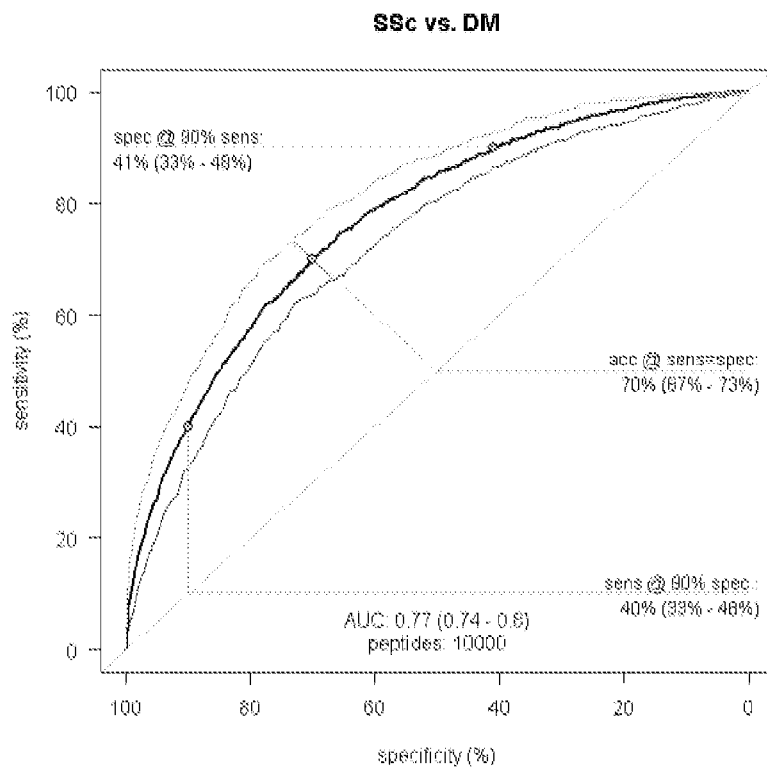

FIG. 14B are ROC curves for an ImmunoSignature model of Scleroderma for identifying patients with Scleroderma from DM. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 14C:
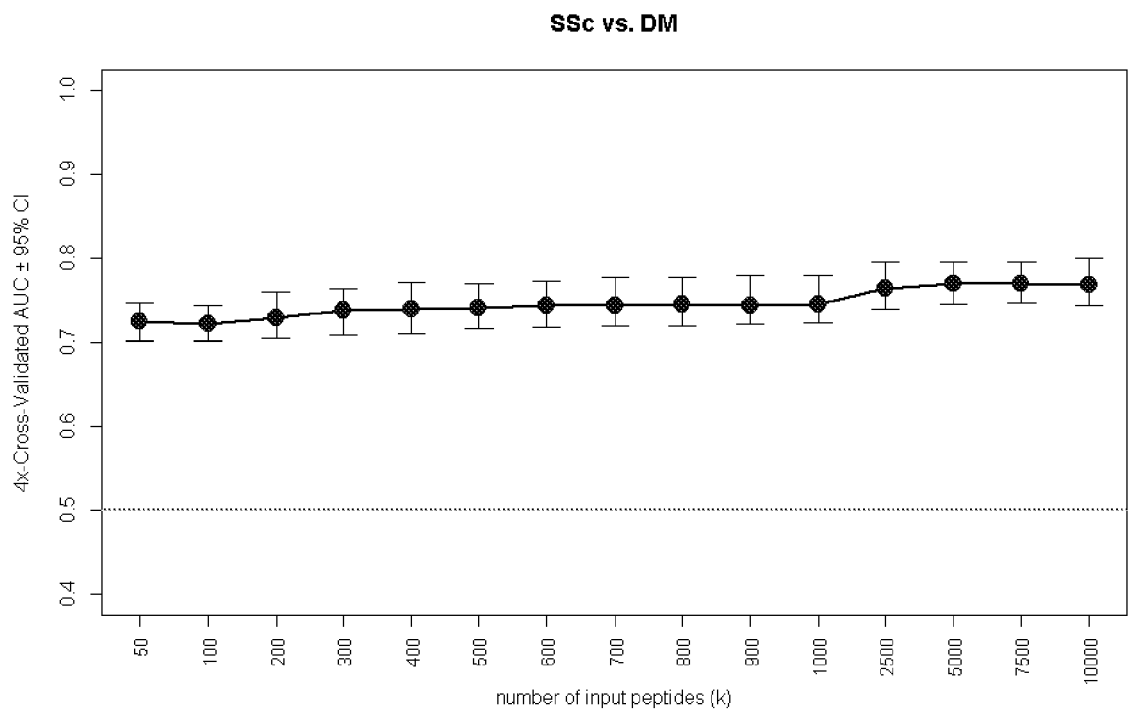

FIG. 14C are ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma vs. DM. Feature selection and model construction were performed within the cross-validation loop to prevent bias.

FIG. 15 is a table depicting the top differentiating peptides in an immunosignature when comparing patients diagnosed with SSc with interstitial lung disease (ILD+) and SSc without interstitial lung disease (ILD−).

FIG. 15A depicts the top sub-motifs. FIG. 15A discloses SEQ ID NOS 67, 57, and 68-77, respectively, in order of appearance.

FIG. 15B depicts the enriched peptides in the top 1000 differentiating peptides.

FIG. 16 is a graphical representation of the results seen in FIG. 15.

Figure 16A:
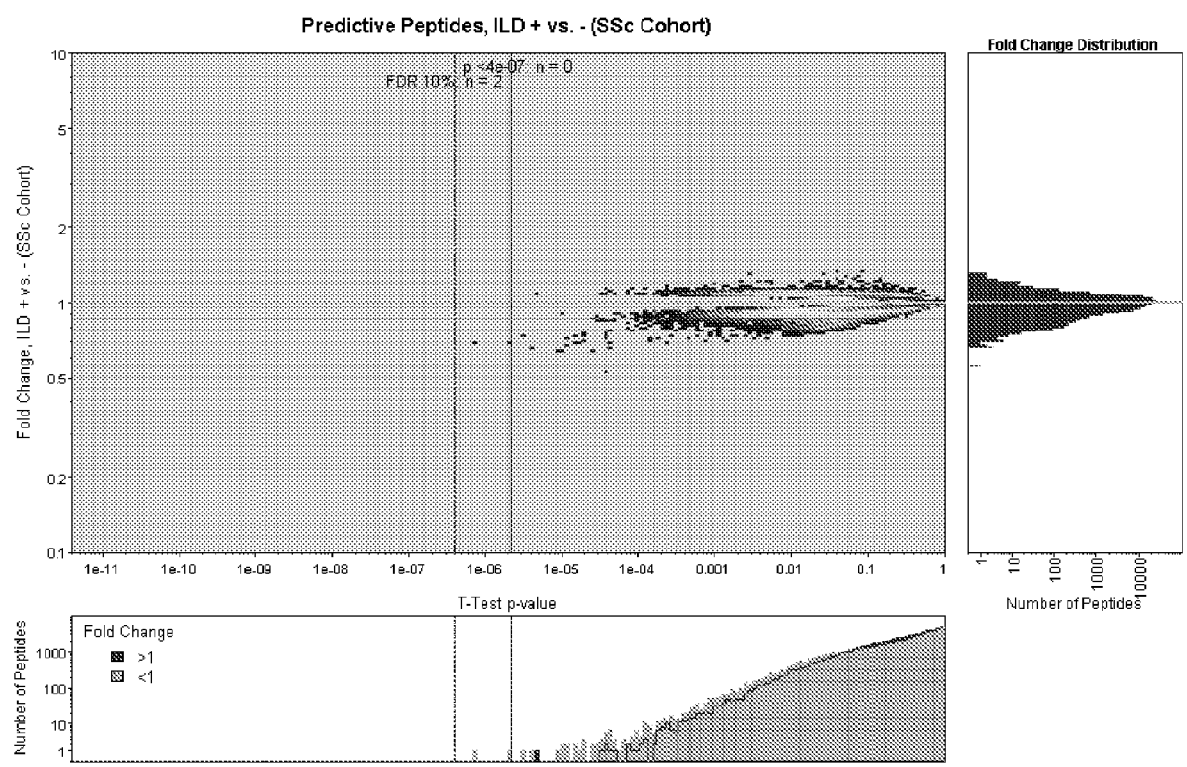

FIG. 16A is the differentiation of subjects with Scleroderma (SSc) having Interstitial Lung Disease (ILD) (ILD+) from subjects with SSC without ILD (ILD−) by peptide binding intensities. The ratio of mean intensity among samples from patients with Scleroderma-ILD+ to mean intensity in patients with SSC ILD− is plotted vs. the p-value for the difference in means from a t-test.

Figure 16B:
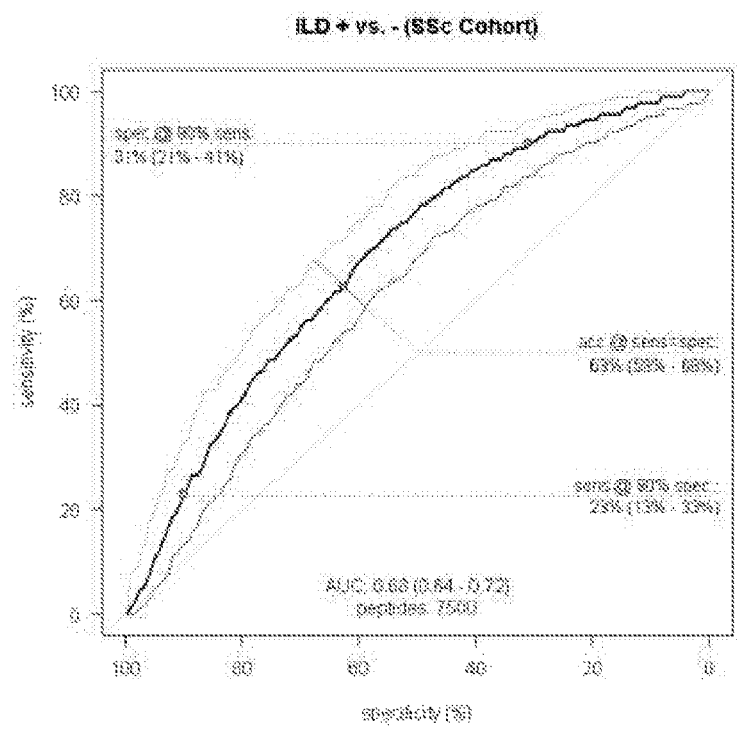

FIG. 16B are ROC curves for an ImmunoSignature model of Scleroderma for identifying patients with Scleroderma ILD+ from subjects with SSc ILD−. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 16C:
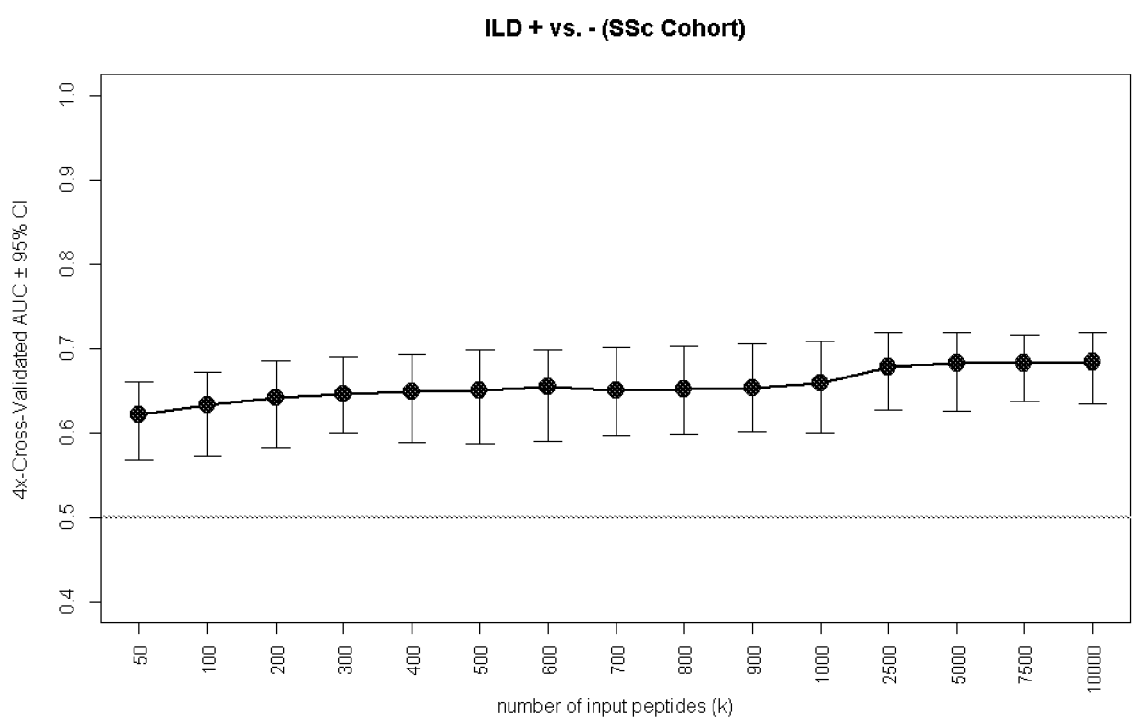

FIG. 16C are ROC estimates as a function of input size—Four fold cross validated area under the ROC curve (+/−95% CI) are provided for models of different input peptide sizes. Peptides were selected based on a t-test and the top k features were used in a support vector machine to build a classifier of SSc ILD+ vs. SSc ILD−. Feature selection and model construction were performed within the cross-validation loop to prevent bias.

FIG. 17 is a table depicting the top differentiating peptides in an immunosignature when comparing patients diagnosed with DM and healthy subjects.

FIG. 17A depicts the top sub-motifs. FIG. 17A discloses SEQ ID NOS 78-79, 2, 4, 80, 3, and 81-84 respectively, in order of appearance.

FIG. 17B depicts the enriched peptides in the top 1000 differentiating peptides.

FIG. 18 is a graphical representation of FIG. 17.

Figure 18A:
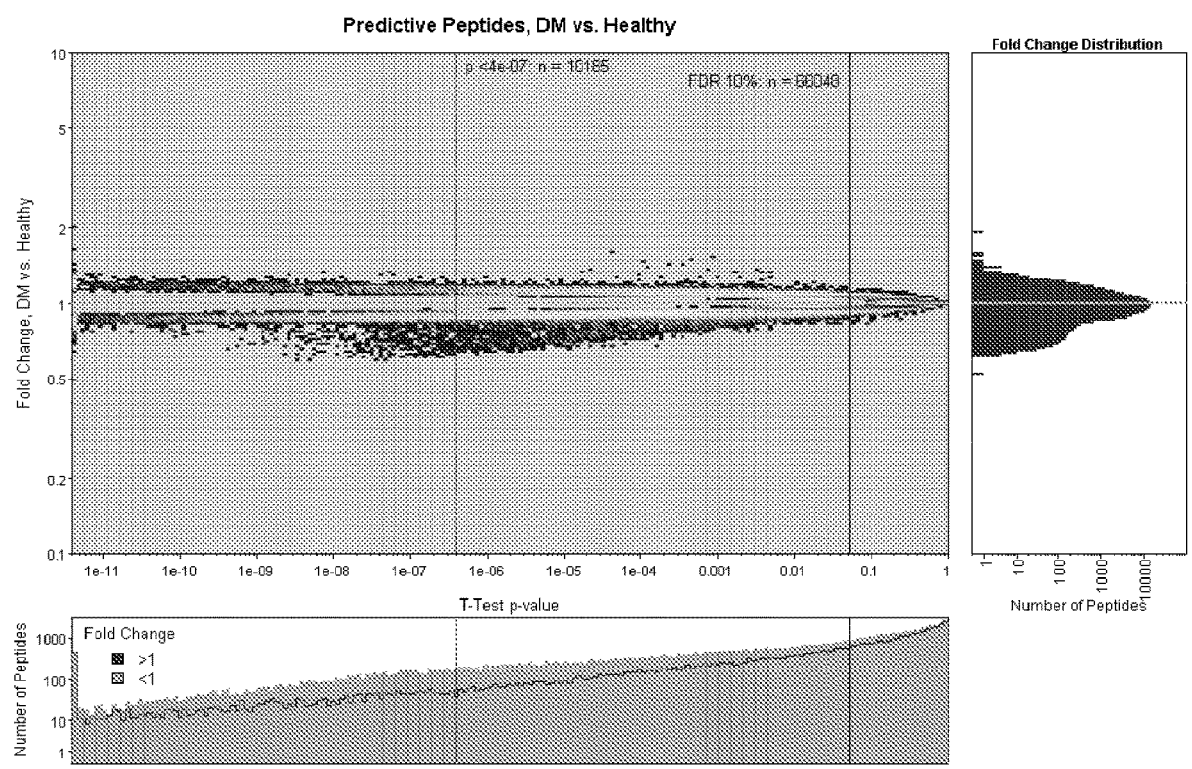

FIG. 18A is a Volcano Plot depicting the differentiation of subjects with Dermatomyositis (DM) from healthy controls by peptide binding intensities. The ratio of mean intensity among samples from patients with DM to mean intensity in control patients is plotted vs. the p-value for the difference in means from a t-test.

Figure 18B:
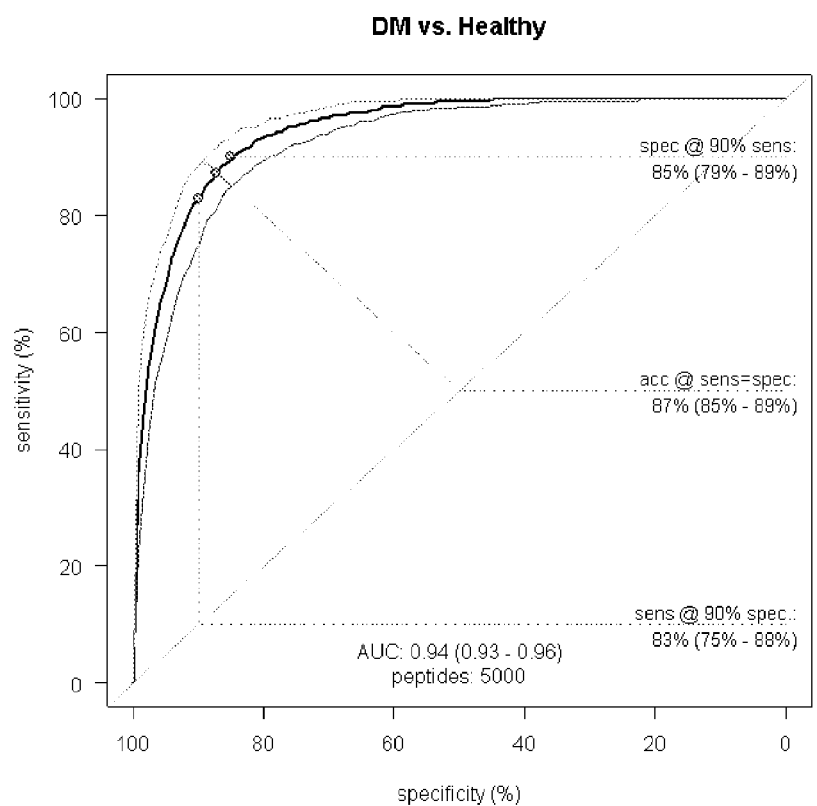

FIG. 18B are ROC curves for an ImmunoSignature model of DM for identifying patients with DM from healthy controls. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 18C:
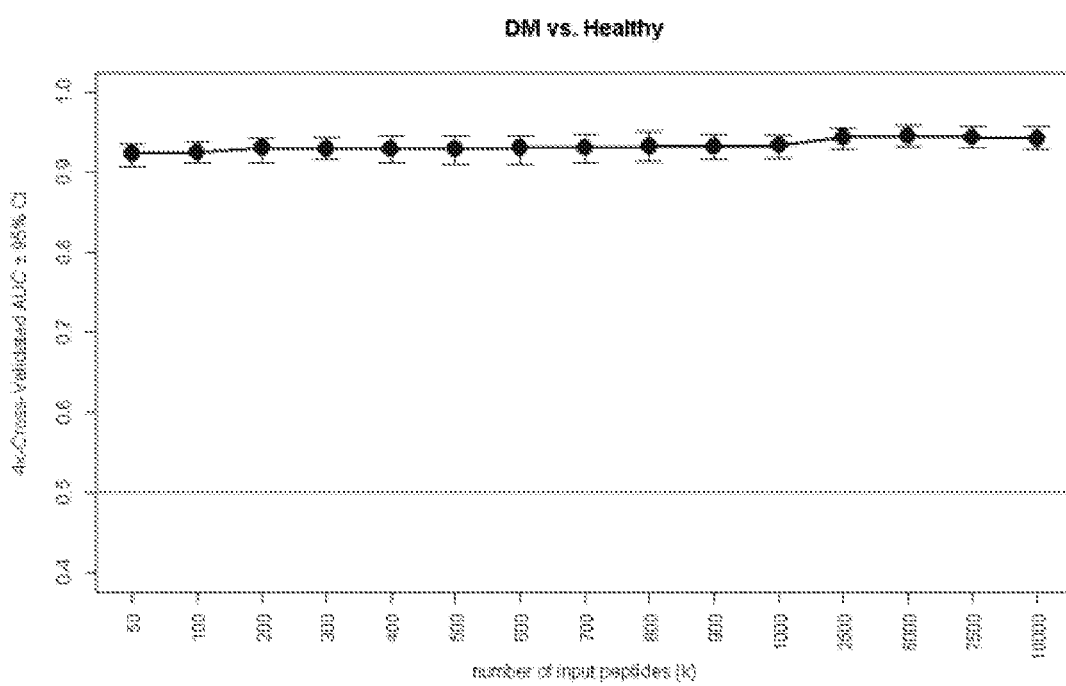

FIG. 18C are ROC estimates as a function of input size—Four fold cross validated area under the ROC curve (+/−95% CI) are provided for models of different input peptide sizes. Peptides were selected based on a t-test and the top k features were used in a support vector machine to build a classifier of DM vs. healthy controls. Feature selection and model construction were performed within the cross-validation loop to prevent bias.

FIG. 19 is a table depicting the top differentiating peptides in an immunosignature when comparing patients diagnosed with DM and other autoimmune disorders.

FIG. 19A depicts the top sub-motifs. FIG. 19A discloses SEQ ID NOS 85-90, respectively, in order of appearance.

FIG. 19B depicts the enriched peptides in the top 1000 differentiating peptides.

FIG. 20 is a graphical representation of FIG. 19.

Figure 20A:
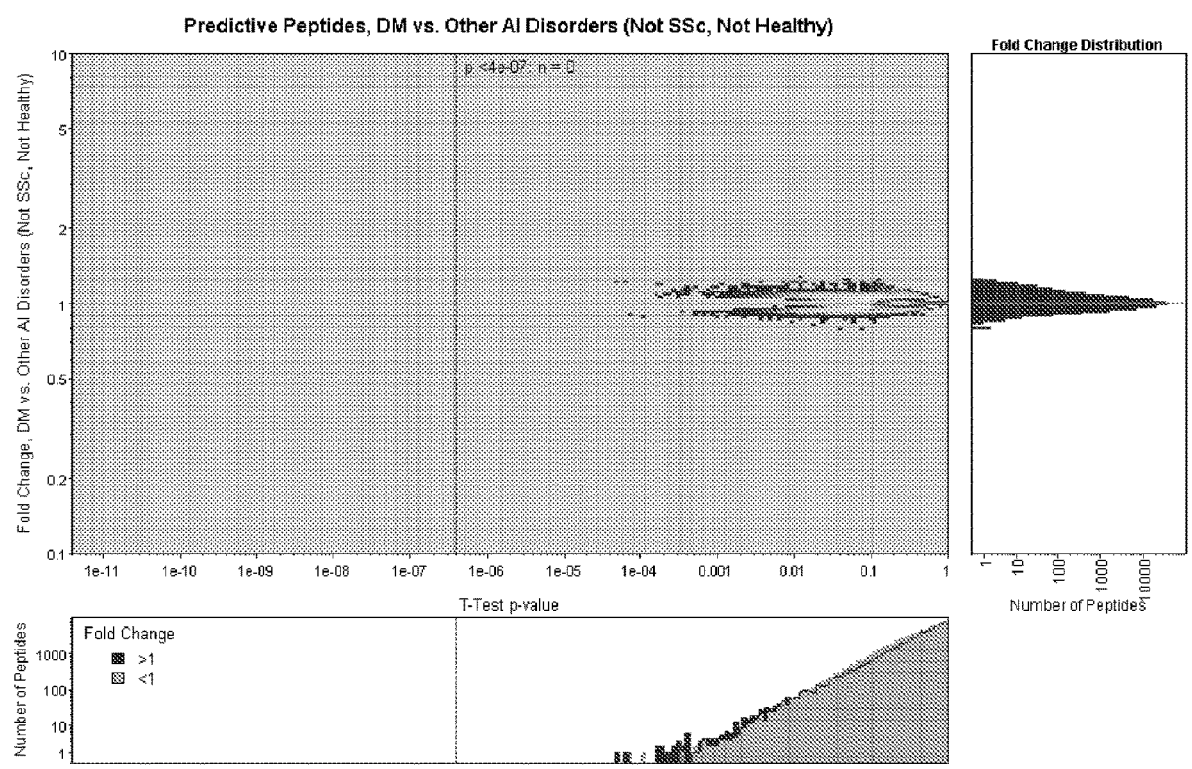

FIG. 20A is a Volcano Plot depicting the differentiation of subjects with Dermatomyositis (DM) from other autoimmune mimic diseases (Other AI) by peptide binding intensities. The ratio of mean intensity among samples from patients with Scleroderma to mean intensity in patients with other autoimmune disorders is plotted vs. the p-value for the difference in means from a t-test.

Figure 20B:
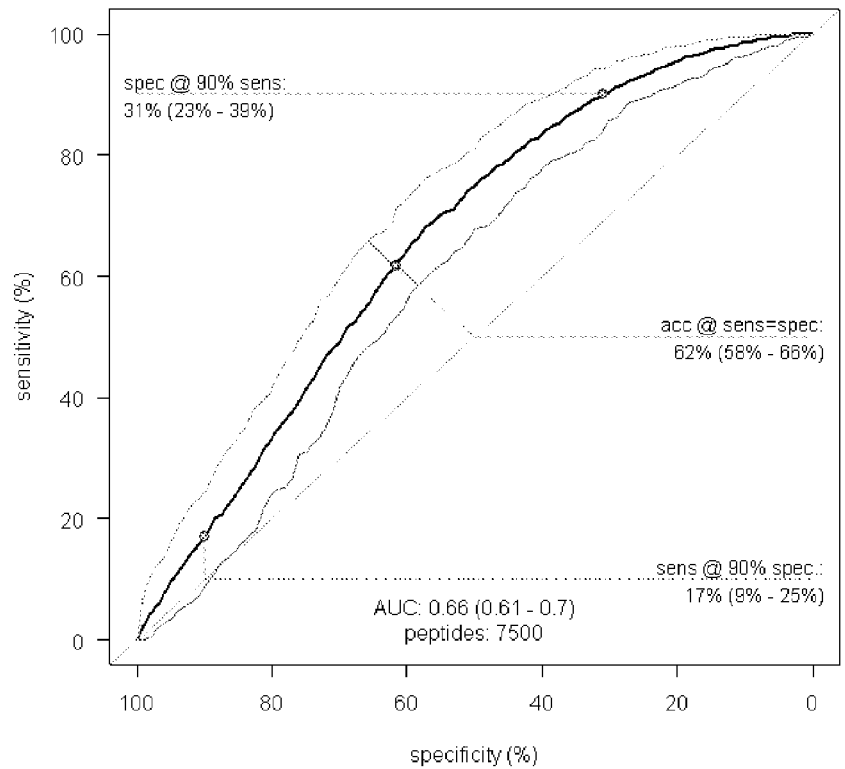

FIG. 20B are ROC curves for an ImmunoSignature model of DM for identifying Subjects with Dermatomyositis (DM) from other autoimmune mimic diseases (Other AI). The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 20C:
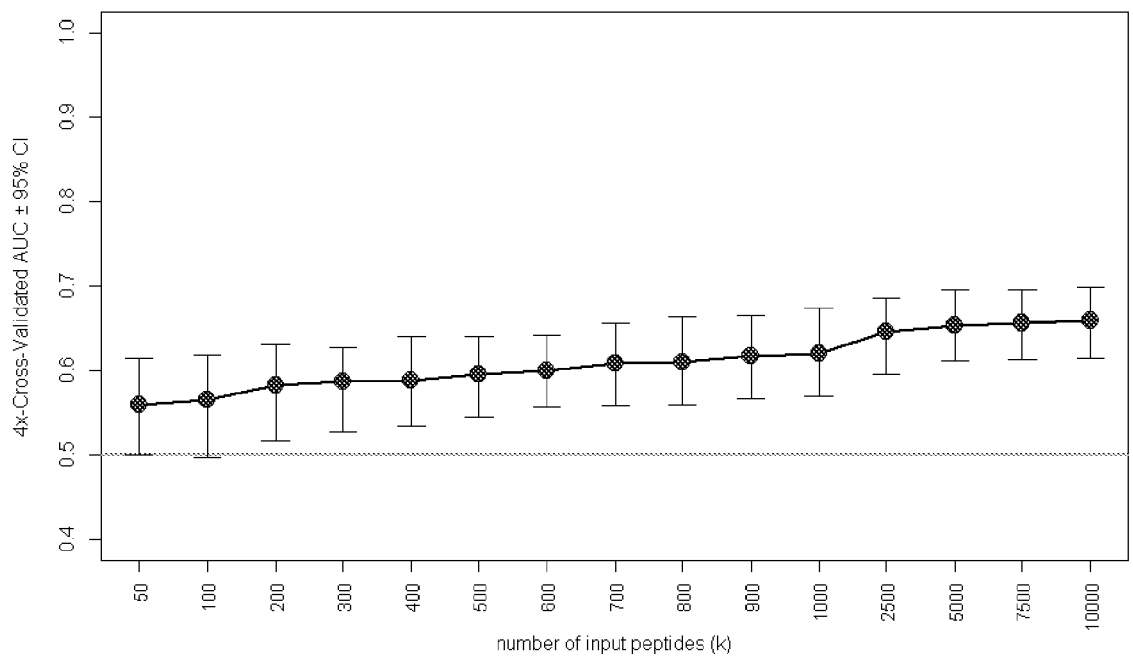

FIG. 20C are ROC estimates as a function of input size—Four fold cross validated area under the ROC curve (+/−95% CI) are provided for models of different input peptide sizes. Peptides were selected based on a t-test and the top k features were used in a support vector machine to build a classifier of DM vs. other autoimmune disorders. Feature selection and model construction were performed within the cross-validation loop to prevent bias.

FIG. 21 is a table depicting the top differentiating peptides in an immunosignature when comparing patients diagnosed with DM and Interstitial lung disease (ILD+) and DM without interstitial lung disease (ILD−).

FIG. 21A depicts the top sub-motifs. FIG. 21A discloses SEQ ID NOS 91-97, respectively, in order of appearance.

FIG. 21B depicts the enriched peptides in the top 1000 differentiating peptides.

FIG. 22 is a graphical representation of FIG. 21.

Figure 22A:
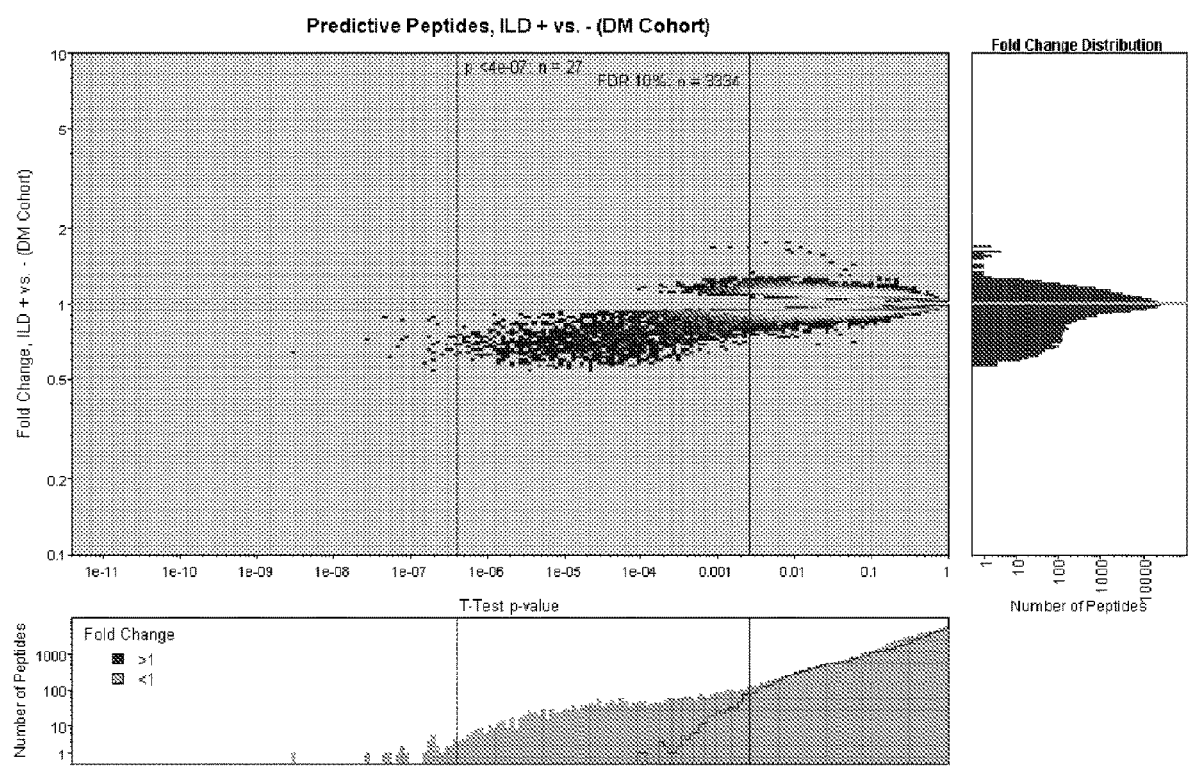

FIG. 22A is a Volcano Plot depicting the differentiation of subjects with Dermatomyositis (DM) having Interstitial Lung Disease (ILD) (ILD+) from subjects with DM without ILD (ILD−) by peptide binding intensities. The ratio of mean intensity among samples from patients with DM ILD+ to mean intensity in patients with DM ILD− is plotted vs. the p-value for the difference in means from a t-test.

Figure 22B:
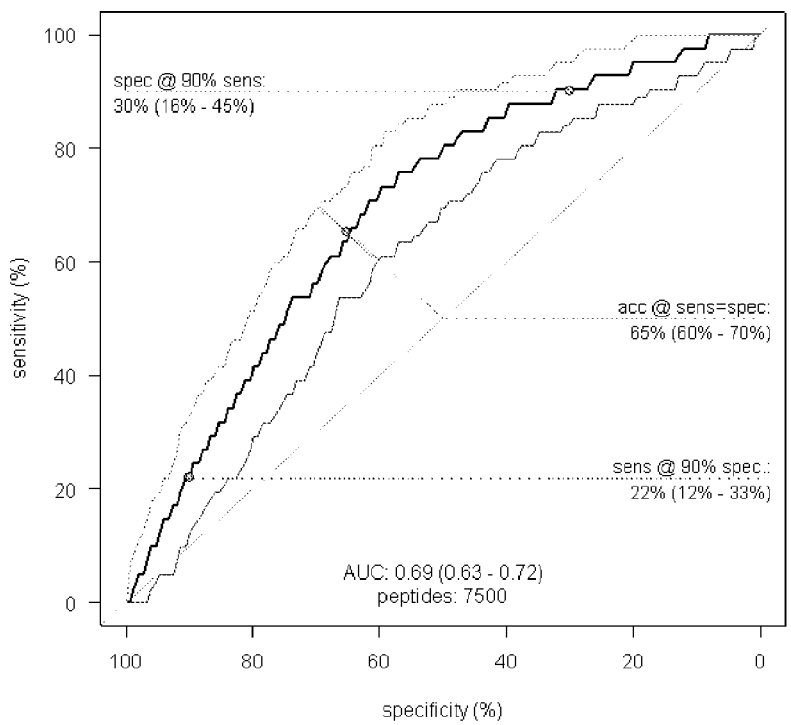

FIG. 22B are ROC curves for an ImmunoSignature model of DM for identifying patients with DMILD+ from subjects with DMILD−. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

Figure 22C:
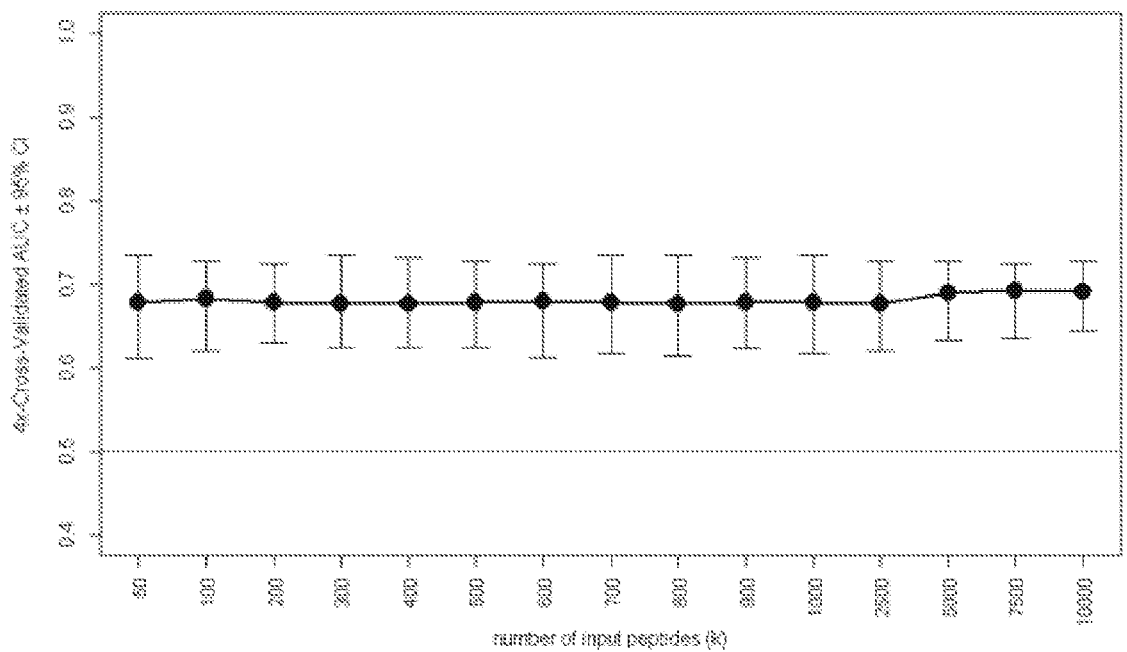

FIG. 22C are ROC estimates as a function of input size—Five fold cross validated area under the ROC curve (+/−95% CI) are provided for models of different input peptide sizes. Peptides were selected based on a t-test and the top k features were used in a support vector machine to build a classifier of DM ILD+ vs. DM ILD−. Feature selection and model construction were performed within the cross-validation loop to prevent bias.

Figure 23A:
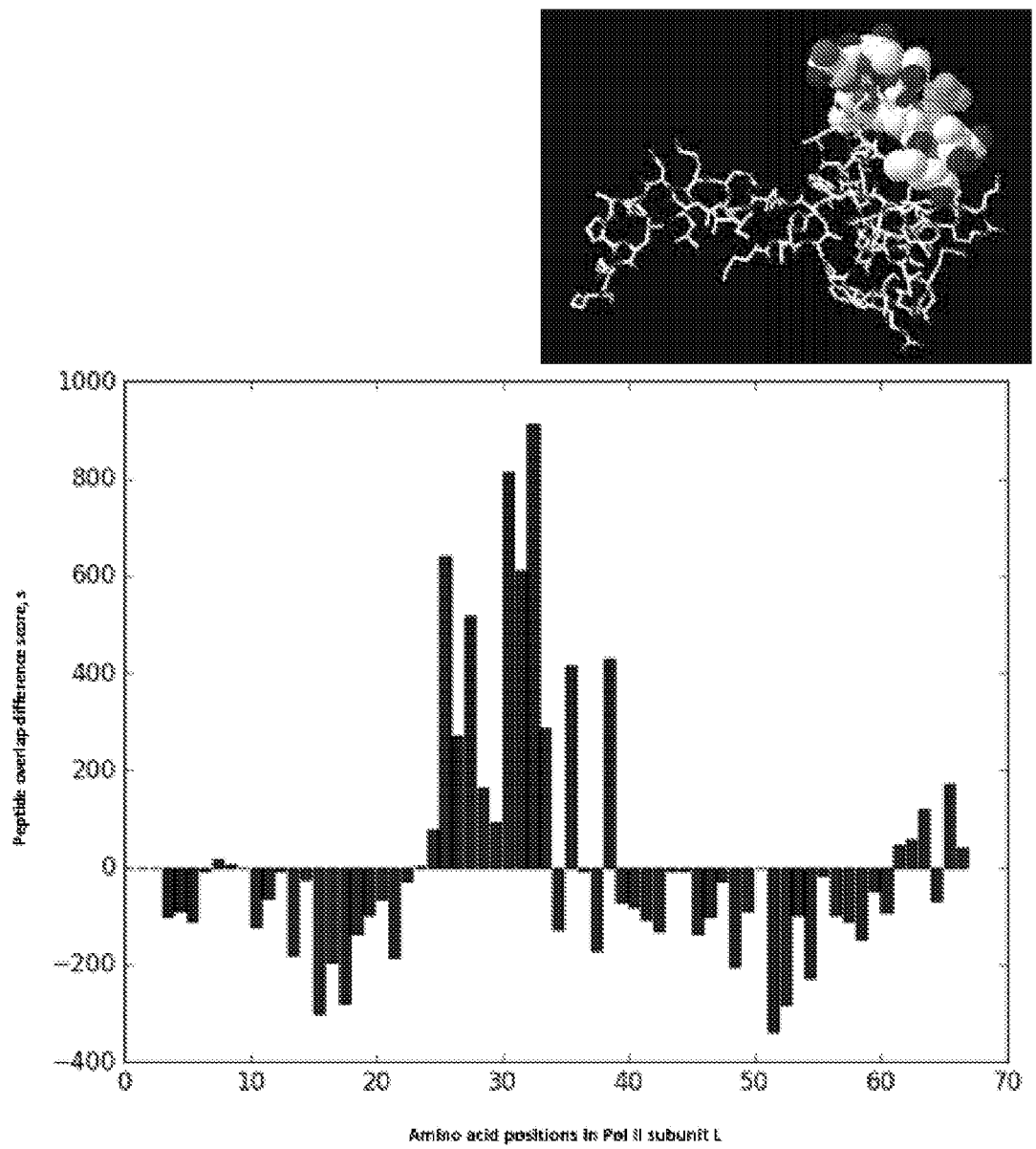

FIG. 23A shows the peptide overlap difference scores, s, calculated for the alignments of IMS peptide-motifs plotted alongside the RNA Pol II subunit L aa positions.

Figure 23B:
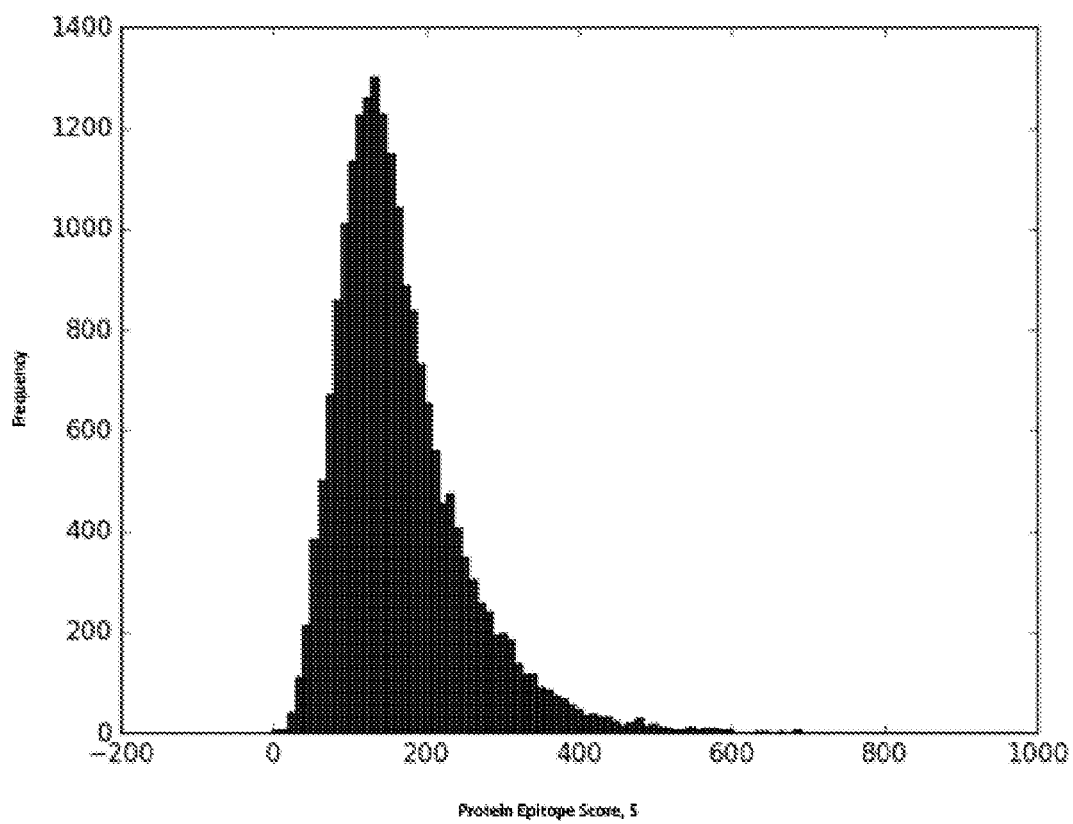

FIG. 23B shows a histogram displaying the distribution of protein epitope scores, S, for each protein in the human proteome vs the SSc vs healthy classifying peptides.

Figure 24:

FIG. 24 shows a histogram representing the frequency of alignments of IS discriminating peptides distinguishing subjects with SSc having GAVE from subjects with SSc without GAVE along the protein sequence of CCL22. FIG. 24 discloses SEQ ID NO: 98.

DETAILED DESCRIPTION OF THE INVENTION

The disclosed embodiments concern methods, apparatus, and systems for obtaining and qualifying antibody binding profiles from biological samples to diagnose autoimmune diseases relative to healthy individuals, differentially diagnose autoimmune disease relative to other autoimmune, non-autoimmune mimic diseases, and other overlap diseases, and to determine progression of autoimmune diseases.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the specification as a whole.

The terms defined immediately below are more fully described by reference to the Specification as a whole. It is to be understood that this invention is not limited to the particular methodology, protocols, and reagents described, as these may vary, depending upon the context they are used by those of skill in the art.

Definitions

The terms "condition" and "health condition" are used herein interchangeably to encompass all illnesses including diseases and disorders, but can include injuries and normal health situations, such as pregnancy, that might affect a person's health, benefit from medical assistance, or have implications for medical treatments.

The term "immunosignature" herein refers to a combination of binding signals produced by the differential binding of antibodies in a sample from a subject to an array of peptides relative to the binding of antibodies in reference sample(s) to the array of peptides.

The term "subject" herein refers to a human subject as well as a non-human subject such as a non-human mammal. Thus, various veterinary applications are contemplated in which case the subject may be a non-human mammal (e.g., a feline, a porcine, an equine, a bovine, and the like). The concepts described herein are also applicable to plants.

The term "patient sample" and "subject sample" are used interchangeably herein to refer to a sample e.g. a biological fluid sample, obtained from a patient i.e. a recipient of medical attention, care or treatment. The subject sample can be any of the samples described herein. In certain embodiments, the subject sample is obtained by non-invasive procedures e.g. peripheral blood sample.

As used herein the term "microarray system" refers to a system usually comprised of array peptides formatted on a solid planar surface like glass, plastic or silicon chip and any one or more of instruments needed to handle samples (automated robotics), instruments to read the reporter molecules (scanners), and analyze the data (bioinformatic tools).

The term "array peptide" herein refers to a peptide immobilized on a microarray.

The term "discriminating" and "differentiating" are used herein interchangeably in reference to peptides in an antibody binding profile/pattern that differentially bind antibodies in a sample from a test subject relative to a reference subject or subjects to determine the health condition of the test subject.

The term "accuracy" herein refers to the proportion of correct outcomes classified by the method.

The term "sensitivity" herein refers to the proportion of samples to be correctly identified as being positive for the condition being tested.

The term "specificity" herein refers to the proportion of samples to be correctly identified as being negative for the condition being tested.

The term "amino acid" herein refers to naturally occurring carboxy-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (tip, W), tyrosine (tyr, Y), and valine (val, V).

Detecting and diagnosing immune-mediated disorders, such as autoimmune disorders, is challenging, with patients having a difficult time receiving an accurate or correct diagnosis. In many instances, patients are often misdiagnosed with other autoimmune conditions because of the closely related nature of these diseases. There are currently no reliable bio-markers available for the detection and assessment of automimmune diseases or disorders.

For example, Systemic Sclerosis or Scleroderma (SSc) is a multisystem autoimmune disease in which there is increased fibroblast activity resulting in abnormal growth of connective tissue. SSc is difficult to diagnose or obtain a prognosis of the disease condition because of its close relationship to other similar diseases. SSc causes vascular damage and fibrosis in the skin, the gastrointestinal (GI) tract and other internal organs, and is suspected in patients with skin thickening, puffy or swollen fingers, hand stiffness, and painful distal finger ulcers. Symptoms of Raynaud's phenomenon (RP; disorder which affects blood vessels, mostly in the extremities (fingers and toes); cause blood vessels to narrow in cold and stress, resulting in numb feeling in the affected extremities) and gastroesophageal reflux are often present. FIGS. 1A and 1B depict a list of clinical manifestations of systemic sclerosis, which are heterogenous and vary as a result of the type of disease (limited or diffuse) and organ involvement.

The diagnosis of systemic scleroderma may be made on the basis of characteristic findings of cutaneous skin thickening, which may be in association with Raynaud's phenomenon and varying degrees of internal organ involvement. In early stages of the disease, Raynaud's phenomenon may be the only clinical manifestation of the disease. Nailfold capillarscopy may be helpful in these cases for determining whether Raynaud's phenomenon is primary or secondary to SSc. Diagnostic criteria for SSc as proposed by the American College of Rheumatology are listed in FIG. 2, however experts differ regarding the usefulness of these criteria, and disease manifestations are often advanced by the time patients fulfill these criteria. Additionally, the heterogeneity of clinical presentation, range of internal organ involvement, and differences in rates of disease progression make counseling and management of each individual patient's disease challenging.

Scleroderma may occur alone or in overlap syndromes with other diseases of connective tissue (such as systemic lupus erythematosus, dermatomyositis, and rheumatoid arthritis). Depending on which other diseases it is associated with, the disease state may be referred to as an "overlap syndrome". Overlap diseases associated with scleroderma may also be a mimic disease, i.e., different diseases that present with, for example, scleroderma, but cannot be readily distinguished from scleroderma symptoms.

Figure 3:
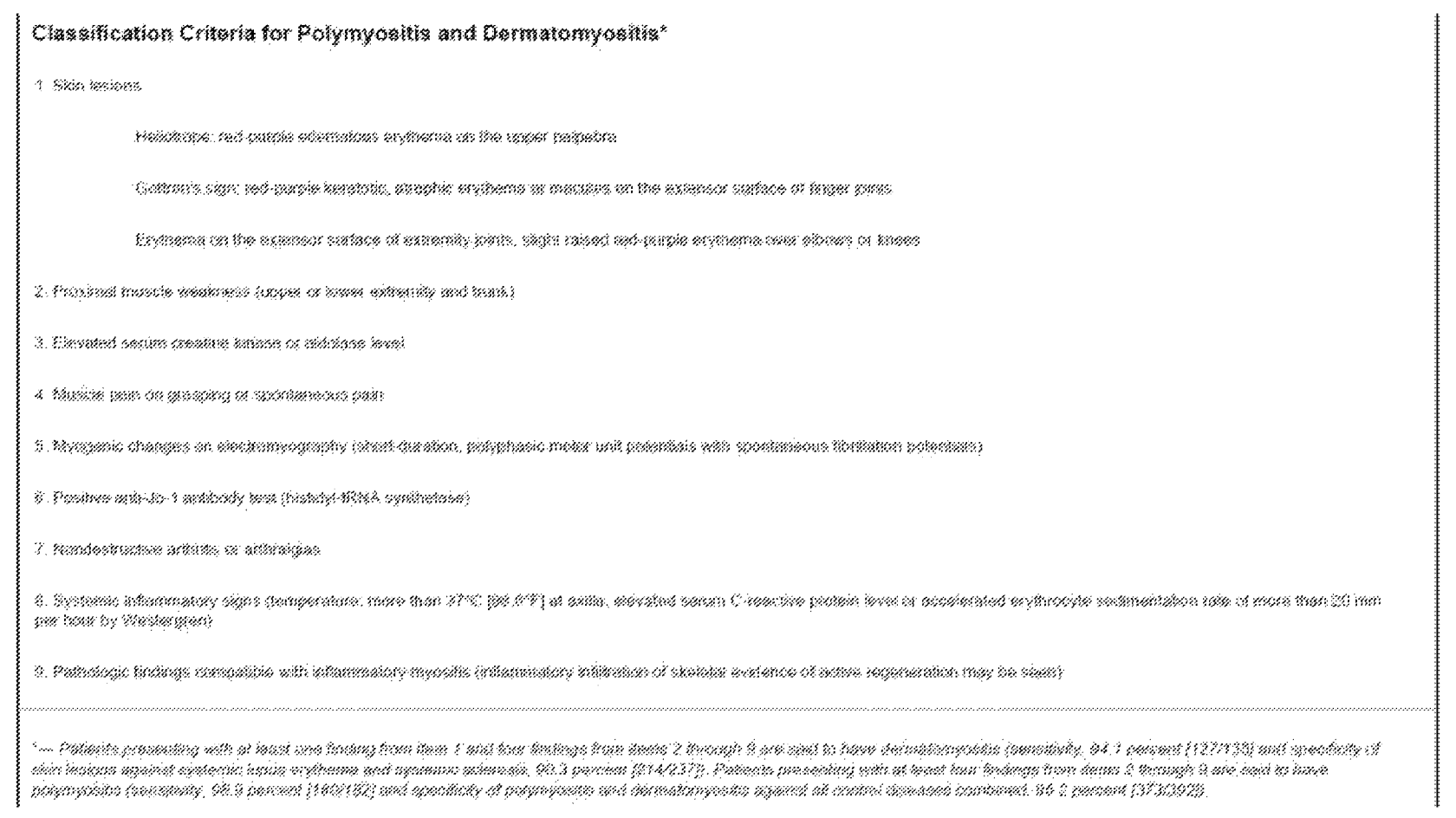

Dermatomyositis is an idiopathic inflammatory myopathy, that characteristically presents with skin manifestations. Although this condition is rare (one to 10 cases per million in adults), early diagnosis and treatment is important because of systemic complications that can increase morbidity of the disease. Polymyositis includes the inflammatory myopathy seen in these patients minus the cutaneous findings of the disease. Classification of the disease, which was first described in 1975, is seen in FIG. 3. The difficulty of diagnosing the disease from other cutaneous and connective tissue disorders such as scleroderma, makes differential diagnostic guidelines and assays important in making a correct diagnosis of the disease. Differential diagnosis of dermatomyositis includes the evaluation of whether a patient has, for example, an HIV infection, Lichen planus, polymorphous light eruption, seborrheic dermatitis, systemic lupus erythematosus, psoriasis, contact dermatitis, atopic dermatitis, trichinosis, drug effects, including penicillamine, nonsteroidal anti-inflammatory agents, hydroxylurea, pravastatin, clofibrate and ipecac, as well as the general effects of alcohol.

Accordingly, it would be useful and desirable to develop methods, assays and devices for the differential diagnosis of closely related autoimmune disorders, including dermatomyositis, SSc, myositis, systemic lupus erythematosus and other autoimmune diseases. This is especially needed because early recognition of the correct underlying disease or disorder can assist in reducing or slowing the progression of the disease. For example, interstitial lung disease develops in 20-40% of dermatomyositis patients; early recognition would contribute to improved patient care and facilitate therapeutic efforts.

Disclosed herein are methods, assays and devices that identify differential patterns of peripheral-blood antibody binding to a peptide array. Differential binding of patient samples to the array results in specific binding patterns or signatures indicative of the disease state of the patient. These binding signatures can accurately differentiate a disease activity from closely related disease activities, including but not limited to different classifications of autoimmune diseases or disorders. For example, the methods, devices and assays disclosed herein can differentiate between dermatomyositis (DM), and systemic sclerosis (SSc) and systemic lupus erythematosus (SLE), among other autoimmune diseases, including but not limited to mixed connective tissue disease (MCTD), undifferentiated connective tissue disease (UCTD), systemic lupus erythematosus (SLE), polymyositis, and localized scleroderma (morphea) and other autoimmune disorders. Additionally, the methods, devices and systems disclosed herein can distinguish signatures of patients with or without specific internal organ complications, such as interstitial lung disease (ILD), and gastric antral vascular ectasia (GAVE), which are indicative of disease progression, for example, in systemic scleroderma and dermatomyositis.

The method is predicated on the binding of the complex mixture of antibodies in a sample e.g. blood sample, to an array of peptides. The technology disclosed herein uses arrays of at least thousands of unique peptides designed from chemical sequence space to enable broad surveys of an individual's antibody binding repertoire from a small sample. Different samples comprise different mixtures of antibodies that bind different sets or combinations of array peptides. This differential binding results in specific binding patterns, herein referred to as immunosignatures (IS), that are indicative of the condition of the subject from which the sample was obtained. Typically, an immunosignature characteristic of a condition is determined relative to one or more reference immunosignatures, which are obtained from one or more different sets of reference samples obtained from one or more groups of reference subjects, each group having a different condition. For example, an immunosignature obtained from a test subject identifies the condition of the test subject when compared to immunosignatures of reference subjects with different conditions that can be induced, for example, by the occurrence of disease, drug treatment, environmental effects, and the like. Accordingly, comparison of immunosignatures from a test subject with those of reference subjects can determine the condition of the test subject. A reference group can be a group of healthy subjects, and the condition is referred to herein as a healthy condition. Healthy subjects are typically those who do not have the condition that is being tested.

In some embodiments, the method provides a differential diagnosis. Differential diagnosis is a process for removing diagnoses based on the common factors. For example, differential diagnoses distinguish mimic diseases, which are different diseases that present with symptoms that are common to other diseases that the diseases cannot be readily distinguished. These diseases are often called overlap diseases. Consequently, a correct diagnosis for such a disease can take several months or even years to determine. It typically requires a combination of medical history review, multiple physical examinations, numerous lab tests, and often scans. Typically, biomarkers for such diseases are not available, and diagnosis relies on serologic tests whose information can be attributable to other diseases. Differential diagnosis of some autoimmune diseases is particularly difficult to achieve. Examples of mimic diseases that are difficult to diagnose include without limitation autoimmune diseases, e.g. systemic lupus erythematosus, that has overlapping symptoms with rheumatoid arthritis, mixed connective tissue disease, Sjogren's syndrome, Reynaud's syndrome, scleroderma and systemic sclerosis. For example, Systemic Scleroderma (SSc) and dermatomyositis, can present with skin manifestations. The difficulty in diagnosing one of these diseases from other cutaneous and connective tissue disorders makes differential diagnostic guidelines and assays important for making the correct diagnosis.

In one aspect, a method of the invention is a method of diagnosing or determining the presence or absence of an automimmune disorder in a subject, the method comprising: a. contacting a peptide array with a first biological sample from an individual patient or subject; b. detecting binding of antibodies in the first biological sample with the peptide array to obtain a first immunosignature profile; c. contacting a peptide array with a control sample derived from one or more individuals with a known autoimmune disorder; d. detecting binding of antibody in the control sample with the peptide array to obtain a second immunosignature profile; e. comparing the first immunosignature profile to the second immunosignature profile to determine if a patient or subject has an autoimmune disease or disorder.

In one embodiment, a method is provided for making a differential diagnosis of an autoimmune disease, said method comprising (a) contacting a sample from a subject to an array of peptides comprising at least 10,000 different peptides synthesized in situ; (b) detecting the binding of antibodies present in said sample to at least 25 peptides on said array to obtain a combination of binding signals; and (c) comparing said combination of binding signals to a one or more groups of combinations of reference binding signals, wherein each of said groups of combinations of reference binding signals comprises a combination of binding signals obtained from a plurality of subjects having a different disease, thereby making said differential diagnosis, wherein the method performance is characterized by an area under the receiver operator characteristic (ROC) curve (AUC) being greater than 0.6. In some embodiments, the different disease is an autoimmune disease. In some embodiments, the diagnosis can be made between scleroderma and dermatomyositis. In other embodiments, the diagnosis differentiates between SSc and a combination of other autoimmune diseases. For example, the method can differentiate a subject having SSc from a group of reference subjects having different diseases including Mixed Connective Tissue Disease (MCTD), Undifferentiated Connective Tissue Disease (UCTD), myositis, polymyositis, systemic lupus erythomatosus, and morphea.

In another aspect, a method is provided for determining the presence of an autoimmune disease by comparing the immunosignature obtained from a subject having or suspected of having an autoimmune disease to a combination of reference binding signals obtained from a group of healthy individuals. In some embodiments, the method provided is used to diagnose a subject as having or not having an autoimmune disease, the method comprising: A method of making a diagnosis of an autoimmune disease, said method comprising: (a) contacting a sample from a subject to an array of peptides comprising at least 10,000 different peptides synthesized in situ; (b) detecting the binding of antibodies present in said sample to at least 25 peptides on said array to obtain a combination of binding signals; and (c)

comparing said combination of binding signals to a one or more groups of combinations of reference binding signals, wherein each of said groups of combinations of reference binding signals comprises a combination of binding signals obtained from a plurality of healthy subjects, thereby determining the presence or absence of the autoimmune disease in the subject. In some embodiments, the autoimmune disease is SSc. In other embodiments, the autoimmune disease is DM. In some embodiments, the method performance is characterized by an area under the receiver operator characteristic (ROC) curve (AUC) being greater than 0.6.

The binding information that characterizes the health condition from a subject sample i.e. test sample, is obtained as a combination of detectable and subsequently quantifiable binding signals that are reflective of the binding of the mixture of antibodies in the sample to a combination of the array peptides. The combination of binding signals of the antibodies in a sample from a test subject is compared to one or more combinations of binding signals that are common to groups of reference individuals having known conditions to identify combinations of binding signals that discriminate different health conditions.

Binding Assay

The IS of a subject is identified as a pattern of binding of antibodies that are bound to the array peptides. The peptide array can be contacted with the sera under any suitable conditions to promote binding of antibodies in the sera to peptides immobilized on the array. Thus, the methods of the invention are not limited by any specific type of binding conditions employed. Such conditions will vary depending on the array being used, the type of substrate, the density of the peptides arrayed on the substrate, desired stringency of the binding interaction, and nature of the competing materials in the binding solution. In a preferred embodiment, the conditions comprise a step to remove unbound antibodies from the addressable array. Determining the need for such a step, and appropriate conditions for such a step, are well within the level of skill in the art.

Any suitable detection technique can be used in the methods of the invention detecting binding of antibodies in the sera to peptides on the array to generate a disease immune profile; In one embodiment, any type of detectable label can be used to label peptides on the array, including but not limited to radioisotope labels, fluorescent labels, luminescent labels, and electrochemical labels (i.e.: ligand labels with different electrode mid-point potential, where detection comprises detecting electric potential of the label). Alternatively, bound antibodies can be detected, for example, using a detectably labeled secondary antibody.

Detection of signal from detectable labels is well within the level of skill in the art. For example, fluorescent array readers are well known in the art, as are instruments to record electric potentials on a substrate (For electrochemical detection see, for example, J. Wang (2000) Analytical Electrochemistry, Vol., 2nd ed., Wiley-VCH, New York). Binding interactions can also be detected using other label-free methods such a s SPR and mass spectrometry. SPR can provide a measure if dissociation constants and dissociation rates. The A-100 Biocore/GE instrument, for example, is suitable for this type of analysis. FLEX chips can be used to up to 400 binding reactions on the same support.

Alternatively, binding interactions between antibodies in a sample and the peptides on an array can be detected in a competition format. A difference in the binding profile of an array to a sample in the presence versus absence of a competitive inhibitor of binding can be useful in characterizing the sample.

Classification Algorithms

Analyses of the antibody binding signal data i.e. immunosignaturing, and the diagnosis derived therefrom are typically performed using various computer algorithms and programs. The antibody binding pattern produced by the labeled secondary antibody is scanned using, for example, a laser scanner. The images of the binding signals acquired by the scanner can be imported and processed using software such as the GenePix Pro 8 software (Molecular Devices, Santa Clara, Calif.), to provide tabular information for each peptide, for example, in a continuous value ranging from 0-65,000. Tabular data can be imported and statistical analysis performed using, for example, into Agilent's GeneSpring 7.3.1 (Agilent, Santa Clara, Calif.).

Peptides displaying differential signaling patterns between samples obtained from subjects with different health conditions can be identified using known statistical tests such as a Welch-corrected T-test or ANOVA. For example, patterns of antibody binding to array peptides can be obtained for a set of samples comprising samples from a group of test patients e.g. subjects having a disease, and samples form a group of reference subjects e.g. healthy patients. Binding signal information is compared, and the statistical analyses are applied to select the differentiating peptides that distinguish the two conditions i.e. the test and reference groups at predetermined stringency levels. A list of the most differentiating peptides can be obtained by ranking the peptides according to their p-value. Differentiating peptides can be ranked and identified as having p-values of at least $10^{-30}$, at least $10^{-29}$, at least $10^{-28}$, at least $10^{-27}$, at least $10^{-26}$, at least $10^{-25}$, at least $10^{-24}$, at least $10^{-23}$, at least $10^{-22}$, at least $10^{-21}$, at least $10^{-20}$, at least $10^{-19}$, at least $10^{-18}$, at least $10^{-17}$, at least $10^{-16}$, at least $10^{-15}$, at least $10^{-14}$, at least $10^{-13}$, at least $10^{-12}$, at least $10^{-11}$, at least $10^{-10}$, at least $10^{-9}$, at least $10^{-8}$, at least $10^{-7}$, at least $10^{-6}$, or at least $10^{-5}$.

Alternatively, binding signal information of the discriminating peptides selected following statistical analysis can be subsequently imported into a machine learning algorithm to obtain a model that classifies the antibody profile data with the desired accuracy, sensitivity and specificity, and determine presence or absence of disease, severity of disease, disease progression, and other applications described elsewhere herein. A basic classification algorithm, Linear Discriminant Analysis (LDA) is widely used in analyzing biomedical data in order to classify two or more disease classes. LDA can be, for example, a classification algorithm. A more complex classification method, Support Vector Machines (SVM), uses mathematical kernels to separate classes by a hyperplane, projecting the original predictors to higher-dimensional spaces. Some common kernels include linear, polynomial, sigmoid or radial basis functions. A comparative study of common classifiers described in the art is described in (Kukreja et al, BMC Bioinformatics. 2012; 13: 139). Other algorithms for data analysis and predictive modeling based on data of antibody binding profiles include Bayes Net, Logistic Regression, Simple Logistic, Multilayer Perceptron, KNearest neighbor, K Star, Attribute Selected Classifier (ACS), Classification via clustering, Classification via Regression, Hyper Pipes, Voting Feature Interval Classifier, J48 (Java implementation of C4.5 algorithm), Random Trees, and Random Forest.

In some embodiments, antibody binding profiles are obtained from a training set of samples, which are used to identify the most discriminative combination of peptides by applying an elimination algorithm based on SVM analysis. The accuracy of the algorithm at various levels of significance can be determined by cross-validation. To generate and evaluate antibody binding profiles of a feasible number of discriminating peptides, multiple models can be built, using a plurality of discriminating peptides to identify the best performing model. In some embodiments, at least 25, at least 50, at least 75, at least 100, at least 200, at least 300, at least 400, at least 500, at least 750, at least 1000, at least 1500, at least 2000, at least 3000, at least 4000, at least 5000, at least 6000, at least 7000, at least 8000, at least 9000, at least 10,000, at least 11,000 at least 12,000 at least 13,000 at least 14,000 at least 15,000 at least 16,000 at least 17,000 at least 18,000 at least 19,000 at least 20,000 or more differentiating peptides are used to train a specific disease-classifying model. In some embodiments at least 0.00001%, at least 0.0001%, at least 0.0005%, at least 0.001%, at least 0.005%, at least 0.01%, at least 0.05%, at least 0.1%, at least 0.5%, at least 1.0%, at least 2%, at least 3%, at least 4%, at least 5%, at least 10%, at least 20%, at least 30%, at least 40%, at least 50%, at least 60%, at least 70%, at least 80%, at least 90%, at least 95%, or at least 99% of the total number of peptides on the array are differentiating peptides, and the corresponding binding signal information is used to train a specific condition-classifying model. In some embodiments, the signal information obtained for all of the peptides on the array is used to train the condition-specific model.

Multiple models comprising different numbers of differentiating peptides can be generated, and the performance of each model can be evaluated by a cross-validation process. An SVM classifier can be trained and cross-validated by assigning each sample of a training set of samples to one of a plurality of cross-validation groups. For example, for a four-fold cross-validation, each sample is assigned to one of four cross-validation groups such that each group comprises test and control i.e. reference samples; one of the cross-validation groups e.g. group 1, is held-out, and an SVM classifier model is trained using the samples in groups 2-4. Peptides that discriminate test cases and reference samples in the training group are analyzed and ranked by p value; the top k peptides are then used as predictors for the SVM model. To elucidate the relationship between the number of input predictors and model performance, and to guard against overfitting, the sub=loop is repeated for a range of k, e.g. 25, 50, 100, 250, 1000, 200, 3000 top peptides or more. Predictions i.e. classification of samples in group 1 are made suing the model generated using groups 2-4. Models for each of the four groups are generated, and the performance (AUC, sensitivity and/or specificity) is calculated using all the predictions from the 4 models using signal binding data from true disease samples. The cross-validation steps are repeated at least 100 times, and the average performance is calculated relative to a confidence interval e.g. 95%. Diagnostic visualization can be generated using e.g. volcano plots, ROC (receiver operating characteristic) curves, and model performance relative to the number of input peptides.

An optimal model based on antibody binding information to a set of discriminating input peptides (list of the most discriminating peptides, k) is selected and used to predict the disease status of a test set. The performance of different classifiers is determined using a validation set, and using a test set of samples, performance characteristics such as accuracy, sensitivity, specificity, and F-measure are obtained from the model having the greatest performance. Different sets of discriminating peptides are identified to distinguish different conditions. Accordingly, an optimal model based on a set of the most discriminating input peptides is established for each of the health conditions to be determined in patients.

In some embodiments, the resulting classification performance can be provided as a Radio Operator Characteristic curve (ROC). Specificity, sensitivity, and accuracy metrics of the classification can be determined by the area under the ROC (AUC). In some embodiments, the method determines/classifies the health condition of a subject with a method performance or accuracy characterized by an area under the receiver operator characteristic (ROC) curve (AUC) being greater than 0.60. In other embodiments, the method performance characterized by an area under the receiver operator characteristic (ROC) curve (AUC) being greater 0.70, greater than 0.80, greater than 0.90, greater than 0.95, method performance characterized by an area under the receiver operator characteristic (ROC) curve (AUC) being greater than 0.97, method performance characterized by an area under the receiver operator characteristic (ROC) curve (AUC) being greater than 0.99. In other embodiments, the method performance is characterized by an area under the receiver operator characteristic (ROC) curve (AUC) ranging from 0.60 to 0.70, 0.70 to 0.79, 0.80 to 0.89, or 0.90 to 1.0. In yet other embodiments, method performance is expressed in terms of sensitivity, specificity, predictive values or likelihood ratios (LRs).

In some embodiments, the method has a sensitivity of at least 60%, for example 65%, 70%, 75%, 80%, 85%, 90%, 91%, 92%, 93%, 94%, 95%, 96%, 97%, 98%, 99% or 100% sensitivity.

In other embodiments, the method has a specificity of at least 60%, for example 65%, 70%, 75%, 80%, 85%, 90%, 91%, 92%, 93%, 94%, 95%, 96%, 97%, 98%, 99% or 100% specificity.

Having established an optimal classifier model for a particular health condition or disease, the method is applied to determine the health condition of a subject. A sample is obtained from a subject for whom a diagnosis is desired. The sample is contacted to the array of peptides, and the binding signals resulting from the binding of the antibodies in the subject sample to a plurality of peptides on the array are detected e.g. using a scanner, and are imported into software to compare the binding signal resulting from the binding antibodies in the subject sample to the discriminating peptides previously identified for the optimal classifying model. An overall score that accounts for differences in signals between the discriminating peptides of the model and the binding signals of the corresponding peptides obtained from the sample is provided, and an output indicating presence or absence of disease is given.

In some embodiments, the condition of a subject is determined relative to that of one or more reference groups with a method performance characterized by an area under the receiver operator characteristic (ROC) curve (AUC) being greater 0.70, greater than 0.80, greater than 0.90, greater than 0.95, method performance characterized by an area under the receiver operator characteristic (ROC) curve (AUC) being greater than 0.97, method performance characterized by an area under the receiver operator characteristic (ROC) curve (AUC) being greater than 0.99. In other embodiments, the method performance is characterized by an area under the receiver operator characteristic (ROC) curve (AUC) ranging from 0.60 to 0.70, 0.70 to 0.79, 0.80 to 0.89, or 0.90 to 1.0. In yet other embodiments, method performance is expressed in terms of sensitivity, specificity, predictive values or likelihood ratios (LRs).

In some embodiments, the method has a sensitivity of at least 60%, for example 65%, 70%, 75%, 80%, 85%, 90%, 91%, 92%, 93%, 94%, 95%, 96%, 97%, 98%, 99% or 100% sensitivity.

In other embodiments, the method has a specificity of at least 60%, for example 65%, 70%, 75%, 80%, 85%, 90%, 91%, 92%, 93%, 94%, 95%, 96%, 97%, 98%, 99% or 100% specificity.

Discriminating peptides can be characterized by enrichment of one or more particular amino acids, and/or by enrichment of one or more sequence motifs. Enrichment of amino acid and motif content is relative to the corresponding total amino acid and motif content of all the peptides in the array library. Enriched motifs were identified from the list of significant peptides unless that list was less than 100 peptides long, in which case the top 500 peptides based on the p-value associated with a Welch's t-test were used. The different n-mers in this list of peptides was compared to the same sized n-mers in the total library to determine if any were enriched. Fold enrichment is calculated by determining the number of times a motif (e.g. ABCD) occurs in the list divided by the number of times the motif (ABCD) occurs in the library. This value is further divided by the relative number of times the motif type (e.g., tetramers) appears in the library (i.e., total number of all tetramers in the list divided by the total number of tetramers in the library). This Fold Enrichment (E) calculation can be represented by:

$$E=(m/M)/(t/T)$$

where m is the number of times the motif occurs as part of the discriminating peptide list; M is the total number of times the motif occurs in the library; t is the number of times the motif type appears in the list; and T is the number of times the motif occurs in the library. Fold enrichment can also be reported as Percent enrichment, i.e., "Enrichment value" multiplied by 100.

In some embodiments, the discriminating peptides of the immunosignature binding patterns that distinguish a subject with an autoimmune disease from reference healthy subjects in diagnosing or detecting an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, the autoimmune disease is SSc or DM. In some embodiments, discriminating peptides that distinguish SSc from healthy reference subjects are enriched in one or more of tyrosine, lysine, arginine, phenylalanine, serine, tryptophan, glycine, and alanine. In some embodiments, discriminating peptides that distinguish DM from healthy reference subjects are enriched in one or more of tyrosine, tryptophan, serine, glycine, aspartic acid, and phenylalanine.

In some embodiments, the discriminating peptides of the immunosignature binding patterns for diagnosing or detecting an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In some embodiments, discriminating peptides that distinguish SSc from healthy reference subjects are enriched in one or more of motifs provided in FIG. 5A. In some embodiments, discriminating peptides that distinguish DM from healthy reference subjects are enriched in one or more of motifs provided in FIG. 17A.

In some embodiments, the discriminating peptides of the immunosignature binding patterns for providing a differential diagnosis of autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, the differential diagnosis is made between SSc and DM. In some embodiments, discriminating peptides that distinguish SSc from DM reference subjects are enriched in one or more of serine, glycine, tyrosine, arginine, alanine, glutamine and valine.

In some embodiments, the discriminating peptides of the immunosignature binding patterns for providing a differential diagnosis of autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In some embodiments, discriminating peptides that distinguish SSc from DM subjects are enriched in one or more of motifs provided in FIG. 13A.

In some embodiments, differential diagnosis can be made for a subject relative to a group of reference subjects having a plurality of different autoimmune diseases. In some embodiments, the differential diagnosis is made relative to a group of subjects having other autoimmune diseases comprising Mixed Connective Tissue Disease (MCTD), Undifferentiated Connective Tissue Disease (UCTD), myositis, polymyositis, systemic lupus erythomatosus, and morphea. The discriminating peptides of the immunosignature binding patterns for making a differential diagnosis of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the discriminating peptides that identify the autoimmune disease. In preferred embodiments, the autoimmune disease is SSc or DM. Discriminating peptides that distinguish a subject with SSc from reference subjects each having one of a plurality of different diseases are enriched I one or more of aspartic acid, glutamic acid, proline, valine, glycine, and serine.

Discriminating peptides that distinguish a subject with DM from reference subjects each having one of a plurality of different diseases are enriched I one or more of lysine, histidine, serine, arginine, glutamic acid, alanine, and glycine.

In some embodiments, the discriminating peptides of the immunosignature binding patterns for providing a differential diagnosis of autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In some embodiments, discriminating peptides that distinguish SSc from the group of reference subjects each having one of a plurality of different autoimmune diseases are enriched in one or more of motifs provided in FIG. 7A. In some embodiments, discriminating peptides that distinguish DM from the group of reference subjects each having one of a plurality of different autoimmune diseases are enriched in one or more of motifs provided in FIG. 19A.

Comparison of the disease immune profile to a reference e.g. healthy immune profile and identifying differentially bound peptides can reveal that at least some discriminating peptides bind more antibody in the disease immune profile compared to the reference; and/or peptides that at least some discriminating peptides bind less antibody in the disease immune profile compared to the reference. Accordingly, in some embodiments, a method of the invention is a method for diagnosing or detecting an autoimmune disorder, the method comprising: a) contacting a peptide array with a first biological sample from a patient or subject; b) detecting binding of antibodies in the first biological sample with the peptide array to obtain a first immunosignature profile; c) contacting a peptide array with a control sample derived from an individual with a known autoimmune disease or disorder; d) detecting binding of antibody in the control sample with the peptide array to obtain a second immunosignature profile; e) comparing the first immunosignature profile to the second immunosignature profile and identifying differentially bound peptides that either bind less or more antibody in the first immunosignature profile as compared to the second immunosignature profile; and 0 determining if the patient or subject has an autoimmune disease or disorder.

The milder form of scleroderma is generally limited to areas of skin are thick; usually just the fingers and/or face. Every person with scleroderma can have a different pattern of symptoms including calcinosis, which is the deposit of calcium under the ski and tissues, Raynaud's phenomenon, esophageal dysmotility, sclerodactily, and telangiectasias. However, scleroderma can progress to a diffuse disease which involves more areas and thickening of the skin, and can include the skin of the arms, legs, and trunk. The tightened skin makes it difficult to bend fingers, hands, and other joints. There is sometimes inflammation of the joints, tendons and muscles. Tight skin on the face can reduce the size of a person's mouth and make good dental care very important. The skin can lose or gain pigment; making areas of light or dark skin. Some people lose hair on the limbs, sweat less, and develop dry skin because of skin damage. More importantly, diffuse scleroderma can have associated involvement of internal organs such as the gastrointestinal tract, heart, lungs, or kidneys. The degree of organ involvement is highly variable—some get none at all and other patients organs may be badly affected. Discriminating peptides can also distinguish different states reflective of the progression of a disease e.g. an autoimmune disease. For example, progression of SSc can manifest in interstitial lung disease (ILD). In some case, SSc can progress to manifest in gastric antral vascular ectasia (GAVE). In other cases, SSc can progress to involve the kidneys. Complications relating to ILD and GAVE can also occur in other mimic autoimmune disease e.g. DM.

In another aspect, a method of the invention is a method of determining the disease state or progression of an autommmune disorder in a subject, the method comprising: a. contacting a peptide array with a first biological sample from an individual patient or subject with a known autoimmune disorder; b. detecting binding of antibodies in the first biological sample with the peptide array to obtain a first immunosignature profile; c. contacting a peptide array with a control sample derived from one or more individuals with a known stage of an autoimmune disorder; d. detecting binding of antibody in the control sample with the peptide array to obtain a second immunosignature profile; e. comparing the first immunosignature profile to the second immunosignature profile to determine a disease stage or progression of a patient or subject with the autoimmune disease or disorder.

In some embodiments, the assays, methods and devices provided can determine disease progression in a subject known to have an autoimmune disease. The method comprising: (a) contacting a sample from a subject to an array of peptides comprising at least 10,000 different peptides synthesized in situ; (b) detecting the binding of antibodies present in the sample to at least 25 peptides on said array to obtain a first combination of binding signals; and (c) comparing the first combination of binding signals to at least a second combination of reference binding signals, wherein the second combination of reference binding signals comprises a combination of binding signals obtained from a reference group comprising a plurality of subjects having a clinical manifestation indicative of progression of said autoimmune disease, thereby making said differential diagnosis, wherein the method performance is characterized by an area under the receiver operator characteristic (ROC) curve (AUC) being greater than 0.6. In some embodiments, disease progression is determined in a subject having SSC accompanied by ILD. In other embodiments, progression is determined in a subject having SSC accompanied by ILD. In yet other embodiments, progression is determined in a subject having DM accompanied by ILD.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, determination of disease progression is made between in subjects with SSc, and the progression is determined in subjects with ILD and/or GAVE. In some embodiments, discriminating peptides that determine disease progression in subjects with SSc and ILD relative to subjects with SSC without ILD are enriched in one or more of proline, arginine, lysine, histidine, and aspartic acid. In other embodiments, discriminating peptides that determine disease progression in subjects with SSc and GAVE relative to subjects with SSC without GAVE are enriched in one or more of arginine, tyrosine, serine, histidine, lysine, and phenylalanine.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In preferred embodiments, determination of disease progression is made between in subjects with SSc, and the progression is determined in subjects with ILD and/or GAVE. In some embodiments, discriminating peptides that determine disease progression in subjects with SSc and ILD relative to subjects with SSC without ILD are enriched in one or more of motifs provided in FIG. 15A. In other embodiments, discriminating peptides that determine disease progression in subjects with SSc and GAVE relative to subjects with SSC without GAVE are enriched in one or more of motifs provided in FIG. 11A.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, determination of disease progression is made between in subjects with SSc without renal crisis, and the progression is determined in subjects with SSc having renal crisis. In some embodiments, discriminating peptides that determine disease progression in subjects with SSc without renal crisis relative to subjects with SSC without renal crisis are enriched in one or more of proline, aspartic acid and glutamic acid.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, determination of disease progression is made between in subjects with SSc without renal crisis, and the progression is determined in subjects with SSc having renal crisis. In some embodiments, discriminating peptides that determine disease progression in subjects with SSc and renal crisis relative to subjects with SSC without renal crisis are enriched in one or more of motifs provided in FIG. 9A.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, determination of disease progression is made between in subjects with DM, and the progression is determined in subjects with ILD and/or GAVE. In some embodiments, discriminating peptides that determine disease progression in subjects with DM and ILD relative to subjects with DM without ILD are enriched in one or more of proline, aspartic acid, glutamic acid, serine, glycine, and glutamine.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, determination of disease progression is made between in subjects with DM, and the progression is determined in subjects with ILD and/or GAVE. In some embodiments, discriminating peptides that determine disease progression in subjects with DM and ILD relative to subjects with DM without ILD are enriched in one or more of motifs provided in FIG. 21A.

As described for the method of diagnosing and differentially diagnosing an autoimmune disease, comparison of the disease immune profile to a reference that reflects a progression of the disease e.g. disease immune profile of a subject having organ involvement, and identifying differentially bound peptides can reveal that at least some discriminating peptides bind more antibody in the disease immune profile compared to the reference; and/or peptides that at least some discriminating peptides bind less antibody in the disease immune profile compared to the reference. In some embodiments, a method of the invention is a method for determining the disease state or progression of an autoimmune disorder, the method comprising: a) contacting a peptide array with a first biological sample from a patient or subject with an autoimmune disease or disorder; b) detecting binding of antibodies in the first biological sample with the peptide array to obtain a first immunosignature profile; c) contacting a peptide array with a control sample derived from an individual with a known stage or state of an autoimmune disease or disorder; d) detecting binding of antibody in the control sample with the peptide array to obtain a second immunosignature profile; e) comparing the first immunosignature profile to the second immunosignature profile and identifying differentially bound peptides that either bind less or more antibody in the first immunosignature profile as compared to the second immunosignature profile; and 0 determining the disease state or progression of the patient or subject with the autoimmune disease or disorder.

Autoimmune Diseases

The assays, methods and devices provided can be utilized to diagnose any autoimmune disease, provide a differential diagnosis of an autoimmune disease relative to other autoimmune diseases, non-autoimmune mimic diseases, as well as other overlap diseases, determine the progression of the autoimmune disease, score the activity of the autoimmune disease, identify candidate targets for evaluation as therapeutics for the treatment of the autoimmune disease, and stratifying patients in clinical trials based on predicted responses to therapy.

Non-limiting examples of autoimmune diseases or disorders that can be diagnosed, monitored, prevented, treated, or used for identifying target therapeutics according to the assays, methods and devices provided include: systemic lupus erythematosus (SLE) (e.g., systemic lupus erythematosus, discoid lupus, drug-induced lupus, neonatal lupus), rheumatoid arthritis, Sjogren's disease, multiple sclerosis (MS), inflammatory bowel disease (IBD) e.g., Crohn's disease, ulcerative colitis, collagenous colitis, lymphocytic colitis, ischemic colitis, diversion colitis, Behcet's syndrome, infective colitis, indeterminate colitisinterstitial cystitis, psoriatic arthritis, scleroderma (SSc), type I diabetes, Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), chronic obstructive pulmonary disease (COPD), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft Versus Host Disease (GVHD) e.g. rejection of kidney, lung, liver or heart transplant, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Interstitial cystitis (IC), Juvenile arthritis, Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lyme disease chronic, Meniere's disease, Microscopic polyangiitis (MPA), Mixed connective tissue disease (MCTD), Mooren's ulcer, Mucha-Habermann disease, Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Pure red cell aplasia (PRCA), Pyoderma angrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/ Giant cell arteritis, Thrombocytopenic purpura (TTP), Tolosa-Hunt syndrome (THS), Transverse myelitis, Ulcerative colitis (UC), Undifferentiated connective tissue disease (UCTD), Uveitis, Vasculitis, Vitiligo, and/or Wegener's granulomatosis (now termed Granulomatosis with Polyangiitis (GPA).

Samples

The samples that are utilized according to the methods provided can be any biological samples. For example, the biological sample can be a biological liquid sample that comprises antibodies. Suitable biological liquid samples include, but are not limited to blood, plasma, serum, sweat, tears, sputum, urine, stool water, ear flow, lymph, saliva, cerebrospinal fluid, ravages, bone marrow suspension, vaginal flow, transcervical lavage, synovial fluid, aqueous humor, amniotic fluid, cerumen, breast milk, broncheoalveolar lavage fluid, brain fluid, cyst fluid, pleural and peritoneal fluid, pericardial fluid, ascites, milk, pancreatic juice, secretions of the respiratory, intestinal and genitourinary tracts, amniotic fluid, milk, and leukophoresis samples. A biological sample may also include the blastocyl cavity, umbilical cord blood, or maternal circulation which may be of fetal or maternal origin. In some embodiments, the sample is a sample that is easily obtainable by non-invasive procedures e.g. blood, plasma, serum, sweat, tears, sputum, urine, sputum, ear flow, or saliva. In certain embodiments the sample is a peripheral blood sample, or the plasma or serum fractions of a peripheral blood sample. As used herein, the terms "blood," "plasma" and "serum" expressly encompass fractions or processed portions thereof.

Because of its minimally invasive accessibility and its ready availability, blood is preferred, a human body fluid that is routinely measured and collected in clinical practice. Moreover, blood perfuses all body tissues and its composition is therefore relevant as an indicator of the over-all physiology of an individual. In some embodiments, the biological sample that is used to obtain an immunosignature/ antibody binding profile is a blood sample. In other embodiments, the biological sample is a plasma sample. In yet other embodiments, the biological sample is a serum sample. In yet other embodiments, the biological sample is a dried blood sample. The biological sample may be obtained through a third party, such as a party not performing the analysis of the antibody binding profiles, and/or the party performing the binding assay to the peptide array. For example, the sample may be obtained through a clinician, physician, or other health care manager of a subject from which the sample is derived. Alternatively, the biological sample may be obtained by the party performing the binding assay of the sample to a peptide array, and/or the same party analyzing the antibody binding profile/IS. Biological samples that are to be assayed, can be archived (e.g., frozen) or otherwise stored in under preservative conditions.

The term "patient sample" and "subject sample" are used interchangeably herein to refer to a sample e.g. a biological fluid sample, obtained from a patient i.e. a recipient of medical attention, care or treatment. The subject sample can be any of the samples described herein. In certain embodiments, the subject sample is obtained by non-invasive procedures e.g. peripheral blood sample.

A antibody binding profile of circulating antibodies in a biofluid sample can be obtained according to the methods provided using limited quantities of sample. For example, peptides on the array can be contacted with a fraction of a milliliter of blood to obtain an antibody binding profile comprising a sufficient number of informative peptide-protein complexes to identify the health condition of the subject.

In some embodiments, the volume of biological sample that is needed to obtain an antibody binding profile is less than 10 ml, less than 5 ml, less than 3 ml, less than 2 ml, less than 1 ml, less than 900 ul, less than 800 ul, less than 700 ul, less than 600 ul, less than 500 ul, less than 400 ul, less than 300 ul, less than 200 ul, less than 100 ul, less than 50 ul, less than 40 ul, less than 30 ul, less than 20 ul, less than 10 ul, less than 1 ul, less than 900 nl, less than 800 nl, less than 700 nl, less than 600 nl, less than 500 nl, less than 400 nl, less than 300 nl, less than 200 nl, less than 100 nl, less than 50 nl, less than 40 nl, less than 30 nl, less than 20 nl, less than 10 nl, or less than 1 nl. In some embodiments, the biological fluid sample can be diluted several fold to obtain an antibody binding profile. For example, a biological sample obtained from a subject can be diluted at least by 2-fold, at least by 4-fold, at least by 8-fold, at least by 10-fold, at least by 15-fold, at least by 20-fold, at least by 30-fold, at least by 40-fold, at least by 50-fold, at least by 100-fold, at least by 200-fold, at least by 300-fold, at least by 400-fold, at least by 500-fold, at least by 600-fold, at least by 700-fold, at least by 800-fold, at least by 900-fold, at least by 1000-fold, at least by 5000-fold, or at least by 10,000-fold. Antibodies present in the diluted serum sample, and are considered significant to the health of the subject, because if antibodies remain present even in the diluted serum sample, they must reasonably have been present at relatively high amounts in the blood of the patient.

An example of detecting a disease in a subject according to the methods described herein is given in the Examples. The examples demonstrate that correct diagnosis of scleroderma was provided using a mere 100 microliters of serum or of plasma.

Identifying Candidate Target Proteins

The immunosignature obtained can then be used for identifying candidate therapeutic targets and developing treatments for the individual against the identified autoimmune disorder according to the methods and devices disclosed herein. In another aspect, the differential binding of antibodies in samples from subjects having two or more different health conditions identifies discriminating peptides on the array can be analyzed, for example, by comparing the sequence of one or more discriminating peptides that distinguish between two or more health conditions in the array sequences in a protein database to identify a candidate target protein. In some embodiments, splaying the antibody repertoire out on an array of peptides (immunosignaturing, IMS) and comparing samples from diseased subjects to samples from healthy reference subjects or subjects with other diseases or conditions, the discriminating peptides can be identified to reveal the proteins recognized i.e. bound by the antibodies. For example, the peptides can be identified with informatics methods.

In cases where the informatics cannot identify a putative match, such as in the case of discontinuous epitopes, the informative peptide can be used as an affinity reagent to purify reactive antibody. Purified antibody can then be used in standard immunological techniques to identify the target.

Having diagnosed a condition, the appropriate reference proteome can be queried to relate the sequences of the discriminating peptides bound by the antibodies in a sample. Reference proteomes have been selected among all proteomes (manually and algorithmically, according to a number of criteria) to provide broad coverage of the tree of life. Reference proteomes constitute a representative cross-section of the taxonomic diversity to be found within UniProtKB at http://www.uniprot.org/proteomes/?query=reference: yes Reference proteomes include the proteomes of well-studied model organisms and other proteomes of interest for biomedical and biotechnological research. Species of particular importance may be represented by numerous reference proteomes for specific ecotypes or strains of interest. Examples of proteomes that can be queried include without limitation the human proteome, and proteomes from other mammals, non-mammal animals, viruses, bacteria and protozoan parasites. Additionally, other compilations of proteins that can be queried include without limitation lists of disease-relevant proteins, lists of proteins containing known or unknown mutations (including single nucleotide polymorphisms, insertions, substitutions and deletions), lists of proteins consisting of known and unknown splice variants, or lists of peptides or proteins from a combinatorial library (including natural and unnatural amino acids). In some embodiments, the proteome that can be queried using discriminating peptides include without limitation the human proteome RefSeq release 84, corresponding to human genome build GrCh38 (https://www.ncbi.nlm.nih.gov/refseq/), compiled Mar. 10, 2016, using the longest transcript variant for each unique gene ID.

Software for aligning single and multiple proteins to proteins in a proteome or protein list include without limitation BLAST, CS-BLAST, CUDAWS++, DIAMOND, FASTA, GGSEARCH (GG or GL), Genoogle, HMMER, H-suite, IDF, KLAST, MMseqs2, USEARCH, OSWALD, Parasail, PSI-BLAST, PSI Protein, Sequilab, SAM, SSEARCH, SWAPHI, SWIMM, and SWIPE.

Alternatively, sequence motifs that are enriched in the discriminating peptides relative to the motifs found in the entire peptide library on the array can be aligned to a full-length protein or protein fragment in a proteome to identify target proteins that can be validated as possible therapeutic targets for the treatment of the condition. Discriminating peptides are aligned to the longest available transcript in the proteome database. Online databases and search tools for identifying protein domains, families and functional sites are available e.g. Prosite at ExPASy, Motif Scan (MyHits, SIB, Switzerland), Interpro 5, MOTIF (GenomeNet, Japan), and Pfam (EMBL-EBI).

In some embodiments, the alignment method can be any method for mapping amino acids of a query sequence onto a longer protein sequence, including BLAST (Altschul, S. F. & Gish, W. [1996] "Local alignment statistics." Meth. Enzymol. 266:460-480), the use of compositional substitution and scoring matrices, exact matching with and without gaps, epitope prediction, antigenicity prediction, hydrophobicity prediction, surface accessibility prediction. For each approach, a canonical or modified scoring system can be used, with the modified scoring system optimized to correct for biases in the peptide library composition. In some embodiments, a modified BLAST alignment is used, requiring a seed of 3 amino acids with a gap penalty of 4, with a scoring matrix of BLOSUM62 (Henikoff, J. G. Amino acid substitution matrices from protein blocks. *Proc. Natl. Acad. Sci. USA* 89, 10915-10919 [1992]) modified to reflect the amino composition of the array (States, D. J., Gish, W., Altschul, S. F. [1991] "Improved sensitivity of nucleic acid database searches using application-specific scoring matrices." Methods 3:66-70.) The number of seed amino acids and gap penalties are easily discerned by one of skill in the art. These modifications can include increasing the score of degenerate substitutions, remove penalties for amino acids absent from the array and score all exact matches equally.

The discriminating peptides that can be used to identify candidate biomarker proteins according to the method provided, are chosen according to their ability to distinguish between two or more different health conditions. Accordingly, discriminating peptides can be chosen at a predetermined statistical stringency, e.g. by p-value, for the probability of discriminating between two or more conditions; by differences in the relative binding signal intensity changes between two or more conditions; by their intensity rank in a single condition; by their coefficients in a machine learning model trained against two or more conditions e.g. the AUC, or by their correlation with one or more study parameters.

The method provided for identifying candidate protein biomarkers utilizes the homology between the discriminating peptides and proteins of a proteome or other protein list, while correcting for the potential oversampling from lists comprising larger peptides relative to lists.

The query peptides are the discriminating peptides capable of distinguishing two or more different health conditions to be aligned can be chosen based on their p-value for discrimination between two or more conditions, their relative intensity changes between two or more conditions, by their intensity rank in a single condition, by their coefficients in a machine learning model trained against two or more conditions, or by their correlation with one or more study parameters.

Having identified the set of discriminating peptides and the proteome or protein list to be queried, all the discriminating peptides are aligned with the longest available protein transcript in the proteome or protein list, and peptides having a positive BLAST score are identified. For each of the proteins to which discriminating peptides are aligned, the scores for the BLAST-positive peptides in the alignment are assembled into a matrix e.g. modified BLOSUM62. These modifications can include increasing the score of degenerate substitutions, remove penalties for amino acids absent from the array and score all exact matches equally.

Each row of the matrix corresponds to an aligned peptide and each column corresponds to one of the consecutive amino acids that comprise this protein, with gaps and deletions allowed within the peptide rows to allow for alignment to the protein.

Using the modified BLAST scoring matrix described above, each position in the matrix receives the score for paired amino acids of the peptide and protein in that column. Then, for each amino acid in the protein, the corresponding column is summed to create an "overlap score" that represents coverage of that amino acid by the ImmunoSignature discriminating peptides.

The amino acid overlap score, s, is a corrected score of the representation of amino acids in the discriminating peptides that accounts for the composition of the library. For example, peptides on an array can exclude one or more of the 20 natural amino acids. Therefore, the overlap score accounts for the amino acid content in the library. To correct this score for library composition, an overlap score is calculated by the same method for a list of all array peptides. This allows for the calculation of an overlap score, s, at each amino acid via the equation $$s = a - (b/d)^* c$$

where a is the overlap score from the ImmunoSignature peptides, b is the number of ImmunoSignature peptides, c is the overlap score for the full array of peptide and d is the number of peptides on the full array.

Next, the amino acid overlap score obtained from the alignment of each of the discriminating peptides is converted to a protein score, S. To convert these scores at the amino acid level, s, to a full-protein statistic, S, the sum of scores for every possible tiling n-mer epitope within a protein is calculated, and the final score is the maximum along windows of, e.g., 20 mer.

Ranking of the identified candidate biomarkers is made relative to the ranking of randomly chosen non-discriminating peptides. Accordingly, an overlap score for non-discriminating peptides (non-discriminating 's' score) that align to each of one or more proteins of a same proteome or protein list is obtained as described for the discriminating peptides. The non-discriminating 's' score is then converted to a non-discriminating protein 'S' score for each of a plurality of randomly chosen non-discriminating peptides. For example, non-discriminating protein 'S' scores can be obtained for at least 25, at least 50, at least 100, or more randomly-chosen non-discriminating peptides.

The protein biomarkers identified are then ranked relative to the proteins identified by alignment of non-discriminating peptides.

In some embodiments, a method is provided for identifying a candidate target protein for the treatment of an autoimmune disease in a human subject, the method comprising: (a) identifying a set of discriminating peptides that differentiate the autoimmune disease from one or more different autoimmune diseases; (b) aligning the set of peptides to proteins in a human proteome; (c) identifying regions of homology between each peptide in the set to a region of an immunogenic protein; and (d) identifying the protein as a candidate target protein for treating said autoimmune disease. The method can further comprise identifying a set of discriminating peptides that differentiate the autoimmune disease from a healthy condition. Example 3 illustrates a method for identifying candidate target proteins using differentiating peptides that distinguish samples form healthy subjects from samples from subjects having SSc. A list of candidate protein targets is provided in Table 3. Similarly, candidate protein targets can be identified using differentiating peptides that distinguish samples from subjects having other autoimmune diseases from samples from healthy subjects, samples from subjects having other autoimmune diseases, and samples from subjects having mimic or other overlap diseases, which may or may not be autoimmune.

In some embodiments, a method for identifying a candidate protein biomarker for an autoimmune disease in a human subject, the method comprising: (a) identifying a set of discriminating peptides that differentiate said autoimmune disease from one or more different health conditions; (b) aligning the set of discriminating peptides to proteins in a proteome to obtain an alignment score for said set of discriminating peptides to one or more proteins of said proteome; ranking the identified proteins according to a statistical significance; and identifying the protein as a candidate protein biomarker for said autoimmune disease. In some embodiments, the method further comprises obtaining an overlap score, wherein the overlap score corrects for the peptide composition of the peptide library. In some embodiments, the discriminating peptides used in the method are identified as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$.

In some embodiments, the method further comprises identifying a set of discriminating peptides that differentiate the autoimmune disease from a healthy condition. In other embodiments, the method comprises identifying peptides that differentiate disease progression, In some embodiments, the differentiating peptides distinguish from subjects having SSc and organ involvement form subjects having SSc without organ involvement. Thus, the candidate biomarkers can serve to diagnose a disease, to identifying a stage of disease progression. The biomarkers can also be used in the monitoring of disease. Examples of candidate biomarkers identified for scleroderma are listed in Table 3. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

Alternatively, discriminating peptides identified according to the methods provided, can identify candidate target proteins using sequence motifs that are enriched in the most discriminating peptides that distinguish two different conditions. In one embodiment, the method for identifying a candidate target for the treatment of an autoimmune disease in a human subject comprises (a) obtaining a set of discriminating peptides that differentiate the autoimmune disease from one or more different autoimmune diseases; (b) identifying a set of motifs for said discriminating peptides; (c) aligning the set of motifs to a human proteome; (d) identifying regions of homology between each motif in the set to a region of an immunogenic protein; and (e) identifying the protein as a candidate target for treating said autoimmune disease. The method can further comprise identifying a set of discriminating peptides that differentiate the autoimmune disease from a healthy condition. Motifs that are enriched in the most discriminating peptides that can be used to identify candidate target proteins for development and use in treating various autoimmune diseases, some at different stages of progression are provided in FIGS. 5, 7, 9, 11, 13, 15, 17, 19, and 21.

In some embodiments, the step of identifying the autoimmune disease in the sample from a subject comprises (i) contacting a sample from the subject to an array of peptides comprising at least 10,000 different peptides synthesized in situ; (ii) detecting the binding of antibodies present in the sample to at least 25 peptides on said array to obtain a combination of binding signals; and (iii) comparing the combination of binding signals to a one or more groups of combinations of reference binding signals, wherein each of said groups of combinations of reference binding signals comprises a combination of binding signals obtained from a plurality of subjects having a different autoimmune disease. In some embodiments, the combination of binding signals from the subject is compared to a combination of binding signals obtained from one or more healthy reference subjects.

The discriminating peptides can also serve as a basis for the design of drugs that inhibit or activate the target protein-protein interactions. In another aspect, therapeutic and diagnostic uses for the novel discriminating peptides identified by the methods of the invention are provided. Aspects and embodiments thus include formulations, medicaments and pharmaceutical compositions comprising the peptides and derivatives thereof according to the invention. In some embodiments, a novel discriminating peptide or its derivative is provided for use in medicine. More specifically, for use in antagonising or agonising the function of a target ligand, such as a cell-surface receptor. The discriminating peptides of the invention may be used in the treatment of various diseases and conditions of the human or animal body, such as cancer, and degenerative diseases. Treatment may also include preventative as well as therapeutic treatments and alleviation of a disease or condition.

Accordingly, the methods, systems and array devices disclosed herein are capable of screening, identifying therapeutic targets, identifying vaccine targets, and/or treating a disease and/or condition at an early stage of the disease and/or condition. For example, the methods, systems and array devices disclosed herein are capable of detecting, diagnosing and monitoring a disease and/or condition days or weeks before traditional biomarker-based assays. Moreover, only one array, i.e., one immunosignature assay, is needed to detect, diagnose and monitor a wide spectra of diseases and conditions, including inflammatory conditions, autoimmune diseases, cancer and pathogenic infections.

Candidate therapeutic targets can be identified according to the method provided for any one of the autoimmune diseases recited elsewhere herein. In some embodiments, the candidate therapeutic targets can be identified for validation and subsequent treatment of SSc. Exemplary therapeutic candidates for the treatment of SSc are provided in Table 3.

Disease Scoring Systems

The differential binding activity or signatures, also referred to as "immunosignatures" (IS), obtained by the methods, devices and assays disclosed herein may also correlate with known disease scoring systems. For example the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients analyzed and diagnosed with an autoimmune disease or disorder when compared to a known immune-mediated disease scoring system, including clinical and laboratory scoring systems developed for SSc and DM. For example, binding signal data for discriminating peptides can be used to provide a score for the activity of an autoimmune disease. The score can correlate with an existing scoring system. For example, the score obtained for SSc according to the assay, method and devices provided can correlate with The Modified Rodnan Skin Score for scleroderma, the Medsger Severity Scale (Clin Exper Rheumatol 21:S42-S46 [2003]), and CT scoring systems (Assayag et al, [2012] High Resolution Computed Tomography Scoring Systems for Evaluating Interstitial Lung Disease in Systemic Sclerosis Patients. Rheumatology S1:003. doi:10.4172/2161-1149.S1-0030).

As disclosed herein, the AUC may be interpreted as the probability that a patient with active disease according to the known scoring system would have a higher value associated with the immunosignatures binding pattern than a patient with inactive or without disease according to the known scoring system.

Treatments and Conditions

The methods and arrays of the invention provide methods, assays and devices for the detection and diagnosis of an autoimmune disorder. Any one of the autoimmune disorders listed elsewhere herein can be detected and diagnosed. The methods and arrays of the embodiments disclosed herein can be used, for example, for screening of an immune disorder in a subject. A subject can be a human, a guinea pig, a dog, a cat, a horse, a mouse, a rabbit, and various other animals. A subject can be of any age, for example, a subject can be an infant, a toddler, a child, a pre-adolescent, an adolescent, an adult, or an elderly individual.

A condition of a subject can correspond to a disease or a healthy condition. In some embodiments, a condition of a subject is a healthy condition, and a method of the invention monitors the healthy condition. In some embodiments, a condition of a subject is a disease condition, and a method of the invention is used to diagnose/monitor a state and/or the progression of the condition. A method of the invention can also be used in the prevention of a condition. In some embodiments, a method of the invention is used in conjunction with a prophylactic treatment.

The arrays and methods of the invention can be used by a user. A plurality of users can use a method of the invention to identify and/or provide a treatment of a condition. A user can be, for example, a human who wishes to monitor one's own health. A user can be, for example, a health care provider. A health care provider can be, for example, a physician. In some embodiments, the user is a health care provider attending the subject. Non-limiting examples of physicians and health care providers that can be users of the invention can include, an anesthesiologist, a bariatric surgery specialist, a blood banking transfusion medicine specialist, a cardiac electrophysiologist, a cardiac surgeon, a cardiologist, a certified nursing assistant, a clinical cardiac electrophysiology specialist, a clinical neurophysiology specialist, a clinical nurse specialist, a colorectal surgeon, a critical care medicine specialist, a critical care surgery specialist, a dental hygienist, a dentist, a dermatologist, an emergency medical technician, an emergency medicine physician, a gastrointestinal surgeon, a hematologist, a hospice care and palliative medicine specialist, a homeopathic specialist, an infectious disease specialist, an internist, a maxillofacial surgeon, a medical assistant, a medical examiner, a medical geneticist, a medical oncologist, a midwife, a neonatal-perinatal specialist, a nephrologist, a neurologist, a neurosurgeon, a nuclear medicine specialist, a nurse, a nurse practitioner, an obstetrician, an oncologist, an oral surgeon, an orthodontist, an orthopedic specialist, a pain management specialist, a pathologist, a pediatrician, a perfusionist, a periodontist, a plastic surgeon, a podiatrist, a proctologist, a prosthetic specialist, a psychiatrist, a pulmonologist, a radiologist, a surgeon, a thoracic specialist, a transplant specialist, a vascular specialist, a vascular surgeon, and a veterinarian. A diagnosis identified with an array and a method of the invention can be incorporated into a subject's medical record.

Array Platform

In some embodiments, disclosed herein are methods and process that provide for array platforms that allow for increased diversity and fidelity of chemical library synthesis. The array platforms comprises a plurality of individual features on the surface of the array. Each feature typically comprises a plurality of individual molecules synthesized in situ on the surface of the array, wherein the molecules are identical within a feature, but the sequence or identity of the molecules differ between features. The array molecules include, but are not limited to nucleic acids (including DNA, RNA, nucleosides, nucleotides, structure analogs or combinations thereof), peptides, peptide-mimetics, and combinations thereof and the like, wherein the array molecules may comprise natural or non-natural monomers within the molecules. Such array molecules include the synthesis of large synthetic peptide arrays. In some embodiments, a molecule in an array is a mimotope, a molecule that mimics the structure of an epitope and is able to bind an epitope-elicited antibody. In some embodiments, a molecule in the array is a paratope or a paratope mimetic, comprising a site in the variable region of an antibody (or T cell receptor) that binds to an epitope an antigen. In some embodiments, an array of the invention is a peptide array comprising random, pseudo-random or maximally diverse peptide sequences.

The peptide arrays can include control sequences that match epitopes of well characterized monoclonal antibodies (mAbs). Binding patterns to control sequences and to library peptides can be measured to qualify the arrays and the immunosignaturing assay process. mAbs with known epitopes e.g. 4C1, p53Ab1, p53Ab8 and LnKB2, can be assayed at different doses. Additionally, inter wafer signal precision can be determined by testing sample replicates e.g. plasma samples, on arrays from different wafers and calculating the coefficients of variation (CV) for all library peptides. Precision of the measurements of binding signals can be determined as an aggregate of the inter-array, inter-slide, inter-wafer and inter-day variations made on arrays synthesized on wafers of the same batch (within wafer batches). Additionally, precision of measurements can be determined for arrays on wafers of different batches (between wafer batches). In some embodiments, measurements of binding signals can be made within and/or between wafer batches with a precision varying less than 5%, less than 10%, less than 15%, less than 20%, less than 25%, or less than 30%.

The technologies disclosed herein include a photolithographic array synthesis platform that merges semiconductor manufacturing processes and combinatorial chemical synthesis to produce array-based libraries on silicon wafers. By utilizing the tremendous advancements in photolithographic feature patterning, the array synthesis platform is highly-scalable and capable of producing combinatorial chemical libraries with 40 million features on an 8-inch wafer. Photolithographic array synthesis is performed using semiconductor wafer production equipment in a class 10,000 cleanroom to achieve high reproducibility. When the wafer is diced into standard microscope slide dimensions, each slide contains more than 3 million distinct chemical entities.

In some embodiments, arrays with chemical libraries produced by photolithographic technologies disclosed herein are used for immune-based diagnostic assays, for example called immunosignature assays. Using a patient's antibody repertoire from a drop of blood bound to the arrays, a fluorescence binding profile image of the bound array provides sufficient information to classify disease vs. healthy.

In some embodiments, immunosignature assays are being developed for clinical application to diagnose/monitor autoimmune diseases and to assess response to autoimmune treatments. Exemplary embodiments of immunosignature assays is described in detail in US Pre-Grant Publication No. 2012/0190574, entitled "Compound Arrays for Sample Profiling" and US Pre-Grant Publication No. 2014/0087963, entitled "Immunosignaturing: A Path to Early Diagnosis and Health Monitoring", both of which are incorporated by reference herein for such disclosure. The arrays developed herein incorporate analytical measurement capability within each synthesized array using orthogonal analytical methods including ellipsometry, mass spectrometry and fluorescence. These measurements enable longitudinal qualitative and quantitative assessment of array synthesis performance.

In some embodiments, detection of antibody binding on a peptide array poses some challenges that can be addressed by the technologies disclosed herein. Accordingly, in some embodiments, the arrays and methods disclosed herein utilize specific coatings and functional group densities on the surface of the array that can tune the desired properties necessary for performing immunosignature assays. For example, non-specific antibody binding on a peptide array may be minimized by coating the silicon surface with a moderately hydrophilic monolayer polyethylene glycol (PEG), polyvinyl alcohol, carboxymethyl dextran, and combinations thereof. In some embodiments, the hydrophilic monolayer is homogeneous. Second, synthesized peptides are linked to the silicon surface using a spacer that moves the peptide away from the surface so that the peptide is presented to the antibody in an unhindered orientation.

Detector Device

In some embodiments, the systems, platforms and methods disclosed herein include a detector device for detecting binding on the array formats disclosed herein, including antibody binding on the peptide arrays disclosed herein. In some embodiments, used in conjunction with optical detection methods (ccd, pmt, other optical detector, optical filters and other optical detection devices), detection of antibody binding is reported via optical detection in real-time or on a timed interval. In certain instances, quantification of final binding activity is reported via optical detection converted to AFU (arbitrary fluorescence units) or translated to electrical signal via impedance measurement or other electrochemical sensing. In other instances, antibody binding is detected by an emission or absorption of light or electromagnetic energy, either in the visible range or otherwise from an optically-detectable label on a probe applied to the peptide device. Optically detectable labels include, without limitation, fluorescent, chemiluminescent, electrochemiluminescent, luminescent, phosphorescent, fluorescence polarization, and charge labels. In some instances, a fluorescently labeled probe is active only in the presence of a specific target or antibody so that a fluorescent response from a sample signifies the presence of the target or antibody.

In some instances, light delivery schemes are utilized to provide the optical excitation and/or emission and/or detection of antibody binding. In certain embodiments, this includes using the flow cell materials (thermal polymers like acrylic (PMMA) cyclic olefin polymer (COP), cyclic olefin co-polymer, (COC), etc.) as optical wave guides to remove the need to use external components. In addition, in some instances light sources—light emitting diodes—LEDs, vertical-cavity surface-emitting lasers—VCSELs, and other lighting schemes are integrated directly inside the cartridge or detection device or built directly onto the peptide array surface to have internally controlled and powered light sources. PMTs, CCDs, or CMOS detectors can also be built into the detection device or cartridge.

Digital Processing Device

In some embodiments, the systems, platforms, software, networks, and methods described herein include a digital processing device, or use of the same. In further embodiments, the digital processing device includes one or more hardware central processing units (CPUs), i.e., processors that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In some embodiments, the systems, platforms, software, networks, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, a system is provided for making a differential diagnosis, the system comprising (a) an array of peptides comprising at least 10,000 different peptides synthesized in situ, wherein a sample from a subject is contacted to the array; (b) a detector for detecting the binding of antibodies present in said sample to at least 25 peptides on said array to obtain a combination of binding signals; and (c) a digital processing device for analyzing and comparing said combination of binding signals to one or more groups of combinations of reference binding signals, wherein each of said groups of combinations of reference binding signals comprises a combination of binding signals obtained from a plurality of subjects having a different disease, thereby making said differential diagnosis, wherein the method performance is characterized by an area under the receiver operator characteristic (ROC) curve (AUC) being greater than 0.6.

In other embodiments, a system is provided for determining disease progression in a subject known to have an autoimmune disease, said method comprising: (a) an array of peptides comprising at least 10,000 different peptides synthesized in situ; (b) a detector for detecting the binding of antibodies present in said sample to at least 25 peptides on said array to obtain a first combination of binding signals; and (c) a digital processing device for analyzing and comparing said first combination of binding signals to at least a second combination of reference binding signals, wherein said second combination of reference binding signals comprises a combination of binding signals obtained from a reference group comprising a plurality of subjects having a clinical manifestation indicative of progression of said autoimmune disease, thereby making said differential diagnosis, wherein the method performance is characterized by an area under the receiver operator characteristic (ROC) curve (AUC) being greater than 0.6.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Assay Methods

Broadly, the "Immunosignature" assay protocol follows the principles of ELISA. The peptide array slides were washed and hydrated in water. The slides were then blocked with BSA (3% w/v BSA in PBS-T) for 60 minutes at RT with gentle shaking. One hundred microliters of serum or plasma samples obtained from diseased and healthy volunteers were diluted in a PBST based buffer. Ninety microliters of each sample were then incubated on a peptide array for one hour at 37 C with an alternating shaking protocol. Following the sample (primary antibody) incubation the array was washed with a PBST wash buffer. Following the washing step, the array was incubated with 90 ul of secondary antibody (goat anti-human IgG-conjugated to Alexa-555, Life-Technologies). The secondary reagent was incubated for one hour at 37 C with an alternating shaking protocol. A secondary antibody-only control (negative control) was included on each slide along with normal serum control sample in triplicate to verify assay quality and reproducibility. After a one hour incubation, the array was washed again with a PBST wash buffer followed by water and isopropanol washes, then dried by centrifugation. The slide was then scanned on an Innopsys 910AL microarray scanner (InnoScan, Inc. Serial number 913p03). Fluorescent signal was measured by laser excitation at 532 nm and emission quantification at 547 nm.

Data acquisition was performed using the Innopsys Mapix software package (Innopsys Inc). The arrays ware analyzed for data outliers. After median normalization and $\log_{10}$-transformation, the median intensity of each feature across technical replicates was calculated and used for to classifier development work.

A Support Vector Machine (SVM) classifier was trained and cross-validated by assigning each sample to one of four cross-validated groups. Features that discriminate cases and controls in the training group were ranked by p-value. The top k features were used as input for the SVM model. Predictions for each group were made, and performance was calculated as Area Under the Curve (AUC) or sensitivity/specificity/accuracy using all the predictions from the four models vs. the true disease classes. The average performance was and confidence intervals (CI) were calculated. Diagnostic visualizations were generated, including "volcano" plots (i.e. p-value vs. log fold-change), ROC (receiver operating characteristic) curves, and model performance vs. number of input peptides.

Example 2—Diagnostic and Prognostic Assays for Scleroderma and Systemic Sclerosis Background: Scleroderma and Systemic Sclerosis (SSc) is a disease of the connective tissue featuring skin thickening that can involve scarring, blood vessel problems, and varying degrees of inflammation not only of skin but also internal organs. Diagnosis of SSc is difficult due to the complexity of manifestations and overlap with other autoimmune diseases. It typically requires a combination of medical history review, physical examination, lab tests and X-Rays. No single biomarker is available but serologic testing has identified ANA and anticentromere antibodies (ACA) in 60%-80% of patients, and ScL 70 antibodies in 30%. However, these antibodies can also be found in some healthy individuals or patients with other autoimmune diseases e.g. dermatomyositis (DM). In addition to a better diagnostic, there is need for a better prognostic test. Raynaud's syndrome is the first manifestation of SSc in about 75% of patients, but does not serve as a prognostic. Patients with diffuse rather than limited skin involvement tend to develop more serious conditions such as ILD, PAH, GAVE, and renal complications. However, this observation is also not reliable enough to be prognostic.

Methods: A study population of 719 plasma samples was evaluated; it was comprised of SSC (n=301), DM (205), a group of other autoimmune diseases (95) including MCTD, UCTD, lupus, myositis & polymyositis, morphea, and healthy samples (118). A panel of 84 control samples were used to facilitate assay qualifications.

All patients met ACR classification criteria at diagnosis. An IS assay was used to detect plasma antibodies bound to a microarray of ~126,000 unique peptides. Peptide sequences were designed (using 16 of the 20 amino acids) to broadly sample combinatorial space thus providing a library of diverse epitope mimetics for antibodies to selectively and competitively bind. Features most discriminating SSc contrasts were identified using a t-test. Support vector machines (SVM) classifiers were trained and assessed by 100 iterations of 5-fold cross validation analysis. Models ranging from 25 to 10,000 peptide inputs were evaluated.

Results: A classifier trained on 10,000 differentially bound peptides distinguished SSc patients from healthy donors with strong performance characteristics. Other algorithms with similar model sizes were built that differentiated SSc from other autoimmune diseases such as DM. Finally, SSc patients that ever progressed to one of several more severe conditions: ILD, renal crisis, and GAVE, could be distinguished from those SSc patients who never did. These cross-validated estimates of classification performance are provided in Table 1.

Figure 4:
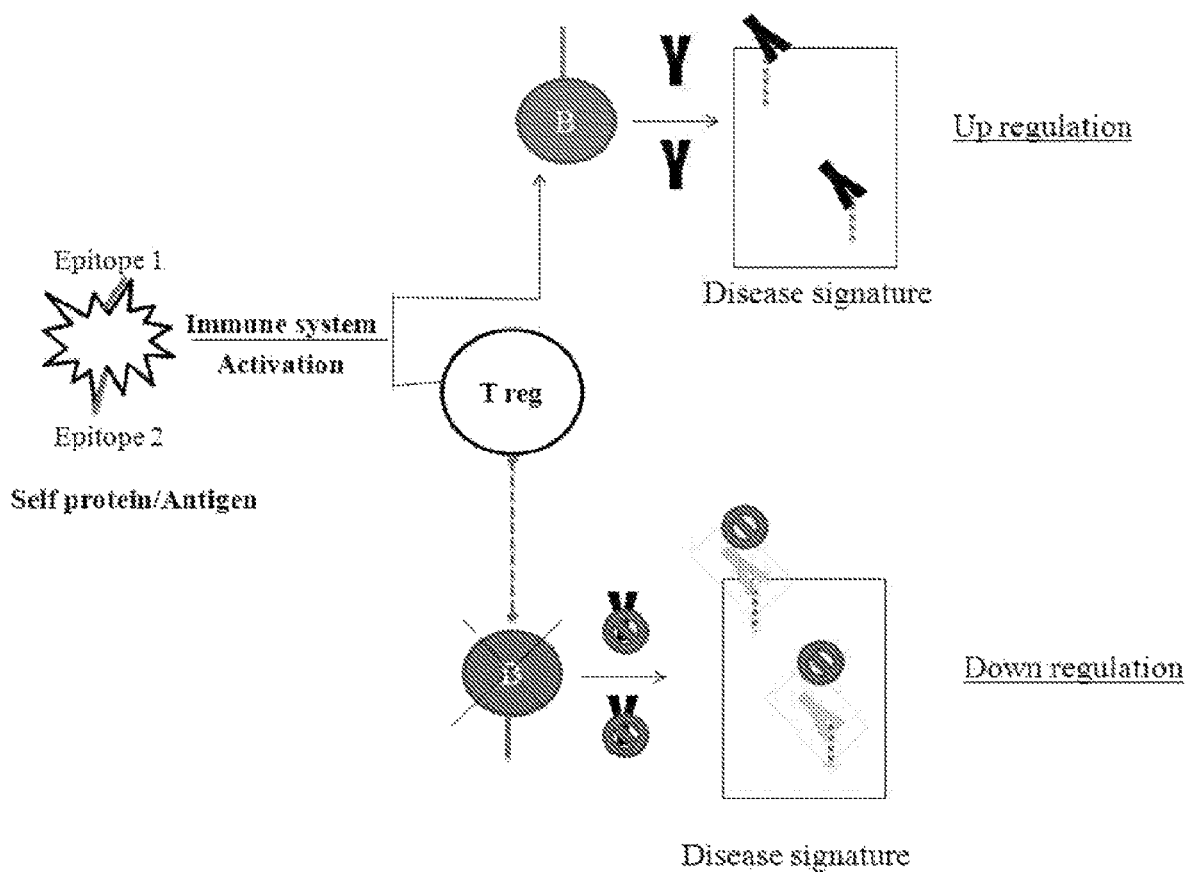
FIG. 4. is a pathway showing how a self protein/antigen can lead to up-regulation and down-regulation of an immunosignature in peptide microarrays.
Figure 6A:
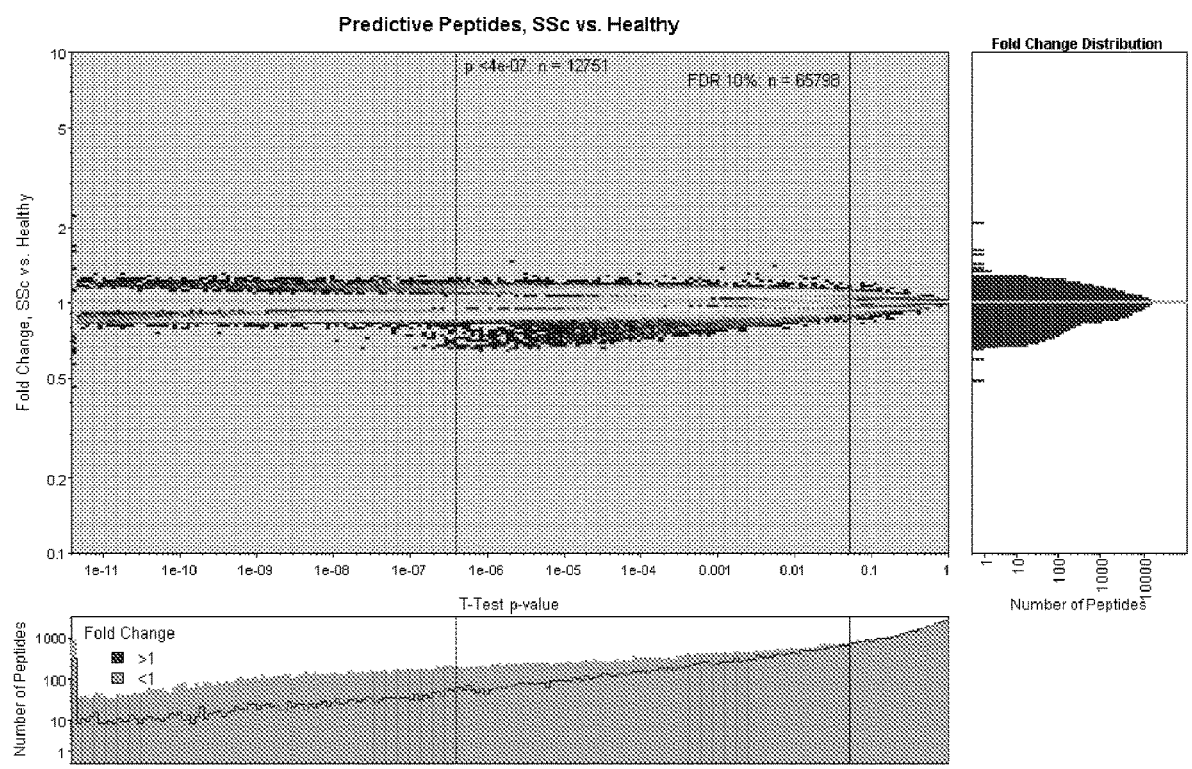
FIG. 6A is Volcano Plot depicting the differentiation of subjects with Scleroderma (SSc) from healthy controls by peptide binding intensities. The ratio of mean intensity among samples from patients with Scleroderma to mean intensity in control patients is plotted vs. the p-value for the difference in means from a t-test.
Figure 6B:
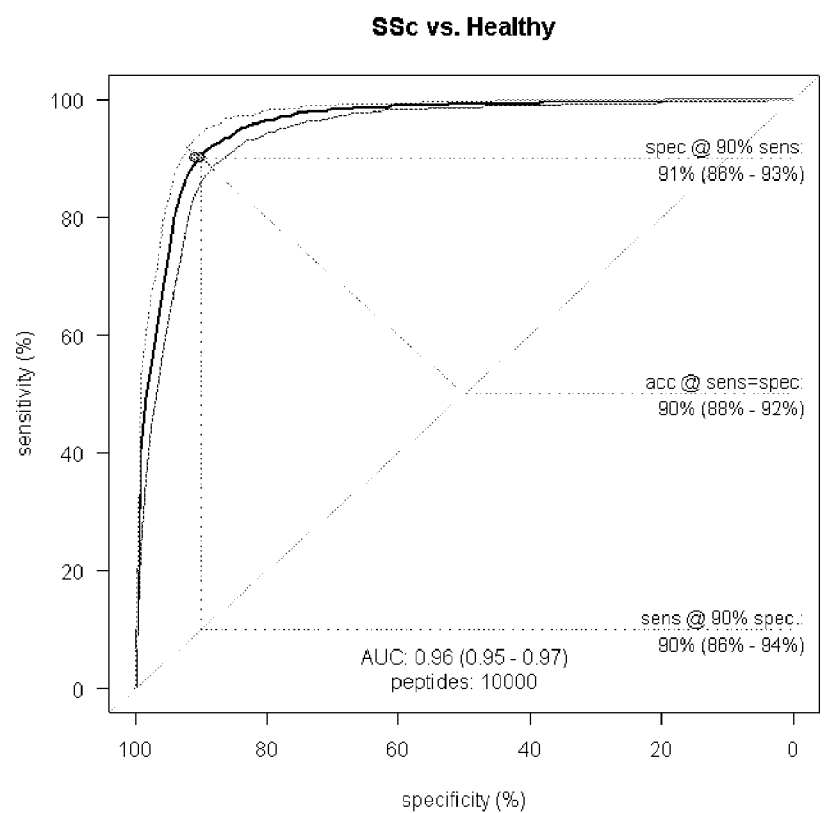
FIG. 6B are ROC curves for an ImmunoSignature model of Scleroderma for identifying patients with Scleroderma from healthy controls. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.
Figure 6C:
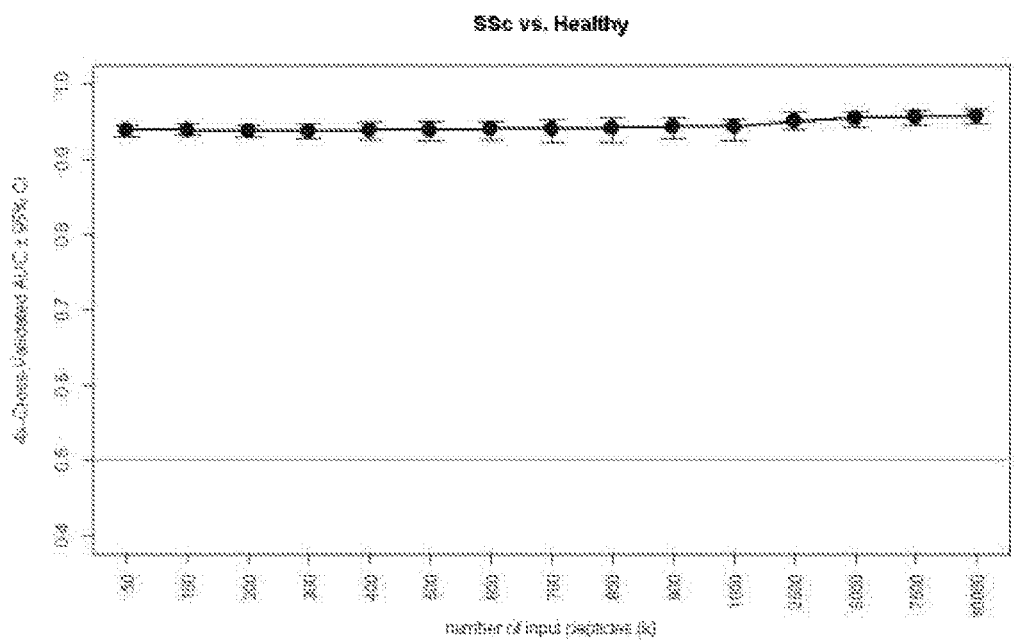
FIG. 6C are ROC estimates as a function of input size—Five fold cross validated area under the ROC curve (+/−95% CI) are provided for models of different input peptide sizes. Peptides were selected based on a t-test and the top k features were used in a support vector machine to build a classifier of Scleroderma vs. healthy controls. Feature selection and model construction were performed within the cross-validation loop to prevent bias.

FIG. 5 is a table depicting the top differentiating peptides in an immunosignature when comparing patients with SSc and healthy subjects. FIG. 5A depicts the top sub-motifs. FIG. 5B depicts the enriched peptides in the top 1000 differentiating peptides. FIG. 6 is a graphical representation of the results in FIG. 5. The headings apply to the list of motifs in (A) and to the amino acids list in (B) of this and all tables of differentiating peptides provided herein, where "n" is the number of times the motif appeared in the sequences of the top discriminating peptides; "n. lib" is the number of times the motif appeared in the library; "enrich" is the enrichment factor of the motif in the discriminating peptides relative to all of the motifs found in all sequences in the library; "padj. holm" is the p-adjusted value to control for multiple testing errors.

Figure 8A:
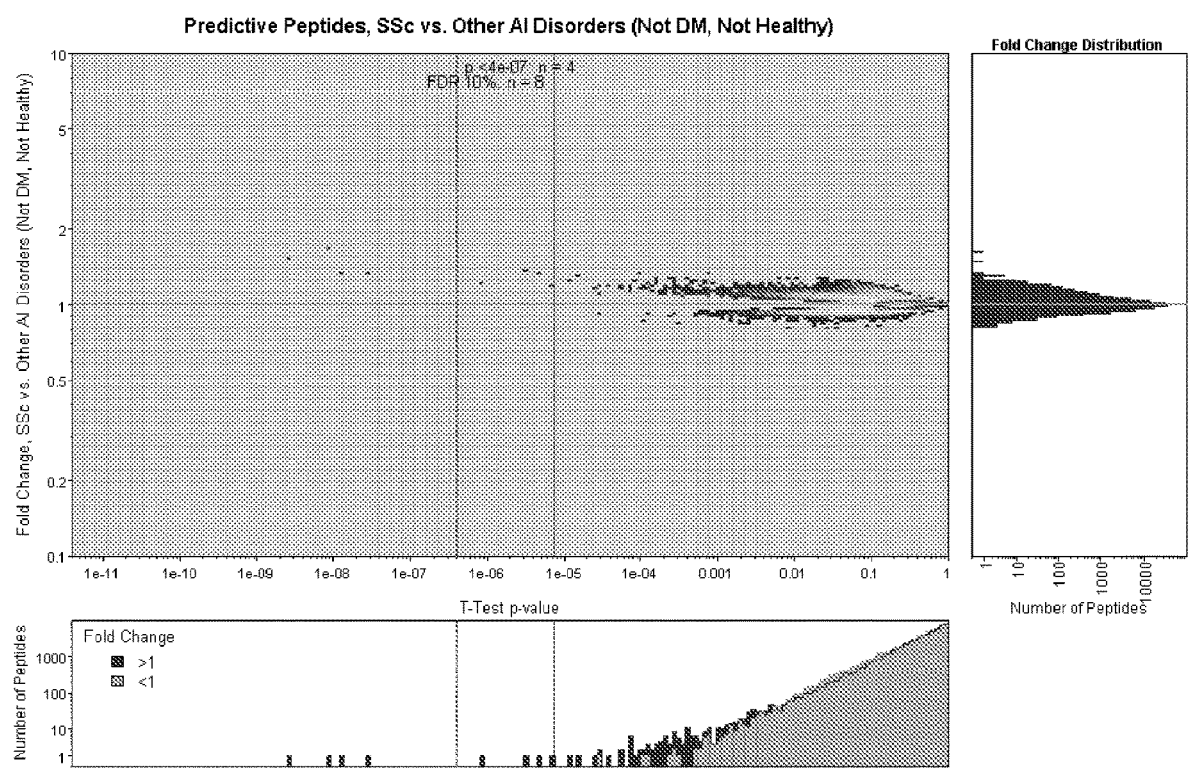
FIG. 8A is a Volcano Plot depicting the differentiation of subjects with Scleroderma (SSc) from other autoimmune mimic diseases ("Other AI") by peptide binding intensities. The ratio of mean intensity among samples from patients with Scleroderma to mean intensity in patients with other autoimmune disorders is plotted vs. the p-value for the difference in means from a t-test.
Figure 8B:
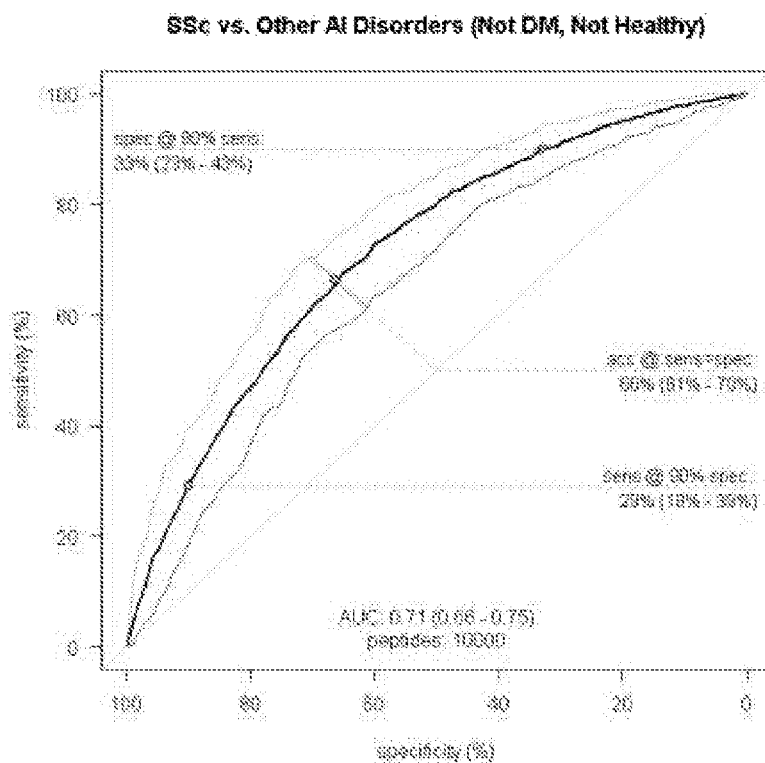
FIG. 8B are ROC curves for an ImmunoSignature model of Scleroderma for identifying patients with Scleroderma from other autoimmune diseases. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.
Figure 8C:
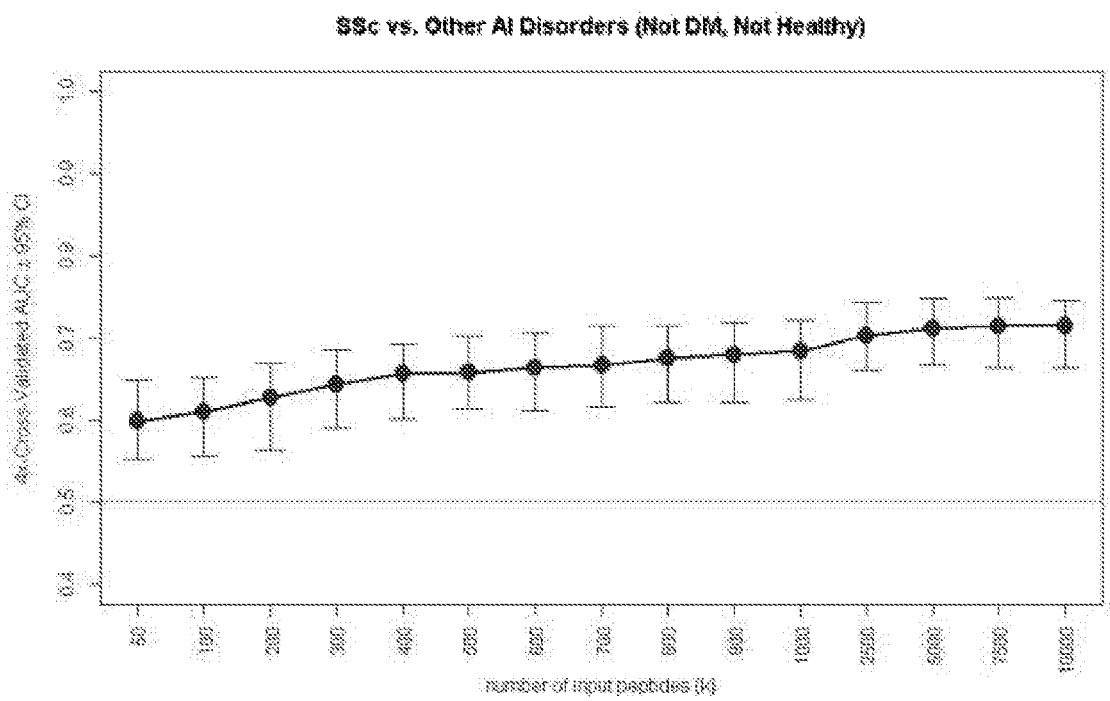
FIG. 8C are ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma vs. other autoimmune disorders. Feature selection and model construction were performed within the cross-validation loop to prevent bias.

FIG. 7 is a table depicting the top differentiating peptides in an immunosignature when comparing patients diagnosed with SSc and other autoimmune disorders. "Other autoimmune disorders" include Atypical myositis, acne rosacea, anti-PL7 with ILD and myositis, atypical myositis, Behcet's, Crohn's with atypical, rash, cutaneous lupus, Discoid lupus, DM, DM rash but negative antibodies, DM versus lupus, DM vs UCTD, drug eruption, eosinophilic fasciitis, Graft Versus Host Disease (GVHD), Hodgkins disease, lichen planus, lSSc, lupus panniculitis, Mixed Connective Tissue Disease (MCTD), Morphea, myositis possibly drug induced, myositis with Jo-1 antibodies, nephrogenic systemic fibrosis, polymyalgia rheumatic, Polymyositis, possible DM-awaiting serotyping, possible drug eruption, Psoriasis, pulmonary fibrosis, pulmonary fibrosis with anti-J01, Raynauds only, Rhabdomyolysis, Sle, SLE/mixed, SSc, SSc/DM overlap, SSc/SLE, Undifferentiated Connective Tissue Disease (UCTD), UCTD with rash, Unknown, unknown with features of urticarial, and weakness no diagnosis. FIG. 7A depicts the top sub-motifs. FIG. 7B depicts the enriched peptides in the top 1000 differentiating peptides. FIG. 8 is a graphical representation of the results seen in FIG. 7.

FIG. 9 is a table depicting the top differentiating peptides in an immunosignature when comparing patients diagnosed with SSc and patients in a renal crisis. FIG. 9A depicts the top sub-motifs. FIG. 9B depicts the enriched peptides in the top 1000 differentiating peptides. FIG. 10 is a graphical representation of the results seen in FIG. 9.

FIG. 11 is a table depicting the top differentiating peptides in an immunosignature when comparing patients diagnosed with SSc and gastric antral vascular ectasia (GAVE). FIG. 11A depicts the top sub-motifs. FIG. 11B depicts the enriched peptides in the top 1000 differentiating peptides. FIG. 12 is a graphical representation of the results seen in FIG. 11.

FIG. 13 is a table depicting the top differentiating peptides in an immunosignature when comparing patients diagnosed with SSc and DM. FIG. 13A depicts the top sub-motifs. FIG. 13B depicts the enriched peptides in the top 1000 differentiating peptides. FIG. 14 is a graphical representation of the results seen in FIG. 13.

FIG. 15 is a table depicting the top differentiating peptides in an immunosignature when comparing patients diagnosed with SSc with interstitial lung disease (ILD+) and SSc without interstitial lung disease (ILD−). FIG. 15A depicts the top sub-motifs. FIG. 15B depicts the enriched peptides in the top 1000 differentiating peptides. FIG. 16 is a graphical representation of the results seen in FIG. 15.

Conclusions: Reproducible binding patterns produced by peripheral-blood antibody repertoires on a mimetic-peptide microarray can differentiate SSc from healthy donors and from other autoimmune diseases. In addition, distinctive immunosignatures were established for SSc patients that ever progressed to more serious disease manifestations. This suggests that the IS technology might be instrumental in the development of both new diagnostic and prognostic tests for SSc.

TABLE 1

Classification Performance Estimates of IS for SSc Diagnosis and Prognosis

| Contrast | AUC | Sens. @ 90% Spec. | Spec. @ 90% Sens. | Accuracy @ Sens. = Spec. |
| --- | --- | --- | --- | --- |
| SSc vs Healthy | 0.96(0.95-0.97) | 90%(86-94%) | 91%(86-93%) | 90%(88-92%) |
| SSc vs Other AI | 0.71(0.66-0.75) | 29%(18%-39%) | 33%(23%-43%) | 66%(61%-70%) |
| SSc vs DM | 0.77(0.74-0.8) | 40%(33-48%) | 41%(33-48%) | 70%(67-73%) |
| SSc ILD+ vs ILD− | 0.68(0.64-0.72) | 23%(13-33%) | 31%(21-41%) | 63%(59-68%) |
| SSc Renal Crisis+ vs Crisis− | 0.72(0.6-0.82) | 27%(3-53%) | 42%(12-62%) | 65%(55-76%) |
| SSc GAVE+ vs GAVE− | 0.77(0.64-0.84) | 28%(8-46%) | 49%(10-67%) | 69%(62-77%) |

Example 3: Distinguishing Dermatomyositis and Systemic Sclerosis from Patients with Interstitial Lung Disease Background: Dermatomyositis (DM) is an inflammatory autoimmune disease with heterogeneous manifestations affecting skin, muscles, and lungs. The complexities of presentation make clinical diagnosis and prognosis challenging. Histologic findings also vary, confounding their utility. Several DM-specific antigens have been identified suggesting serologic diagnosis may be possible. However, alternative antigens would be required since many DM patients do not possess antibodies to these antigens. Interstitial lung disease (ILD) develops in 20-40% of patients, displaying a spectrum from mild to rapidly progressive, and possibly fatal, lung disease. Some DM-serotypes are at higher risk than others for ILD progression, but serotyping alone is not sufficiently sensitive or specific to guide clinical care.

A simple test to differentiate DM from other inflammatory autoimmune disease and to predict those that will progress to ILD would improve patient care. In addition, a discovery method for new DM-antigens would facilitate diagnostic and therapeutic efforts. The immunosignature (IS) platform was investigated to determine if it could address both clinical and discovery goals.

Methods: A study population of 719 plasma samples was evaluated; it was comprised of SSC (n=301), DM (205), a group of other autoimmune diseases (95) including MCTD, UCTD, lupus, myositis & polymyositis, morphea, and healthy samples (118). A panel of 84 control samples were used to facilitate assay qualifications. All patients met ACR classification criteria at diagnosis. An IS assay was used to detect plasma antibodies bound to a microarray of ~126,000 unique peptides. Peptide sequences were designed to broadly sample combinatorial space thus providing a library of diverse epitope mimetics for antibodies to selectively bind. Features most discriminating DM contrasts were identified using a t-test. Classification efficacy was determined in a support vector machine using 100 iterations of 5-fold cross validation.

Results: Cross-validated estimates of classification performance are provided in Table 2. Algorithms trained on differentially bound peptides distinguished DM from healthy donors and other AI, such as SSc. Both DM and SSc patients that ever progressed to ILD could be distinguished from those that never did. Up to 10,000 peptides whose antibody-binding characteristics differentiated disease groups were identified and used as inputs to these classifiers. Notably, the models for DM:ILD+/− and for SSc:ILD+/− were similarly predictive; however, the significantly distinguishing peptides used in these 2 classifiers showed no overlap.

TABLE 2

Classification performance estimates of IS for DM contrasts

| Contrast | AUC | Sens. @ 90% Spec. | Spec. @ 90% Sens. | Accuracy @ Sens. = Spec. |
|---|---|---|---|---|
| DM vs Healthy | 0.94 (0.93-0.96) | 83% (75-88%) | 85% (79-89%) | 87% (85-89%) |
| DM vs Other AI | 0.66 (0.61-0.70) | 17% (9%-25%) | 31% (23%-39%) | 62% (58%-66%) |
| DM vs SSc | 0.77 (0.74-0.8) | 40% (33-48%) | 41% (33-48%) | 70% (67-73%) |
| DM: ILD+ vs ILD− | 0.69 (0.63-0.72) | 22% (12-33%) | 30% (16-45%) | 65% (60-70%) |
| SSc: ILD+ vs ILD− | 0.68 (0.64-0.72) | 23% (13-33%) | 31% (21-41%) | 63% (59-68%) |

FIG. 17 is a table depicting the top differentiating peptides in an immunosignature when comparing patients diagnosed with DM and healthy subjects. FIG. 17A depicts the top sub-motifs. FIG. 17B depicts the enriched peptides in the top 1000 differentiating peptides. FIG. 18 is a graphical representation of FIG. 17.

FIG. 19 is a table depicting the top differentiating peptides in an immunosignature when comparing patients diagnosed with DM and other autoimmune disorders. "Other autoimmune disorders" include Atypical myositis, acne rosacea, anti-PL7 with ILD and myositis, atypical myositis, Behcet's, Crohn's with atypical, rash, cutaneous lupus, Discoid lupus, DM, DM rash but negative antibodies, DM versus lupus, DM vs UCTD, drug eruption, eosinophilic fasciitis, Graft Versus Host Disease (GVHD), Hodgkins disease, lichen planus, lSSc, lupus panniculitis, Mixed Connective Tissue Disease (MCTD), Morphea, myositis possibly drug induced, myositis with Jo-1 antibodies, nephrogenic systemic fibrosis, polymyalgia rheumatic, Polymyositis, possible DM-awaiting serotyping, possible drug eruption, Psoriasis, pulmonary fibrosis, pulmonary fibrosis with anti-J01, Raynauds only, Rhabdomyolysis, Sle, SLE/mixed, SSc, SSc/DM overlap, SSc/SLE, Undifferentiated Connective Tissue Disease (UCTD), UCTD with rash, Unknown, unknown with features of urticarial, and weakness no diagnosis. FIG. 19A depicts the top sub-motifs. FIG. 19B depicts the enriched peptides in the top 1000 differentiating peptides. FIG. 20 is a graphical representation of FIG. 19.

FIG. 21 is a table depicting the top differentiating peptides in an immunosignature when comparing patients diagnosed with DM and Interstitial lung disease (ILD+) and DM without interstitial lung disease (ILD−). FIG. 21A depicts the top sub-motifs. FIG. 21B depicts the enriched peptides in the top 1000 differentiating peptides. FIG. 22 is a graphical representation of FIG. 21.

Mimotope binding patterns identified DM patients from non-DM patients. Deciphering the antigens that these peptides mimic may reveal new DM-specific antigens. Classifiers for DM versus other AI, and for patients that progressed to ILD were also evaluated. The lack of any overlap between the ILD predicting peptides for DM vs. SSc patients supports a conclusion that these are unique diseases, despite common clinical manifestations and treatment regimens.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 4—Identification of Immunogenic Autoantigen Targets

Discriminating peptides that differentiate healthy subjects from subjects with SSc were analyzed relative to the human proteome to indicate the originally immunogenic autoantigen targets. The discriminating peptides were chosen for having a p-value of less than p<2.53E-06.

Proteome alignment: Array peptides were aligned to proteins in human proteome RefSeq release 84, corresponding to human genome build GrCh38 (https://www.ncbi.nlm.nih.gov/refseq/), compiled Mar. 10, 2016, using the longest transcript variant for each unique gene ID. The alignment algorithm uses a modified BLAST strategy (Altschul, S. F. & Gish, W. (1996) "Local alignment statistics." Meth. Enzymol. 266:460-480), requiring a seed of 3 amino acids with a gap penalty of 4, with a scoring matrix of BLOSUM62 (Henikoff, J. G. Amino acid substitution matrices from protein blocks. Proc. Natl. Acad. Sci. USA 89:10915-10919 [1992]) modified to reflect the amino composition of the array (States, D. J., Gish, W., Altschul, S. F. (1991) "Improved sensitivity of nucleic acid database searches using application-specific scoring matrices." Methods 3:66-70). These modifications increase the score of degenerate substitutions, remove penalties for amino acids absent from the array and score all exact matches equally.

To generate a p-value for alignment of a set of ImmunoSignature peptides to a protein, all peptides that yield a positive BLAST score to the protein were assembled into a matrix, with each row of the matrix corresponding to an aligned peptide and each column corresponding to one of the consecutive amino acids that comprise this protein, with gaps and deletions allowed within the peptide rows to allow for alignment to the protein. Each position within the matrix is the score, from the same scoring matrix as for the proteome alignments, of the paired peptide and protein amino acid in that position. Then, for each amino acid in the protein, the corresponding column is summed to create an "overlap score" that represents coverage of that amino acid by the ImmunoSignature peptides. To correct this score for library composition, an overlap score is calculated using an identical method for a list of all array peptides. Finally, a Fischer Exact Test is used to calculate a p-value for the ImmunoSignaure overlap score versus the full library overlap score. To convert these p-values at the amino acid level to a full-protein statistic, the sum of the negative log of the p-value for every possible 20-mer epitope within a protein is calculated, and the final score is the maximum along this rolling window of 20 for each protein.

Table 3 provides a list of the top scoring target proteins that were identified according to the method. One hundred and sixty nine candidate biomarkers were identified. The discriminating peptides were chosen for having a p-value of less than p<2.53E-06 by Welch's t-test.

FIG. 24 shows an exemplary autoantigen, CCL22, that was determined as a candidate protein biomarker that was identified by the discriminating peptides comparing subjects having SSc with organ involvement (GAVE +) with subjects having SSc without organ involvement (GAVE −).

These data show that discriminating peptides that distinguish different disease states can be used to identify candidate antigen or autoantigen target that can be investigated for use in developing therapeutics. Additionally, the presence of specific antigen or autoantigen targets can be used to determine the severity of a disease, and potentially predict disease progression.

Example 5—Precision of Measurements of Binding Signals

The binding precision of 200 array features (different peptides) used to distinguish subjects that tested sera-positive for Chagas disease from sera-negative subjects was

TABLE 3

Candidate target proteins identified from alignments of discriminating peptides that distinguish samples from subjects having SSc from samples from healthy subjects

| | | | | | | | | |
|---|---|---|---|---|---|---|---|---|
| PF4 | GNGT1 | MAP1LC3A | GAGE12J | RGCC | IGLV2-11 | DYNLT1 | UCN3 | BGLAP |
| CAMK2N2 | SMAGP | SMIM2 | PRAC1 | ARPC5 | RPL22 | SERF1A | LEAP2 | ANAPC15 |
| GHRL | RIPPLY2 | ATPIF1 | BAD | SPANXN3 | PKIB | SERF1B | RPLP2 | GPIHBP1 |
| C1orf210 | ACBD7 | STATH | PPP1R11 | UQCRHL | UCMA | TMEM233 | SREK1IP1 | EVA1B |
| PF4V1 | SMIM17 | CLEC2B | TRBV10-3 | PAIP2B | POLR2D | VPREB1 | TIMM13 | OTOR |
| RPL22L1 | C4orf32 | MT1F | SPANXN2 | DEFA5 | APLN | IGLV1-40 | SAP30L | GABARAPL2 |
| IGLV1-50 | GAGE2E | IGLV5-37 | PYY | JCHAIN | FAM9C | PPP1R14B | IGLV2-14 | TAF13 |
| C9orf16 | IGKV2-40 | GAGE12C | C7orf49 | IGLV2-23 | PPP1R1B | PTMA | FAM174B | NHLH1 |
| LYRM9 | IGLV5-45 | GAGE12E | PLGLB2 | DEFA4 | MAP1LC3C | GAGE10 | RIPPLY1 | HINT1 |
| CDC26 | IGKV2D-40 | GAGE12D | PLGLB1 | GAGE12H | IGLV9-49 | PCP4L1 | COA4 | |
| TUSC2 | IGLV1-36 | FXYD2 | UBE2V1 | PAIP2 | SCX | ERICH4 | IGFL4 | |
| MAP1LC3B | RPLP1 | SDHAF4 | VAMP8 | IGLV3-32 | SCGB2A1 | FDCSP | BORCS7 | |
| NPFF | DPH3 | HOPX | RPRM | UBL5 | PKIA | LINC00116 | SMIM7 | |
| SMIM13 | CTNNBIP1 | PRCD | GAGE13 | RD3L | PKIG | S100G | ISCA1 | |
| IGLV1-44 | GNG11 | OTOS | NUPR1 | PIGY | ERICH2 | SMIM19 | EIF1AD | |
| MAP1LC3B2 | POLR2L | C2orf76 | LINC00493 | APOC1 | DEFB131 | FAM101B | THRSP | |
| HIGD1C | IGLV3-22 | HMGA1 | PIGBOS1 | PPP1R1A | TRBV10-1 | CNPY1 | IGKV5-2 | |
| SNN | C14orf142 | C1orf54 | PRAC2 | CENPM | LCE6A | SUMO4 | TGIF2-C20orf24 | |
| DEXI | GAGE12G | LST1 | RNF7 | PRLH | CEND1 | HMGN1 | UBE2V2 | |
| EVA1A | GAGE12F | DEFB114 | SMIM1 | C12orf57 | LAMTOR1 | PCP4 | BIK | |

RNA Pol II subunit L is an example of the immunogenic autoantigens identified by the method by differentiating peptides that distinguish healthy subjects from subjects having SSc (FIGS. 23A and B).

FIG. 23A shows the peptide overlap difference scores, s, calculated for the alignments of IMS peptide-motifs plotted alongside the RNA Pol II subunit L aa positions. Peptides from the SSc vs. healthy contrast showed significant alignment with RNA pol II subunit L, ranking it 35 out of 20,378 of the human proteins in the proteome. The ball and stick model to the right shows the structure of RNA pol II subunit L. The region displayed in balls corresponds to the aa positions marked with a red box within the graph. The highest scoring aa is aspartic acid, D, in the center of the RNA pol cluster; it is shown in the ball structure as orange. We note that a threonine (T) near the center of the cluster scored poorly; there is no T in the IMS array sequences. FIG. 23 B shows a histogram displaying the distribution of protein epitope scores, S, for each protein in the human proteome vs the SSc vs healthy classifying peptides. POLR2L's score is 583.

RNA pol II, is a known autoantigen that has been characterized in patients with scleroderma.

estimated using a set of 8 serum samples. Four Chagas positive samples and 3 Chagas negative samples were selected from the full cohort of donors and assayed in triplicate on each slide from multiple wafers in two study designs. One in-house normal donor sample was also assayed in duplicate on each slide.

Within wafer lot: Three wafers from a single production lot were selected and qualified using a one-slide QC sample set. The remaining 12 slides from each wafer were evaluated using the precision study sample set. The slides were run across 3 cassettes per day over 3 days. Slides from each wafer were distributed evenly across the 3 days such that each cassette contained 2 slides from one of the three wafers and 1 slide each from the remaining two wafers.

Between wafer lot: One wafer from each of 4 production lots was selected and qualified using a one-slide QC sample set. The remaining 12 slides from each wafer were evaluated using the precision study sample set. The slides were run across 4 cassettes per day over 3 days. Slides from each wafer were distributed evenly across the 3 days such that each cassette contained 2 slides from two of the four wafers.

Data analysis: A mixed effect model was used to estimate the sources of experimental variance. Donor was treated as a fixed effect. Nested factors 'Wafer', 'slide', and 'array' were crossed with 'day', and were treated as random effects. Models were fit in r using the lme4 package.

TABLE 4

| Precision of signal binding measurements | | |
|---|---|---|
| | CV | % Contribution |
| Within wafer-batches | | |
| Inter-array | 11.21 | 59.6 |
| Inter-slide | 4.3 | 8.9 |
| Inter-wafer | 2.7 | 3.5 |
| Inter-day | 7.7 | 28.0 |
| TOTAL | 14.6 | 100 |

TABLE 4-continued

| Precision of signal binding measurements | | |
|---|---|---|
| | CV | % Contribution |
| Between wafer-batches | | |
| Inter-array | 14.3 | 38.7 |
| Inter-slide | 7.6 | 11.0 |
| Inter-wafer | 14.6 | 40.6 |
| Inter-day | 7.1 | 9.7 |
| TOTAL | 22.9 | 100 |

The data show that measurements of binding signals made on arrays within wafer batches can be made with precision varying less than 15%; and that measurements of binding signals made on arrays between wafer batches can be made with precision varying less than 25%".

What is claimed is:

1. A method of making a differential diagnosis of an autoimmune disease, said method comprising:
   (a) synthesizing in situ at least 10,000 different peptides on an array of peptides, wherein said at least 10,000 different peptides comprise at least 25 differentiating peptides comprising one or more motifs having a sequence selected from the group consisting of SEQ ID NO: 10, 20, 56-66, and 99;
   (b) contacting a sample from a subject to said array;
   (c) detecting binding of said sample to the at least 25 differentiating peptides on said array to generate a binding pattern;
   (d) comparing said binding pattern to one or more reference binding patterns, wherein the one or more reference binding patterns are obtained from a plurality of reference subjects known to have a plurality of autoimmune diseases; and
   (e) making the differential diagnosis of said subject for the autoimmune disease from the plurality of autoimmune diseases of the plurality of reference subjects.

2. The method of claim 1, wherein the one or more reference binding patterns is obtained by detecting the binding of a sample from each of said plurality of subjects in said reference group to said at least 25 differentiating peptides on an array of peptides comprising at least 10,000 different peptides synthesized in situ.

3. The method of claim 2, wherein the difference between the binding pattern and the one or more reference binding patterns to said at least 25 differentiating peptides determines said differential diagnosis.

4. The method of claim 1, wherein said plurality of autoimmune diseases comprises another autoimmune disease different from said autoimmune disease of said subject.

5. The method of claim 4, wherein said autoimmune disease is dermatomyositis (DM), and said different autoimmune disease is scleroderma.

6. The method of claim 5, wherein said at least 25 differentiating peptides are further enriched by at least 100% of one or more amino acids selected from the group consisting of serine, glycine, tyrosine, arginine, alanine, glutamine and valine in the one or more motifs when compared to the at least 10,000 peptides in said array.

7. The method of claim 1, further comprising comparing the binding pattern from said subject to a reference binding pattern obtained from healthy subjects.

8. The method of claim 7, wherein said autoimmune disease is scleroderma, and said at least 25 differentiating peptides are further enriched by at least 100% of one or more amino acids selected from the group consisting of tyrosine, lysine, arginine, phenylalanine, serine, tryptophan, glycine, and alanine.

9. The method of claim 7, wherein said autoimmune disease is scleroderma, and said at least 25 differentiating peptides further comprise one or more of the motifs having a sequence selected from the group consisting of SEQ ID NO: 1-8 when compared to the at least 10,000 peptides in said array.

10. The method of claim 7, wherein said autoimmune disease is dermatomyositis (DM), and said at least 25 differentiating peptides are further enriched by at least 100% of one or more amino acids selected from the group consisting of tyrosine, tryptophan, serine, glycine, aspartic acid, and phenylalanine.

11. The method of claim 7, wherein said autoimmune disease is dermatomyositis (DM), and said at least 25 differentiating peptides further comprise one or more of the motifs having a sequence selected from the group consisting of SEQ ID NO: 2-4, and 78-84 when compared to the at least 10,000 peptides in said array.

12. The method of claim 1, wherein said autoimmune disease is scleroderma, and wherein said reference binding pattern comprises a binding pattern obtained from the plurality of reference subjects known to have the plurality of autoimmune diseases comprising Mixed Connective Tissue Disease (MCTD), Undifferentiated Connective Tissue Disease (UCTD), myositis, polymyositis, systemic lupus erythomatosus, and morphea.

13. The method of claim 12, wherein said autoimmune disease is scleroderma, and said at least 25 differentiating peptides are further enriched by at least 100% of one or more amino acids selected from the group consisting of aspartic acid, glutamic acid, proline, valine, glycine, and serine.

14. The method of claim 12, wherein said autoimmune disease is scleroderma, and said at least 25 differentiating peptides further comprise one or more of the motifs having a sequence selected from the group consisting of SEQ ID NO: 9-24 when compared to the at least 10,000 peptides in said array.

15. The method of claim 1, wherein said autoimmune disease is dermatomyositis (DM), and wherein said reference binding pattern comprises a binding pattern obtained from the plurality of reference subjects known to have the plurality of autoimmune diseases comprising MCTD, UCTD, myositis, polymyositis, systemic lupus erythomatosus, and morphea.

16. The method of claim 15, wherein said autoimmune disease is DM, and said at least 25 differentiating peptides are further enriched by at least 100% of one or more amino acids selected from the group consisting of lysine, histidine, serine, arginine, glutamic acid, alanine, and glycine.

17. The method of claim 15, wherein said autoimmune disease is DM, and said at least 25 differentiating peptides further comprise one or more of the motifs having a sequence selected from the group consisting of SEQ ID NO: 85-90 when compared to the at least 10,000 peptides in said array.

18. The method of claim 1, wherein the method is performed by characterizing an area under a receiver operator characteristic (ROC) curve (AUC) ranging from 0.60 to 0.70, 0.70 to 0.79, 0.80 to 0.89, or 0.90 to 1.00.

19. The method of claim 1, wherein the subject is human.

20. The method of claim 1, wherein the at least 25 differentiating peptides comprise two or more motifs having a sequence selected from the group consisting of SEQ ID NO: 10, 20, 56-66, and 99.

21. The method of claim 1, wherein the at least 25 differentiating peptides comprise three or more motifs having a sequence selected from the group consisting of SEQ ID NO: 10, 20, 56-66, and 99.

22. The method of claim 1, wherein the at least 25 differentiating peptides comprise four or more motifs having a sequence selected from the group consisting of SEQ ID NO: 10, 20, 56-66, and 99.

23. The method of claim 1, wherein binding to the at least 25 differentiating peptides is selective.

* * * * *